(12) United States Patent
Rozakis et al.

(10) Patent No.: US 7,964,390 B2
(45) Date of Patent: Jun. 21, 2011

(54) SENSOR SYSTEM

(75) Inventors: George Rozakis, Lakewood, OH (US); Miklos Gratzl, Mayfield Heights, OH (US); Koji Tohida, Mayfield Heights, OH (US); Jian Yang, Mayfield Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 63 days.

(21) Appl. No.: 11/050,584

(22) Filed: Feb. 3, 2005

(65) Prior Publication Data

US 2005/0221276 A1  Oct. 6, 2005

Related U.S. Application Data

(63) Continuation-in-part of application No. 10/683,315, filed on Oct. 10, 2003, now abandoned.

(60) Provisional application No. 60/541,418, filed on Feb. 3, 2004, provisional application No. 60/501,066, filed on Sep. 8, 2003, provisional application No. 60/444,582, filed on Feb. 3, 2003, provisional application No. 60/417,971, filed on Oct. 11, 2002.

(51) Int. Cl.
  *C12M 1/34* (2006.01)
  *C12M 3/00* (2006.01)
  *G01N 21/76* (2006.01)

(52) U.S. Cl. ............... 435/288.7; 435/287.2; 435/287.9; 435/288.4; 435/808; 436/172; 422/82.05; 422/82.06; 422/82.07; 600/347

(58) Field of Classification Search ............... 435/287.2, 435/287.9, 288.4, 288.7, 808; 436/172; 600/347; 422/82.05, 82.06, 82.07
See application file for complete search history.

(56) References Cited

U.S. PATENT DOCUMENTS

| 5,558,834 | A | * | 9/1996 | Chu et al. ........................ 422/55 |
| 6,011,984 | A | * | 1/2000 | Van Antwerp et al. ....... 600/317 |
| 6,291,200 | B1 | * | 9/2001 | LeJeune et al. ................. 435/20 |
| 6,713,298 | B2 | * | 3/2004 | McDevitt et al. .......... 435/287.8 |
| 6,751,491 | B2 | * | 6/2004 | Lew et al. ..................... 600/345 |
| 2002/0127623 | A1 | * | 9/2002 | Minshull et al. ............. 435/7.92 |
| 2002/0182658 | A1 | * | 12/2002 | Polak et al. ................. 435/7.92 |
| 2004/0020777 | A1 | * | 2/2004 | Miyamoto et al. ............. 205/54 |
| 2004/0058384 | A1 | * | 3/2004 | Bakker et al. ................. 435/7.1 |
| 2004/0234962 | A1 | * | 11/2004 | Alarcon et al. .................... 435/6 |

* cited by examiner

*Primary Examiner* — Nathan A Bowers
(74) *Attorney, Agent, or Firm* — Tarolli, Sundheim, Covell & Tummino LLP

(57) ABSTRACT

A sensor probe suited for implanting into the skin of a person includes a sensor body which may be formed from a polymer which includes 2-hydroxyethyl methacrylate (HEMA). A sensing system is supported by the body. The sensing system exhibits a detectable change when the probe is exposed to the analyte in the fluid. The sensing system may include an enzyme capable of catalyzing a reaction of the analyte to form a reaction product and a dye system which absorbs in the infrared region of the spectrum in response to the reaction product.

11 Claims, 25 Drawing Sheets

FIRST LAYER: INNER DIFFUSION MEMBRANE

CELLULOSE ACETATE (CA)

SECOND LAYER: GOX-CAP/CA MEMBRANE

FOURTH LAYER: CAP-EDA MEMBRANE

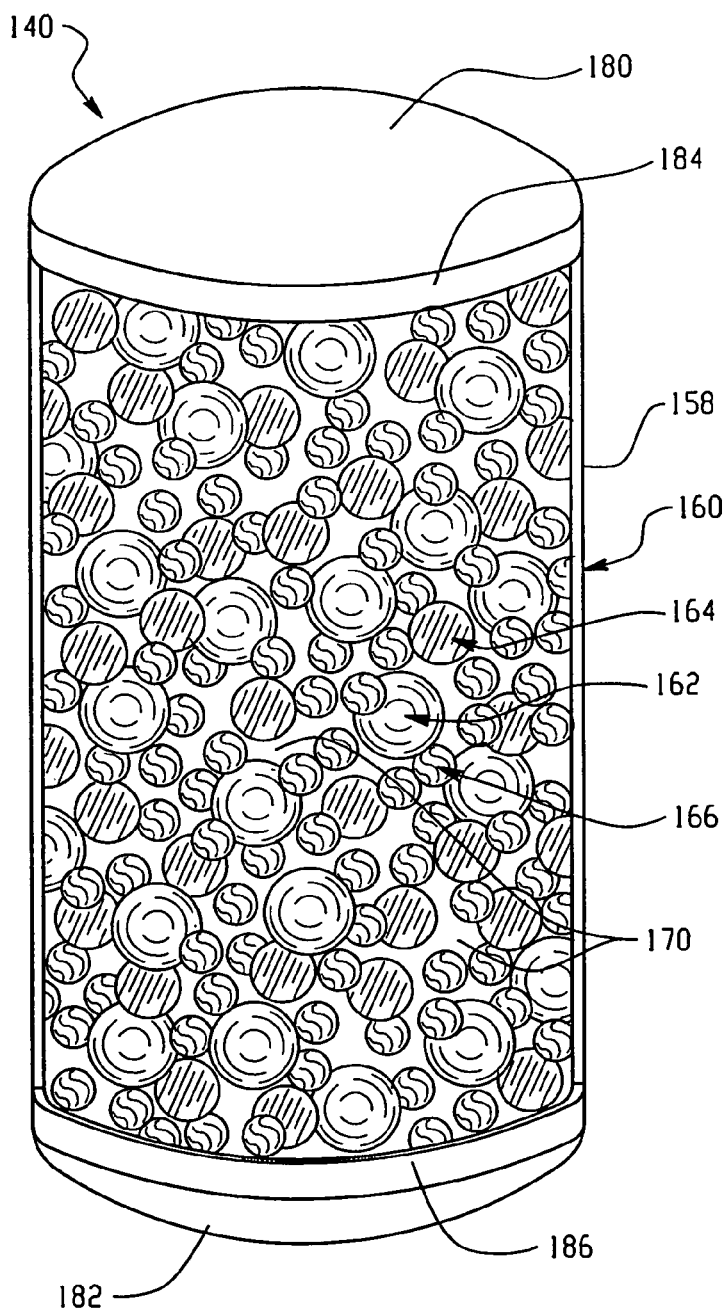
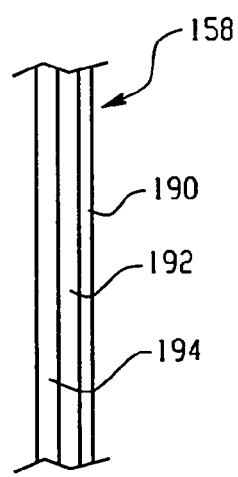
Fig. 17
Fig. 18

SENSOR SYSTEM

This application claims the benefit, as a continuation-in-part, of U.S. application Ser. No. 10/683,315, filed Oct. 10, 2003, and claims the priority of U.S. Provisional Application Ser. No. 60/541,418, filed Feb. 3, 2004, U.S. Provisional Application Ser. No. 60/501,066, filed Sep. 8, 2003, U.S. Provisional Application Ser. No. 60/444,582, filed Feb. 3, 2003, U.S. Provisional Application Ser. No. 60/417,971, filed Oct. 11, 2002, the specifications of all of which are incorporated herein in their entireties by reference.

BACKGROUND OF THE INVENTION

1. Field of the Invention

The present invention relates to in vivo or in vitro monitoring of a biochemical species. It finds particular application in the monitoring of glucose in diabetics, lactate monitoring for those undergoing physical exercise and heart monitoring for those suffering from heart conditions, oxygen monitoring, and the like, and will be described with particular reference thereto. It will be appreciated, however, that the invention has a variety of other applications, both for clinical monitoring and for research purposes.

2. Discussion of the Art

There are numerous applications for in vivo monitoring of biochemical species, both in humans and in other animals. For example, accurate and precise glucose monitoring is desirable to achieve and maintain predictable and safe glucose levels via insulin administration, diet, and/or other factors. Other applications include lactate monitoring, which could be important in monitoring physical exercise, such as in those participating in professional sports and competitions, and in controlling the heartbeats of patients suffering from different heart conditions with pacemakers, defibrillators, etc. Further examples include oxygen monitoring for a number of conditions and pH monitoring when diabetes and other types of acidosis are potential threats. Yet another example is the monitoring of the extracellular level of a drug administered to a patient.

Currently available technologies for such in vivo monitoring involve the introduction of a probe device through the skin into the subcutaneous layer, or into the dermis of a patient to a selected site. The probe is physically connected, typically by electrical wires or other media to a main control outside the patient's body.

The physical connection allows the acquisition of data from the probe and may also be used for its control. Such systems tend to introduce technical inefficiencies and safety concerns that have often resulted in poor usage compliance by the patient and inaccuracies in the monitoring process. For example, the introduction of the probe into the skin sometimes causes acute and, occasionally, chronic pain. There is also the potential for infection at the site or at the insertion point. Further, there is a potential for the sensing elements, which sometimes contain hazardous or toxic materials, electrical wiring, or other parts of the probe device to break or to degrade within the patient. This may result, for example, from natural movements of the patient or from external forces. This raises further safety concerns including the introduction of hazardous or toxic materials to the body and the potential for electric shocks. These problems contribute to a psychological barrier to the use of currently available probes. To limit the likelihood of such problems arising, the probe and its associated wiring are removed from the skin at frequent intervals, typically every few days, and a new site identified. A new or existing probe is then introduced.

The present invention provides a new and improved probe for in vivo monitoring which overcomes the above-referenced problems, and others.

SUMMARY OF THE INVENTION

In accordance with one aspect of the present invention, a sensor probe includes a sensor support body formed from a polymer which includes 2-hydroxyethyl methacrylate (HEMA). A sensing system is supported by the body, the sensing system exhibiting a detectable change when the probe is exposed to the analyte in the fluid.

In accordance with another aspect of the present invention, a sensor probe is provided. The probe includes an enzyme capable of catalyzing a reaction of the analyte to form a reaction product and a dye system which absorbs in the infrared region of the spectrum in response to the reaction product.

In accordance with another aspect of the invention, a method of detecting an analyte in a fluid is provided. The method includes positioning a sensor probe in the fluid. The sensor probe includes a sensing element which in the infrared region of the spectrum in response to the analyte and detecting the change with a detection system.

As used herein, all abbreviations have the following definitions:

"ISF" is used herein to represent interstitial fluid;
"CAP" is used herein to represent cellulose acetate phthalate;
"CA" is used herein to represent cellulose acetate;
"GOX" is used herein to represent glucose oxidase;
"MEMS" is used herein to represent micro-electrical-mechanical system;
"ODS" is used herein to represent octadecylsilanized silica gel beads; and
"$K_M$" is used herein to represent the Michaelis-Menten constant.

One advantage of at least one embodiment of the present invention is that the probe can remain in a patient's body for extended periods.

Another advantage of at least one embodiment of the present invention is that it enables several biochemical species to be monitored simultaneously.

Another advantage of at least one embodiment of the present invention is that safety hazards due to electricity are minimized.

Another advantage of at least one embodiment of the present invention is that risks associated with damage during body movements are minimized.

Another advantage of the present invention is a combination of microsensing elements may be included on a sliver probe, for simultaneous monitoring an enzyme substrate (metabolite), an antigen, various ions ($Na^+$, $K^+$, $Ca^{2+}$, etc) and/or temperature.

Still further advantages of the present invention will be readily apparent to those skilled in the art, upon a reading of the following disclosure and a review of the accompanying drawings.

BRIEF DESCRIPTION OF THE DRAWINGS

FIG. 17 is an enlarged perspective view of a capsule of the probe of FIG. 16;

FIG. 18 is an enlarged sectional view of a side wall of the capsule of FIG. 15;

FIGS. 27a, 27b, 27c, and 27d are images of an optical sensing capsule in a PBS buffer solution containing no glucose (FIG. 27a), 77.0 mg/dL glucose (FIG. 27b), 182.0 mg/dL glucose (FIG. 27c), 305.0 mg/dL of glucose (FIG. 27d), and FIGS. 27e, 27f, 27g, and 27h are corresponding plots of red, green, and blue color (RGB) intensities at each pixel on the red line in the corresponding images.

DETAILED DESCRIPTION OF THE PREFERRED EMBODIMENT

Figure 1:
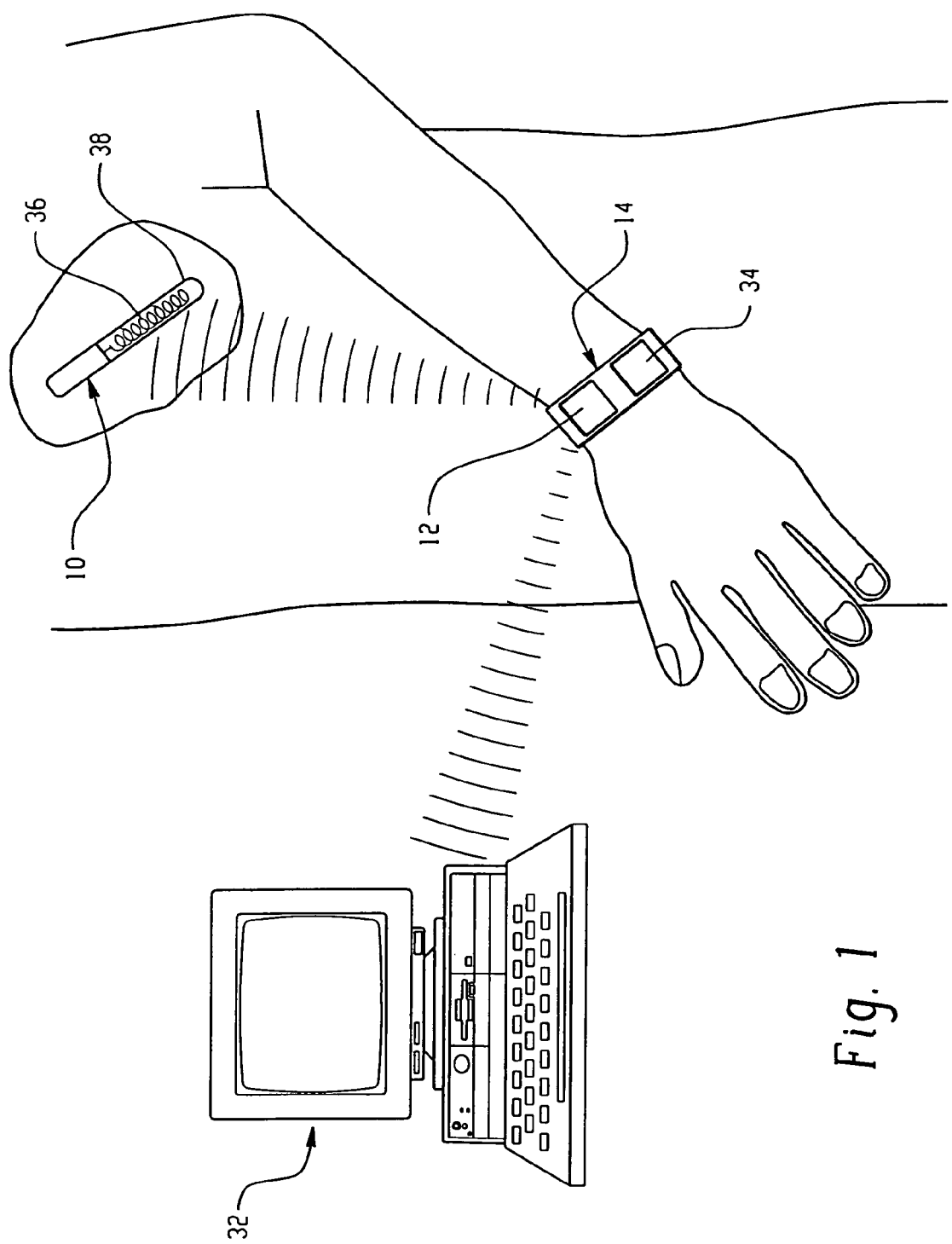
FIG. 1 is a perspective view of a sensor system inserted in a person's body for in vivo monitoring in accordance with one embodiment of the present invention.

With reference to FIG. 1, a sensor system suited to in vivo monitoring of a biochemical species, such as glucose, is shown. While the invention is described with particular reference to glucose as a biochemical species, it will be appreciated that the sensor system is also applicable to the detection of a wide variety of other analytes, as will be discussed in greater detail below. Additionally, while the invention is described with particular reference to in vivo monitoring of analyte concentrations, there exist a number of in vitro applications for the sensor system, which will be addressed below.

With continued reference to FIG. 1, the sensor system includes a sensor probe 10, which is positioned subcutaneously, within the body of a person. The sensor system also includes a detector 12, which is spaced from the probe 10. In the embodiment shown in FIG. 1, the detector 12 is in the form of a watch-like device 14 with a support or strap 16 for attachment to the wrist of the person. In another embodiment (not shown), the detector 12 is in the form of a pager-type device, suited to mounting on a belt or storing in a pocket of the person's clothing. Other detectors, suited to use with optical sensor probes, include color charge coupled devices (CCD), digital cameras, and the like. The sensor system is capable of intermittently or continuously monitoring concentration of one or more selected biochemical species, glucose concentration in the preferred embodiment, in a body fluid, such as the interstitial fluid ("ISF").

The dimensions of the probe 10 are not critical and can vary depending on the fabrication method or application. For example, the probe may be about 100-500 μm wide, about 1-3 mm long, and about 20-500 μm in thickness. In one embodiment, the probe is about 100 μm in thickness. Smaller probes can be formed using microfabrication techniques, as will be described in greater detail below.

The probe 10 may be fabricated by a number of fabrication techniques. For example, microfabrication and MEMS technologies may be employed, as will be discussed in greater detail. These fabrication techniques may be combined with one or more of electrochemical techniques, membrane fabrication technology, enzyme and/or optical dye immobilization, and the like.

Figure 2:
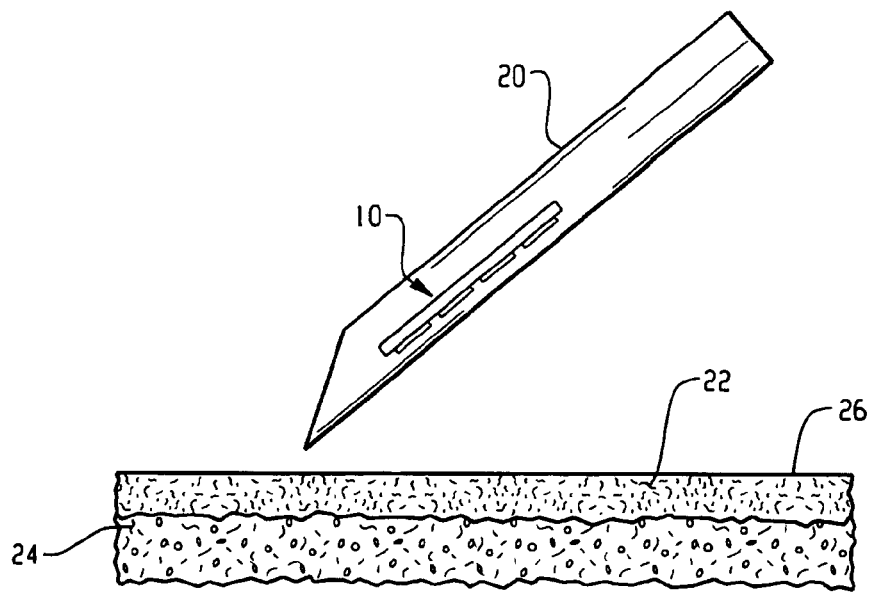
FIG. 2 is a schematic sectional view of a probe and insertion needle prior to insertion in a person's skin.
Figure 3:
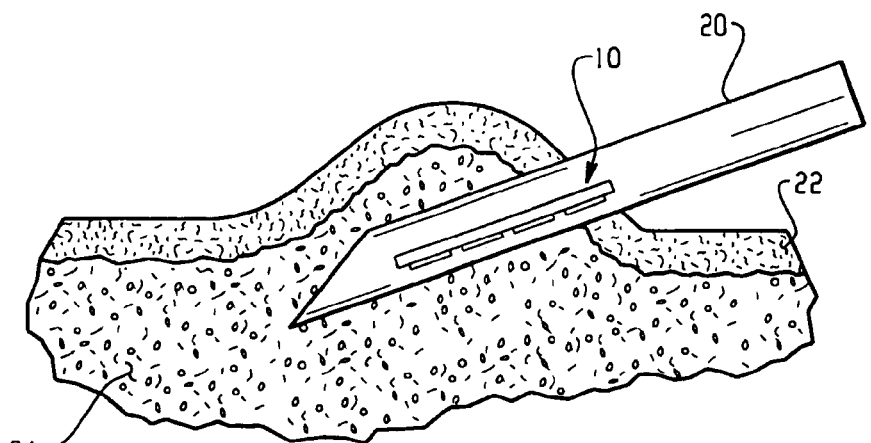
FIG. 3 shows the probe and insertion needle of FIG. 2 during insertion.
Figure 4:
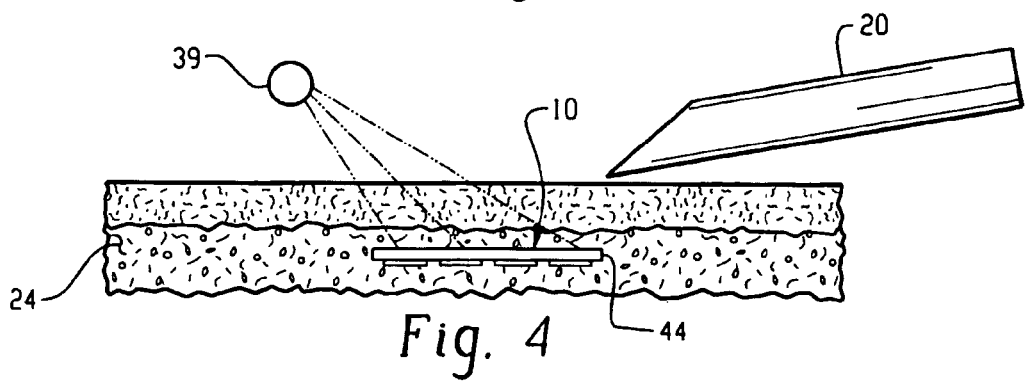
FIG. 4 shows the probe of FIG. 2 following insertion and after removal of the insertion needle.

With reference now to FIGS. 2-4, the probe 10 is preferably implanted beneath the person's skin or other body tissue. For example, by using a syringe needle 20, piston, or other implantation device, the probe 10 can be easily inserted through the epidermis 22 into the subcutaneous tissue 24 below. The probe is positioned roughly parallel to the skin surface 26. Preferably, the probe 10 is entirely buried under the skin, i.e., inside the dermis, where the papillary plexus provides the probe with sufficient biochemical communication with the rest of the body. The probe may have elastic properties, to comply better with body movements. This allows the probe to be virtually painless once the wound due to insertion or implantation of the probe is healed.

Sensor probes similar to those described above may also be formed by ink jet printing or similar printing technology and stored, for example in a holder. To form the holder, a cavity of the dimensions of the sensor probe to be made is formed in a support. The holder is used as a housing for a plurality of sensor probes after fabrication of the probes and before use. The holder cavity has first and second open ends. The probe is liberated from the cavity by a piston. The piston may be attached to a sensor probe delivery needle. The piston enters the cavity via the first open end and pushes the formed probe out through the other open end. The sensor probe is pushed directly into an insertion device (such as a hypodermic needle see FIGS. 2-4) to be used to deliver the probe into the patient's subcutaneous tissue.

Fabrication of an individual sensor probe by ink jet printing within the cavity of the housing can consist of the following steps. A casting liquid is injected into the cavity for forming an outermost coating or layer of the probe (e.g. polyurethane solution) from a hypodermic needle of an ink jet printer (not shown). The outermost coating fills a space between the walls of the cavity and the outside of the delivery needle from the lower open end to the upper open end. Once the layer is applied, the needle is withdrawn. A hollow microtubule is thereby formed inside the cavity of the size and shape of the desired outermost coating of the probe, with one end being open for further delivery. Next, second and subsequent layers are applied to the outermost layer from another suitable inkjet needle or tubing lowered into the cavity to an appropriate depth.

By controlling the outer diameter of the delivery needle tubing, its penetration depth, and the pressure and volume delivered, a structure can be produced that has axial symmetry, including multilayer structures. More than one compartment may be provided for the probe, for example, by inserting more than one needle into the housing cavity while injecting the material for outer layer. This consecutive process can be fully automatic, e.g., controlled by a computer. Several probes can be made simultaneously using the same controlling equipment. Additionally, or alternatively, sequential fabrication of sensor probes is achieved by moving the same needle into subsequent cavities and so forth. A single probe holder can house a supply of probes, e.g., one month supply, such as five, ten, or more probes. Packaging of the probes is thus achieved within the fabrication process.

Delivery of a sensor probe into a patient's subcutaneous tissue is readily achieved with the piston of the delivery device, as described above. Thus, from fabrication to in vivo use, no sensor probe needs to be moved or touched individually since it is made in the holder, and then moved into the patient at an appropriate time from the holder. Aseptic conditions are readily maintained in this manner.

To facilitate positioning of the sensor probe under the skin, the housing cavities in the holder are preferably tilted. This tilt can be up to about 90°, so that probes can be positioned under the skin virtually parallel to the skin surface. This enables a suitable penetration angle to be achieved from the substrate holder. Alternatively, if another device is used for implantation then its hypodermic end can be tilted with respect to its main body. Particularly for multicompartment probes, an alignment which is parallel with the skin surface is desired, since each compartment can then be assessed from outside the body in the same manner. It also enables corrections to be applied equally for each compartment (such as corrections for optical absorption and scattering of the tissue between the probe and the skin surface, if optical reading is used).

The piston used to eject the sensor probe from the housing may be a solid or a liquid piston. Liquid pistons often provide for a smoother delivery from the holder. Such a liquid piston is optionally formed from physiological saline, or other body compatible fluid, to minimize harm to the body if some of the liquid enters the body. Piston liquid is optionally intentionally introduced to the body to provide a cushion for the probe inside the tissue, to minimize tissue damage. Optionally, the piston liquid includes an antiinfection agent to maintain sterility at the introduction site.

A biochemical probe 10 that has no physical connection to a detector device 12 has several advantages. Once the skin has healed at the site, the risks for infection and other negative environmental factors are minimized. Motion related problems, which tend to cause a conventional probe and/or its physical connection to break, possibly inside the patient, and resultant loss of contact with the detector device are also reduced or eliminated. Further, the absence of a physical connection to the detector assists in enabling an autonomous in vivo probe to be implanted into the patient for long periods of time. A preferred type of probe is implanted just under the uppermost layer of skin, similar to a sliver of wood, i.e. splinter, and can thus be described as a "sliver type" probe. Such a probe preferably has a high degree of autonomy due to the lack of physical connection to an exterior device, and can thus be described as a sliver type autonomous in vivo probe.

Such a probe 10 can be operated in a number of different ways, such as:
 1. Via telemetry (which includes the possibility of optical detection through tissue/skin).
 2. By collection of data over time and data retrieval after removing the probe from the patient.
 3. Automatically, e.g., by using a detection of a color change or other detectable chemical or physical property.

While the data storage version may employ a larger device that includes Analog to Digital conversion and digital storage capabilities and optionally, also a power source, the telemetry type can be small (several millimeters) and even microminiature (sub-millimeter), and powered and controlled/interrogated real time, from a device that is outside the patient's body. The probe 10 can be employed for research as well as patient care. The optical probe can be interrogated as frequently as desired.

Communication between the probe 10 and the detector 12 is preferably wireless, e.g., performed by telemetry or by optical detection. Telemetry may be used for a variety of functions, including control of the probe 10, powering its operation, and interrogation of the probe. In this way, the probe 10 and detector 12 can communicate without the need for physical connections. The probe system is therefore much more comfortable to wear, and is virtually free of pain and discomfort, as compared to conventional systems. In particular, the absence of physical connections, such as wires, within the skin and subcutaneous tissue reduces the likelihood of irritation of the tissue with body movements. In addition, the risk of infection is minimized, once the initial wound due to insertion has healed. As a consequence, the probe 10 may remain implanted within the body for longer periods than is conventionally possible. For example, the probe 10 may remain within the body for more than one week, sometimes several weeks or months.

For certain types of probe 10, electrical power is used for operation of the probe. In one embodiment, shown in FIG. 5, the power for the sensing is provided by an internal power source, such as a battery 30. The battery 30 is preferably an integral part of the implanted probe 10. The battery 30 may only be in use during the short periods of an actual measurement, e.g., for a few seconds every several minutes. Other functions of the probe 10 requiring electrical power may also be supplied with power from the battery 30. A control system 32 controls operation of the power source 30 and optionally other components the probe 10. The control system 32 may be part of the probe, the detector 12 or, as illustrated in FIG. 1, be a separate device, such as a PC, which communicates with the detector by telemetry or wires.

In another embodiment, shown in FIG. 1, the power for operating the sensor probe 10 is provided from outside of the body, such as from an AC or DC power source 34 above the skin using electrical inductance. The power source 34 may be mounted on the same support 16 as used for the detector 12. In this embodiment, the probe has an extension wire 36 under the skin to provide sufficient inductive coupling to the outside power source 34. The wire 36 may be finely coiled and positioned inside an electrical insulator 38. In this embodiment, the sensor probe 10 is preferably powered up by the power source 34 before each measurement.

Some probes 10 are able to operate without electrical power. For example where optical methods are used for sensing an optical property, such as a color change of an absorption dye, or emission by a fluorescent dye, or a combination of optical properties, the probe may be able to operate without electrical power. In some cases, a light source 39, such as an electric lamp, is placed above the skin over the buried probe 10 to illuminate the probe beneath the skin (FIG. 4). In some cases, ambient lighting may be sufficient.

In one embodiment, an optical probe 10 is implanted in the person's eye. In this embodiment, the probe is preferably positioned within or below the cornea, but above the white schlera of the eye. Alternatively, the sensor probe is placed below or within the conjunctiva. The cornea, being transparent by nature, allows color changes of the probe to be readily viewed from outside the eye, for example, by the person looking at the eye in a mirror. Alternatively, a detection system 12 employing a color camera or spectrophotometer may be used to view color changes. In yet another embodiment, a detection system 12 may be mounted to the person's glasses. In this embodiment, interference by the tissue in the observed color is minimized due to the transparency of the tissue through which the light travels. Additionally, the white color of the schlera provides a good background material, which provides little or no interference with color readings. Additionally, the natural buffering materials present in the eye maintain pH and ionic concentrations at relatively stable levels. The eye is subject to greater temperature variations than unexposed areas of the skin. Such changes can be compensated for by carrying out readings in a protected temperature environment. Alternatively, the probe 10 may include a temperature detector, as discussed in greater detail below.

In another embodiment, the sensor probe is carried on a contact lens worn in the patient's eye. Glucose measurement on the tear fluid, although generally much lower than in other body tissue, can be correlated with blood glucose levels.

In some embodiments of the probe 10, electrical power is used for sensing and/or control. As well as optionally supplying power for the probe 10, control of the probe 10 may also be provided from outside the body by telemetry. This can be performed by short electromagnetic waves (e.g., radio frequency waves). The detector 12 sends a signal to the probe 10 by telemetry to request the probe to perform a sensing operation. Readout can also use such electromagnetic waves. For example, the probe detects a property of a surrounding liquid medium and generates an encoded signal. The encoded signal is sent by radio waves to the detector 12, where decoding takes place. Alternatively, the probe 10 may be entirely passive in that it does not need external control other than illumination by appropriate light during "reading," as discussed above.

A variety of different sensing methods may be employed, such as electrochemical detection techniques (including amperometric detection and potentiometric detection) and optical sensing methods (including absorption, emission, fluorescence, and the like).

Figure 6:
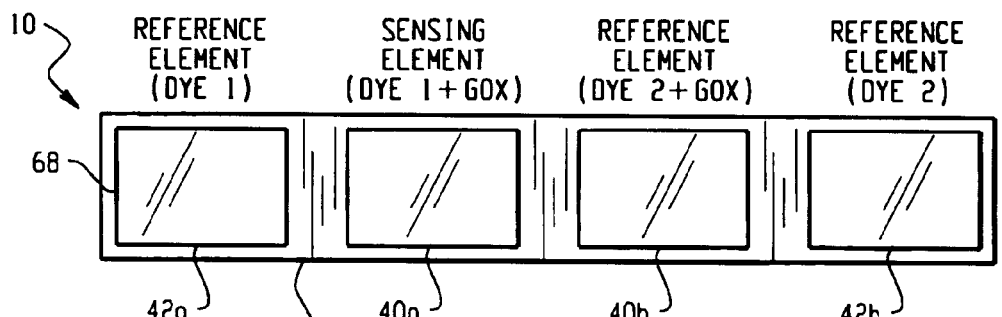
FIG. 6 is a top view of an optical sensing probe in accordance with one embodiment of the present invention.

In one embodiment, the present invention uses optical detection. The color other optical property of the probe 10 changes with changing concentration of an analyte, such as glucose, in the body fluid. By way of example, FIG. 6 shows a probe 10 suited to the detection of glucose in a person's body fluid. The probe 10 is implanted beneath the skin of the person, as shown in FIG. 4. The probe 10 includes one or more sensing elements 40. The sensor probe 10 preferably also includes one or more reference sensing elements 42 for eliminating background responses. The sensing elements 40 and reference sensing elements 42 may be laid down on or otherwise formed in separate regions of a support body in the form of substrate or optical guide 44, such as a transparent plate formed from plastic, glass, ceramic, or the like (FIG. 6). In one embodiment, the plate, or a layer thereof is formed from a 2-hydroxyethyl methacrylate (HEMA) polymer. Or the plate may have a reflective or colored surface to provide contrast from the surrounding body tissue (in this case, the plate is further from the detector than the sensing elements).

A variety of sensing elements 40 are contemplated. These include sensing elements for the detection of glucose, lactate, oxygen, urea, creatinin, and other biochemical species. For example, the enzyme lactase may be used for detection of lactose, galactose oxidase for galactose, urate oxidase for uric acid, and creatinine amidhydrogenase for creatinine. Sensing elements for the detection of pH, temperature, vital ions, such as $K^+$, $Na^+$, and the like, may also be provided. Multiple sensing elements 40 may be provided for a single analyte, for example, to provide redundancy or to provide for different sensitivity ranges, e.g., a first sensing element for high concentrations and a second sensing element for low concentration ranges. Sensors for different analytes may be accommodated in a single probe 10. A number of different sensing elements 40 may thus be associated with a single substrate 44.

The use of multiple redundancies in the sensor probe 10 has a number of advantages, such as enhancing signal-to-noise ratio, increasing sensor probe lifetime, providing stability of readout, and enabling self testing capabilities and automatic calibration adjustments. For example any one or several of the following can be incorporated in the sensor probe 10:

1. A sensing element with an active enzyme and a sensing element with inactive enzyme (preferably the same enzyme)
2. Applying multiple voltage levels to the same sensing element in sequence (electrochemical probes)
3. Employing multiple dyes and/or spectral characteristics (optical sensor probes)
4. Multiple base sensing schemes for the same enzyme reaction. By detecting more than one parameter in a sensing scheme, such as two or more of pH, oxygen, and $H_2O_2$, in the case of a glucose sensing scheme, which are not completely independent of each other, self calibration and checks on sensor probe deterioration can be made. For example, in the case of an electrochemical sensing scheme, oxygen and peroxide concentrations can be determined by pulsing at two different voltages. In the case of an optical sensing scheme, different sensing elements may be used for each of pH, oxygen, and peroxide, for example. Alternatively, for example where fluorescence is used, excitation light may be applied at two or more different wavelengths to detect two or more species in the same sensing element.
5. Multiple enzymes for the same metabolite (for example, both glucose oxidase and glucose dehydrogenase are used in the same probe for glucose detection)

The detector 12 preferably employs algorithms for reconciliation of the redundant and "blank" readouts from the different simultaneous approaches applied, thereby improving signal conditioning, self calibration, self test functions, sensor probe deterioration checks, and the like.

A long term improvement in enzyme based sensing using redundant data is thus possible, allowing sensor probes to remain in the body for extended periods. Utilizing multiple voltage levels, for example, allows improvements in sensor probe stability with respect to surface reduction due to natural metal oxidation. Multiple voltage levels also help to counter inevitable deterioration of noble metals, where used in the sensor probe 10, and of the enzyme, and mass transport through the multiple layers by using currents from each voltage level.

Each sensing element 40 generally includes an indicator material, such as a pH sensitive dye in the case of optical probes, which undergoes a chemical or physical change in response to the analyte to be detected or to a reaction product thereof. Additionally, the sensing element may include one or more detection substances. In general, the detection substance reacts with the analyte or catalyses a reaction of the analyte to produce a detectable reaction product. Or, the reaction/catalyzation results in an intermediate reaction product which undergoes further reaction/catalyzation with a second or subsequent detection substance to form a detectable product. For example, a first detection substance reacts with or catalyses reaction of the analyte to produce an intermediate reaction product. A second detection substance reacts with or catalyses reaction of the intermediate reaction product to produce a detectable product.

The detection substance is generally an enzyme, which catalyses the reaction of the analyte. In the case of glucose, for example, glucose oxidase ("GOX"), glucose dehydrogenase, or other enzyme which catalyses a reaction of glucose, is employed as a detection substance. In the case of lactate detection, lactase may be used.

The indicator material, as mentioned above may be a pH sensitive material, which is responsive to a pH change induced by the analyte or more commonly, the detectable product, for example, by producing a color change (i.e., a change in the absorption wavelength, which may include wavelengths outside the visible range, such as in the IR range), fluorescence, or the like. Exemplary dyes include congo red, neutral red, phenol red, methyl red, lacmoid, tetrabromophenolphthalein, α-naphtholphenol, and the like, with direct immobilization to the membrane matrix via covalent bonding. The dye may be dissolved in organic solvent, such as (NPOE (2-nitrophenyl octyl ether), BEHS (bis(2-ethylhexyl)sebacate), DBE (dibenzyl ether), DOP (dioctyl phthalate), or the like.). Dyes may also be carried in membranes supported by polymeric beads, such as PVC (poly (vinyl chloride)) or silica gel $C_{18}$-reversed phase (ODS beads), as described in greater detail below.

An exemplary dye is one which is sensitive to hydrogen ions (i.e., pH), and which is reversible (i.e., returns to its previous color when the pH returns to its previous level). A preferred pH sensitive dye includes one or more (and preferably all three) of an ionophore, a lipophilic anion, and a lipophilic hydrogen ion sensitive dye (also referred to herein as a chromoionbphore, as it changes color). It will be appreciated that where other ions than hydrogen are to be detected, other lipophilic dyes may be used. The method of using a lipophilic hydrogen ion sensitive dye in combination with an ionophore together in a solvent or membrane is referred to generally herein as the optode technique. The ionophore extracts the ion to be detected and the lipophilic hydrogen sensitive dye exhibits a corresponding color change. The negatively charged anion maintains electrical neutrality in the organic membrane phase.

By optimizing the composition of the pH sensitive optical organic liquid, the maximum color change can be obtained in the desired pH range, typically from about pH 5.0 to 7.5 in the presence of electrolyte at concentrations are approximately equal to those in ISF.

Exemplary chromoionophores include one or more of:
chromoionophore I (9-(diethylamino)-5-(octadecanoylimino)-5H-benzo[a]phenoxazine) designated ETH5249,
chromoionophore II (9-dimethylamino-5-[4-(16-butyl-2,14-dioxo-3,15 ioxaeicosyl)phenylimino]benzo[a]phenoxazine) designated ETH2439,
chrominonophore III (9-(diethylamino)-5-[(2-octyldecyl) imino]benzo[a]phenoxazine), designated ETH 5350,
chromoionophore IV (5-octadecanoyloxy-2-(4-nitrophenylazo)phenol), designated ETH2412,
chromoionophore V (9-(diethylamino)-5-(2-naphthoylimino)-5H-benzo[a]phenoxazine),
chromoionophore VI (4',5'-dibromofluorescein octadecyl ester) designated ETH7075,
chromoionophore XI (fluorescein octadecyl ester) designated ETH7061, and combinations thereof. Note that ETF is the designation of the Swiss Federal Institute of Technology.

Suitable lipophilic anions include KTpClPB (potassium tetrakis(4-chlorophenyl)borate), NaHFPB (sodium tetrakis [3,5-bis(1,1,3,3,3-hexafluoro-2-methoxy-2-propyl)phenyl] borate), sodium tetrakis[3,5-bis(trifluoromethyl)phenyl]borate, sodium tetrakis(4-fluorophenyl)borate, combinations thereof, and the like.

Suitable ionophores include one or more of:
1. Sodium ionophores, such as:
bis[(12-crown-4)methyl]2-dodecyl-2-methylmalonate, designated ETH227;
N,N',N"-triheptyl-N,N',N"-trimethyl4,4',4"-propylidynetris (3-oxabutyramide), designated ETH157;
N,N'-dibenzyl-N,N'-diphenyl-1,2-phenylenedioxydiacetamide, designated ETH2120;
N,N,N',N'-tetracyclohexyl-1,2-phenylenedioxydiacetamide, designated ETH4120;

4-octadecanoyloxymethyl-N,N,N',N'-tetracyclohexyl-1,2-phenylenedioxydiacetamide), designated DD-16-C-5;
2,3:11,12-didecalino-16-crown-5), bis(benzo-15-crown-5), and combinations thereof.

2. Potassium ionophores, such as:
bis[(benzo-15-crown-5)-4'-methyl]pimelate, designated BME 44;
2-dodecyl-2-methyl-1,3-propanedil bis[N-{5'-nitro(benzo-15-crown-5)-4'-yl]carbamate], designated ETH1001; and combinations thereof.

3. Calcium ionophores, such as:
(−)-(R,R)-N,N'-bis-[11-(ethoxycarbonyl)undecyl]-N,N'-4,5-tetramethyl-3,6-dioxaoctane-diamide), designated ETH129;
N,N,N',N'-tetracyclohexyl-3-oxapentaned iamide, designated ETH5234;
N,N-dicyclohexyl-N',N'-dioctadecyl-3-oxapentanediamide), designated K23E1;
10,19-bis[(octadecylcarbamoyl)methoxyacetyl]-1,4,7,13,16-pentaoxa-10,19-diazacycloheneicosane), and combinations thereof.

The lipophilic anion can be incorporated in an organic solvent membrane together with lipophilic chromoionophore or together on the same beads.

One suitable pH sensitive dye includes a mixture of a chromoionophore, such as chromoionophore III, a potassium ionophore, such as 2-dodecyl-2-methyl-1,3-propanediylbis[N-(5'-nitro(benzo-15-crown-5)-4'-yl]carbamate), KTp-ClPB, and optionally BEHS, which is supported by a matrix material, such PVC. The dye composition is preferably optimized to obtain the maximum change in its color in the desired pH range, typically from about pH 5.5 to 7.5 in the presence of electrolytes (e.g., potassium ion) which concentrations are preferably equal to those in the ISF.

The color change of the chromoionophore can be detected by a suitable optical detector, such as a CCD camera or a diode-array-based spectral probe equipped with a microscope. Where the sensor probe is close to skin surface then there may be no need for the detector to include an objective lens. For example, a fiber optic cable containing a fiber bundle of illuminating and receiving fibers positioned on the skin can be used to receive an image of the sensor. A CCD camera is thus not necessary.

By detecting absorbance in the wavelength range corresponding to the protonated form of the chromoionophore (e.g., about 625 nm in the case of Chromoionophore III), changes in the concentration of e.g., glucose can be observed using a suitable calibration curve.

In a more advanced detection system, shape recognition is used. The signal that carries the information sought for is color of the different sensing spots. It is therefore represented, in physical terms, in the form of a spectrum. This may be a reflected, back-scattered, or even a transmittance spectrum in some embodiments, but an important feature is that color for a detecting instrument is equivalent to a spectrum. More precisely, it is the shape of the spectrum which is of concern. Therefore it is independent of intensity. This is not the case for other existing approaches. For example electrochemical methods transduce concentration into current intensity: a single variable. Fluorescence based methods transduce concentration into fluorescence intensity: also a single variable. In the present case, the actual color indicates concentration, meaning that concentration is transduced into the shape of a spectrum. This spectrum may be transmitted or reflected or back-scattered intensity, or some derived variable like absorbance, as a function of wavelength, or frequency of light. It can be acquired by scanning through a given range of light wavelengths or frequencies. The result is a function consisting of a number of value pairs intensity and frequency pairs, for example. The number of these pairs can be 3, 4, or even hundreds, depending on resolution and range. Thus, one concentration value is represented by a large number of independent data points. This means a high degree of redundancy which can be used to improve greatly the statistical quality and reliability of the concentration determined. This is in contrast with intensity-based techniques, where one value is obtained from just one other value, the concentration. To make use of the large amount of information being available in the form of a spectrum, its shape can be used for calibration of the sensor versus concentration, as well as for retrieving unknown concentrations from the calibration.

There are a variety of methods for quantifying the spectrum shape. These include pattern recognition approaches, factor analysis, and curve fitting techniques. In one embodiment, shape is identified with the direction of a vector constructed from the data pairs that make up the spectrum, in a multidimensional space. This makes it possible to identify concentrations using similarity in the direction of the actual data vector and that of some standard, or calibration based vector. Closeness of the two directions is ensured when the angle between two such vectors is small and close to zero.

The advantages of using a shape analysis include: independence of actual optical path lengths which tend to affect intensity but do not affect spectrum shape; a great degree of independence from random noise, since it is sufficient to identify the overall shape of the spectrum, i.e. its lowest frequency components, to identify the concentration that caused it; extreme robustness of the approach in terms of high immunity from potential error sources such as random and some non-random errors; the potential for self testing is also ensured because impossible or unlikely shapes can be readily recognized. These advantages are generally unavailable with conventional evaluation techniques.

It may be noted that ratiometric methods can be considered as an embryonic form of shape analysis. Ratiometry, using only two data pairs, can ensure far better reliability than simple amplitude based techniques. Significantly higher performance can be achieved, however by using a systematic analysis of an entire shape, or at least a subset of it.

In another embodiment, the human eye can also function as the detector, since the color change is readily detectable through the skin. For example, a diabetic patient may be instructed that a change from green to orange is an indication that the blood sugar is too high and thus steps should be taken, such as the injection of insulin, to restore the balance.

With continued reference to FIG. 6, for in vivo monitoring, the illustrated probe substrate 44, can be a soft, strip of non-toxic transparent plastic plate. The size of the strip-shaped plate 44 can be about 0.5 mm in width, 2-3 mm in length, and about 0.1 mm in thickness. Other shapes are also contemplated. The substrate 44 may also be colored to enhance sensitivity. For example, the substrate 44 may be in the form of a white plastic rod, to enhance signal recovery as well as provide with a reference to obtain spectral information on the skin and tissue between the probe 10 and the outside optical detector unit 12.

For optical sensing, the substrate 44 is preferably formed from a transparent material, such as plastic. As shown in FIG. 4, this allows the color changes of the sensing elements to be visible through the substrate. Alternatively, if the probe 10 is inserted in the body with the sensing elements 40 closest to the skin surface, the substrate may be opaque or have a reflective or colored surface to provide contrast for the color changes of the indicator material. Preferably, the plastic is resiliently flexible, such that the probe deflects under the influence of body movements or external impacts.

The probe 10 of FIG. 6 is shown as including two sensing elements 40a and 40b for the same analyte, glucose in a preferred embodiment, which provide redundancy to the system. It will be appreciated that a single sensing element 40 may be provided for each analyte to be detected. Sensing elements for different analytes may also be positioned on the substrate 44. Two reference sensing elements 42a, 42b are also provided. The first and second sensing elements 40a and 40b and first and second reference elements 42a and 42b, are spaced apart on the substrate 44, as discrete regions, such as stripes. The reference elements provide a standard color which acts as a reference by which the color changes of the sensing elements can be compared. The intervening medium, such as the skin 22 through which the color change is monitored influences the detected color change. The detector 12 (or visual comparison) thus uses the reference to eliminate the effects of the intervening medium on the detected color change.

Figure 7:
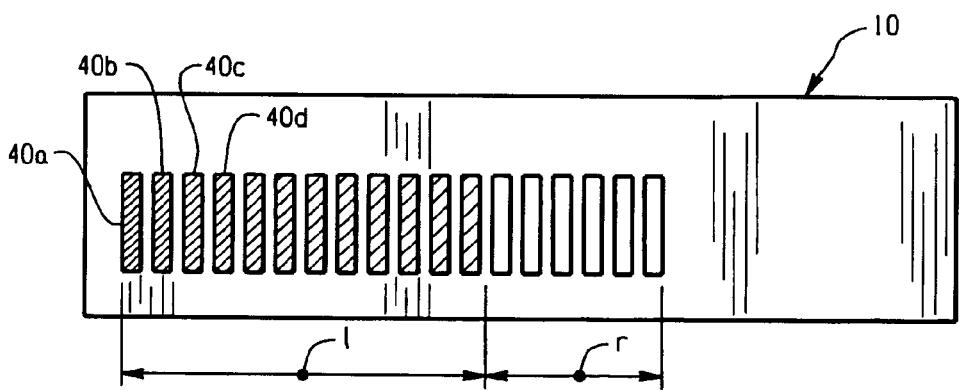
FIG. 7 an alternative embodiment of a probe.

In one embodiment, illustrated in FIG. 7, a series of sensing elements 40a, 40b, 40c, 40d, and so forth, is arranged in a sequence as a sensing element bar 46. Although the bar may form a straight line, it is also contemplated that the sensing elements may be arranged in a circle, for example in the positions of the hours of a clock face. Each successive sensing element is configured to change color at a slightly different analyte concentration, such that the length l of the bar 46 which has changed color is indicative of, for example, the concentration of glucose. This makes visual or mechanical detection of glucose very simple. For example, a person estimates the glucose concentration by estimating the length of the portion l of the bar or the length of the remaining portion r which has not changed color, or simply by evaluating whether the color changed portion l is longer than the remaining portion r. For example, the length of portion l can be selected so each portion l, r is of equal length when the person's glucose level is within a desired optimal range. If portion l is longer than portion r, this indicates that the glucose level exceeds the desired range. If l is shorter than r, the glucose level is below the desired range. For example, in the case where the sensor probe 10 is implanted in the eye of a person may examine the bar 46 in a mirror. A magnifying mirror may assist in viewing the bar 46. Additionally the mirror may be marked with a corresponding reference bar which indicates glucose levels corresponding to different lengths of l or provides a desired length for optimal glucose concentration, or the like. Similarly, where a detection system 12 is used, the detection system measures the length l and/or the remaining portion r to determine the glucose level. In the embodiment in which the detection system forms a part of the person's glasses or contact lenses, a transducer or other distance measuring device may be mounted on the inside of the glasses (i.e., the side closest to the person's eye). Other components of the detection system may be mounted elsewhere, for example in a watch or pocket type assembly. With communication between the transducer and the control system 32 or other components taking place by telemetry or by wired communication.

In the embodiment of FIG. 7, reference sensing elements 42a, 42b, which allow correction for tissue absorption, skin pigmentation and the like, may be eliminated since length, rather than variations in color, is not significantly influenced by these factors.

Figure 8:
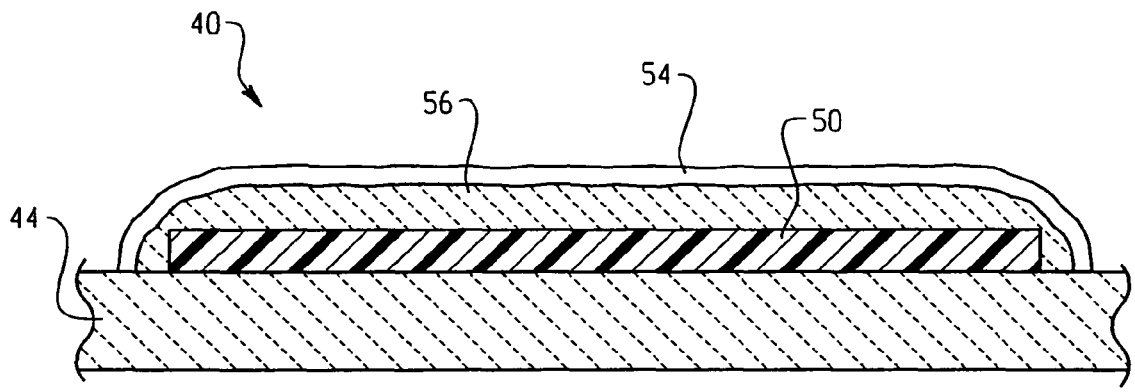
FIG. 8 is a side sectional view through a sensing element of the probe of FIG. 6.
Figure 9:
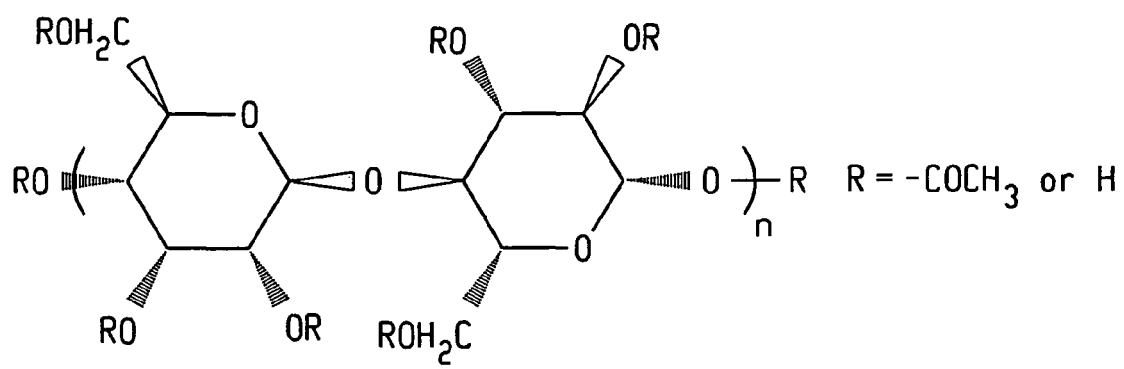
FIG. 9 is a general formula for cellulose acetate.

With reference now to FIG. 8, one embodiment of a sensing element 40 suited to use in the probe of FIG. 6 is shown. The sensing element 40 includes a layer 50 in the form of a membrane of a matrix material, such as a polymer, which supports a detection substance, such as an enzyme, which is specific for the analyte. In the case of glucose, one suitable enzyme is GOX. The matrix material supports the detection substance on a surface thereof (or may be intimately mixed with the detection substance). Suitable matrix materials include cellulose derivatives such as cellulose acetate (CA) and cellulose acetate phthalate (CAP). FIG. 9 shows the general formula of cellulose acetate where each $R_1$ group is independently an acetate, such as —$COCH_3$ ("methyl"acetate), or the like, or H, and each $R_2$ group is generally an acetate. The weight average molecular weight of the CA may be about 30,000. The acetyl content can be 20-50%, e.g., about 40% by weight. Other functional groups are also contemplated in place of some or all of the acetate.

Figure 10:
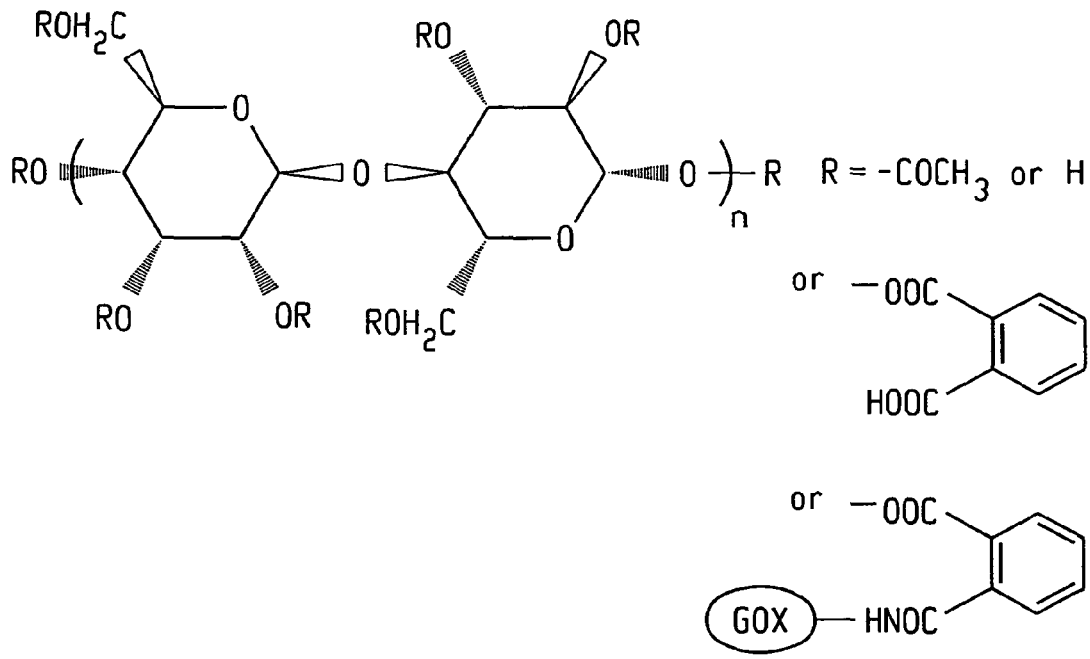
FIG. 10 is a general formula for cellulose acetate phthalate with GOX attached.

FIG. 10 shows the general formula of CAP/CA on which GOX is immobilized. The molecule is similar to cellulose acetate. However, in this molecule, a portion of the acetate groups are replaced with phthalate groups. Typically, about 10-60%, more preferably, about 40% of the acetate groups are replaced with phthalate. The enzyme (GOX in the illustrated embodiment) bonds to the phthalate through one of its amine functional groups. Generally, only a few percent of the phthalate groups are bonded to the enzyme in this way, perhaps 0.1-5%, more preferably, about 1%. CAP is particularly preferred as a membrane material because of its high loading capacity, i.e., its ability to support a relatively large amount of enzyme, as compared with other matrix materials.

Other enzyme supporting membranes 50 in place of CAP are also contemplated. For example, a GOX/BSA (bovine albumin)/glutaraldehyde membrane may be employed.

An indicator material, such as a dye is also intimately mixed with, or supported on the matrix material in layer 50'. The dye is responsive to a reaction product of the enzyme catalyzed reaction of the analyte or of a product produced by further reaction of the reaction product. In the case of glucose detection, the indicator may be a light-absorbing pH-sensitive optical dye such as those previously discussed. With reference also to FIG. 6, in one embodiment, the first sensing element 40a includes a first dye, such as a light absorbing, pH-sensitive optical dye having a first pKa and the second sensing element 40b includes a second dye, such as a light absorbing, pH-sensitive optical dye having a second, different pKa. The first and second reference elements 42a and 42b include the first dye and the second dye, respectively, optionally combined with a matrix material similar to that used for the sensing elements 40.

The layer 50 may be about 10 μm in thickness. The CAP, CAP/CA, or other matrix material is preferably loaded with GOX and the selected dye and applied to the substrate 44 to form the sensing elements 40a, 40b. For example, the GOX and selected optical pH indicator dye are covalently attached to the membrane 50. Other sections of the plate 44 are covered with CAP or CA membranes but are loaded with the two dyes without GOX to provide the reference sensing elements 42a, 42b. The composition of the GOX-dye membrane(s) is designed and optimized to obtain maximum color change within the clinical glucose concentration range to be detected, or a selected range of interest as will be described in further detail below.

With continued reference to FIG. 8, a second layer 54 in the form of a membrane comprising a protective material optionally overlies the sensing and/or reference elements 40, 42. The protective material may include a material for prevention of blood clotting and thrombus formation, such as heparin, attached to a support material such as chitosan or other positively charged material suitable for immobilizing the hydrophilic heparin. The protective chitosan/heparin membrane layer 54 may be about 10 μm in thickness. The membrane 54 is preferably spaced from the CAP membrane 50 via a thin negatively charged hydrophilic gel layer 56 as the materials of layers 54 and 50 are generally incompatible. Where these layers 50, 54 are compatible, the layer 56 may be eliminated. The gel layer 56 may be about 100 μm in thickness. Suitable materials for the gel layer include, for example, polyacrylates, polyvinyl sulphonic acid, polyvinybenzene sulphonic acid, Nafion™, and the like.

One method of preparing the sensor probe 10 of FIGS. 6 and 7 includes dipping a plastic plate in a CAP and/or CA solution or spraying or otherwise coating the substrate 44 with the CAP/CA. The applied CAP/CA may be treated with a coupling agent, such as a mixture of 1-ethyl-3-[3-(dimethylamino)propyl]carbodiimide hydrochloride (ECD-HCl) and N-hydroxysuccinimide (NHS) to speed up the coupling reaction between the phthalate groups and glucose oxidase enzyme. The treated CAP/CA membrane is then treated with a PBS solution containing GOX and a pH indicator dye, such as those previously described. The dye also has an amine group for attachment to the phthalate group. The membrane 50 is then covered with a poly(acrylate) gel layer 56, which may be prepared, for example by radical co-polymerization of sodium acrylate and N,N'-methylenebis(acrylamide). The gel layer is covered with a chitosan/heparin protective membrane 54.

To use the probe, it is inserted into the person's body, as described above (FIGS. 2-3), with the substrate 44 uppermost. In this position, the membrane layer 50 is the closest layer of the sensing element 40 to the skin surface 26. When it is time to detect an analyte, a light source 39 (or ambient light) is optionally positioned over the skin (FIG. 4). During a sensing procedure, the light travels through the upper layer of skin above the probe to the sensing elements. The detector 12 (or person's eye) detects color changes that occur and determines the glucose concentration by reference to calibration charts, look up tables, or the like. Or, the sensing elements may be configured to provide a color change only when glucose concentrations are outside a predetermined acceptable range. Optionally, the optical probe 10 is controlled and readouts are obtained by telemetry. The detector 12 sends a signal by telemetry to the probe to initiate a sensing procedure.

In one embodiment, the dyes immobilized on the probe change color (absorption wavelength) dependent on the concentration of the analyte species being monitored. The color is recognized by the detector 12 using a light source 39 (which may be integral with the detector), and a suitable color measuring device, such as spectrophotometer with a digital data processing unit. For example, a spectrophotometer detects the absorbance of light at one or more wavelengths or wavelength ranges where the dye absorbs. With increasing concentration of glucose, the absorbance at the selected wavelength either increases or decreases, depending on whether the absorbance is due to a protonated or an unprotonated form of the dye. The absorbance is then correlated with the concentration of glucose, for example, by using an algorithm or look up table based on precalibration with solutions of known glucose concentrations covering the range of concentrations to be measured. A color charge coupled device (CCD) may alternatively be used as a color measuring device.

Optical filtering due to the skin and/or tissue between the probe 10 and the detector 12 is accounted for by reference elements 42. In one embodiment white and black reference elements 42 are used, although other colors and intensities are also contemplated. Alternatively or additionally, reference elements separately contain dye but no enzyme, dye plus enzyme, or other reference materials. Analyzing the colors of each is used to filter out the optical effects of tissue and skin, and optionally also pH and other (bio)chemical effects of the surrounding tissue.

Alternatively, different spectral properties are used for visual assessment of the state of health of the probe's wearer by the wearer or by an attending physician. Visual examination generally permits a qualitative or semi-quantitative assessment rather than a quantitative measurement of glucose level. In many cases, however, such an assessment is sufficient for diabetes management.

The implanted sensor probe 10 is reversible, in that when the cause of the detectable color change is removed (glucose in the exemplary embodiment), the color change is reversed. Thus, when the glucose concentration in the ISF drops, the rate of transport of glucose to the immobilized enzyme is reduced. Gluconic acid concentration in the region of the dye gradually diminishes due to diffusion through the membrane layers. The pH increases and the color change is reversed.

Figure 11:
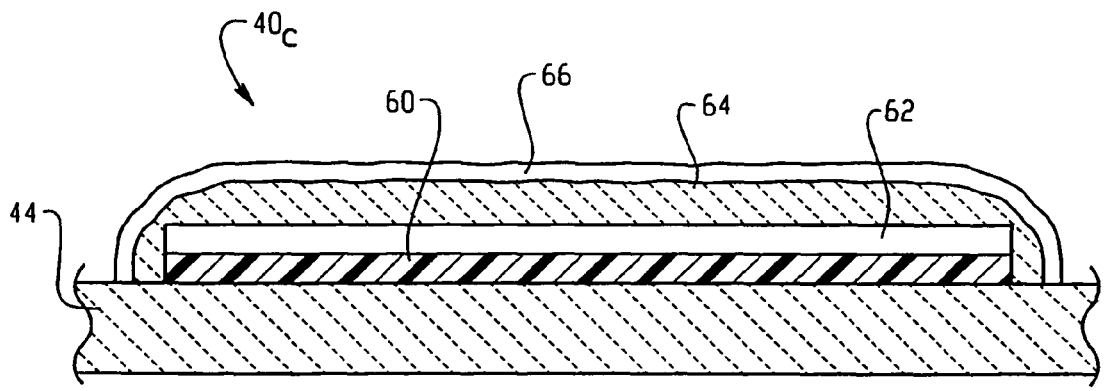
FIG. 11 is a side sectional view of an alternative embodiment of a sensing element for the probe of FIG. 6.

With reference now to FIG. 11, in an alternative embodiment of the probe 10, the dye and enzyme are associated with different layers of a sensing element 40c. Sensing elements 40c are formed by covering sections of a strip-shaped plate 44 with a solvent polymeric membrane layer 60, which contains the dye. The layer 60 may be prepared by forming a pH sensitive solvent polymeric membrane cocktail comprising a solvent, such as tetrahydrofuran (THF) in a solution containing a membrane supporting material, such as poly(vinyl chloride) (PVC), a membrane solvent (e.g., 2-nitrophenyl octyl ether), which acts as an organic solvent for lipophilic reagents (such as chromoionophores, ionophores, and lipophilic anions), a hydrogen ion-selective dye (also referred to as a hydrogen ion-selective chromoionophore) which exhibits a color upon exposure to hydrogen ions in the organic solvent, which color varies as the concentration of $H^+$ varies, a lipophilic anion-exchanger, and an ionophore for uptake and release of ions such as $Na^+$, $K^+$, $Ca^{2+}$ into or out of the organic solvent. This cocktail is cast onto a plate 44 and allowed to dry until the THF has evaporated. The thus obtained PVC membrane 60 is covered with a CAP/CA membrane 62, similar to layer 50, but without the dye. Since layer 60 is hydrophobic, it is desirable to have layer 60 below the CAP layer 62. The layer 62 can be applied by a spraying method. The layer 62 is treated with ECD-HCl and NHS (coupling agents) and then with a PBS solution containing GOX, as for membrane layer 50. A gel layer 64, such as a layer of polyacrylate, and a protective layer 66, such as a chitosan/heparin membrane are applied, as for the embodiment of FIG. 8, although it will be appreciated that layer 64 may be eliminated where layers 62 and 66 are formed from compatible materials.

The dye-containing layers 50 or 60 of sensing elements 40a, 40b, 40c, (whether provided by the method of FIG. 8 or FIG. 11) are separately formed in different regions of the plate 44 (indicated by the rectangular boxes 68 in FIG. 6). Each sensing element preferably contains a different hydrogen ion sensitive lipophilic dye with a different pKa value. Other layers 54, 56, 62, 64 of the sensing elements may be laid down to cover all dye containing sections.

For the probes of FIGS. 6, 7, and 10, protective layer 54, 66 may elute a material which improves the compatibility of the probe with the surrounding issue, such as an anti-infection agent and/or an antihistamine. Alternatively, a separate protective layer (not shown) containing the anti-infection agent and/or antihistamine is optionally provided. Alternatively or additionally, a membrane which excludes anions and/or cations may be provided to ensure higher sensitivity and selectivity. This reduces the buffer capacity (ability to buffer the pH) in the sensing domain with respect to the ISF. When buffer capacity is lowered, a small change in the number of ions to be detected has a larger impact on the pH, and thus a larger color change by the dye. One suitable ion-excluding membrane is formed from polyvinylsulphonic acid, polyvinylbenzenesulphonic acid, Nafion™, or the like.

Glucose in the ISF can easily diffuse through the protective membrane 54, 66 and the hydrophilic gel layer 56, 64 due to its very high permeability and reach the GOX-loaded membrane 50, 62. In the GOX-loaded membrane, the following enzyme reaction occurs:

$$\text{Glucose} + O_2 + H_2O \xrightarrow{\text{GOX}} \text{Gluconic acid} + H_2O_2$$

Because the above enzyme reaction produces gluconic acid, the pH in the enzyme-loaded membrane 50, 62 changes with changing concentration of glucose in the ISF. The color, namely the absorption spectrum, of the pH-indicator dye covalently attached to the enzyme-loaded membrane 50 (FIG. 8) or of the dye entrapped in the liquid membrane 60 under the enzyme-loaded membrane 62 (FIG. 11) will change due to the pH change in the dye membrane. It is this change in the spectrum which is detected and used to determine glucose concentration.

Figure 12:
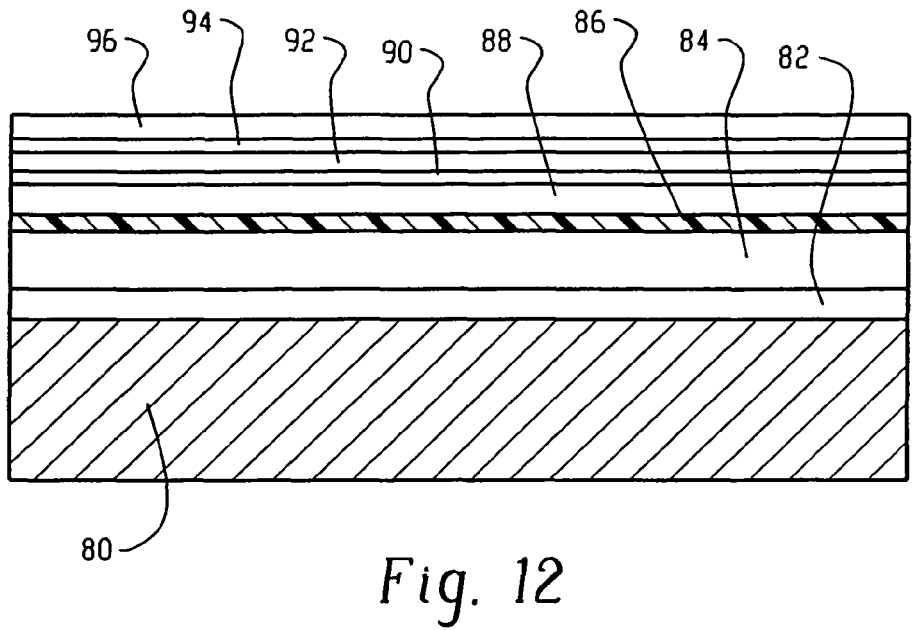
FIG. 12 is a side sectional view of a GOX-based membrane with eight individual layers on the surface of a Pt electrode in accordance with an embodiment of the present invention.

FIG. 12 shows another embodiment of a probe 10, which is positioned below the surface of the skin. The probe is positioned in optical communication with a fiberoptic cable 68, which may be buried under the skin surface, as show, or positioned above the skin. The fiberoptic cable is in optical communication with a suitably positioned detector 12 outside the skin. The fiberoptic cable and probe may be integrally formed. In one embodiment, walls of the fiberoptic cable may be used as the substrate 44.

Figure 5:
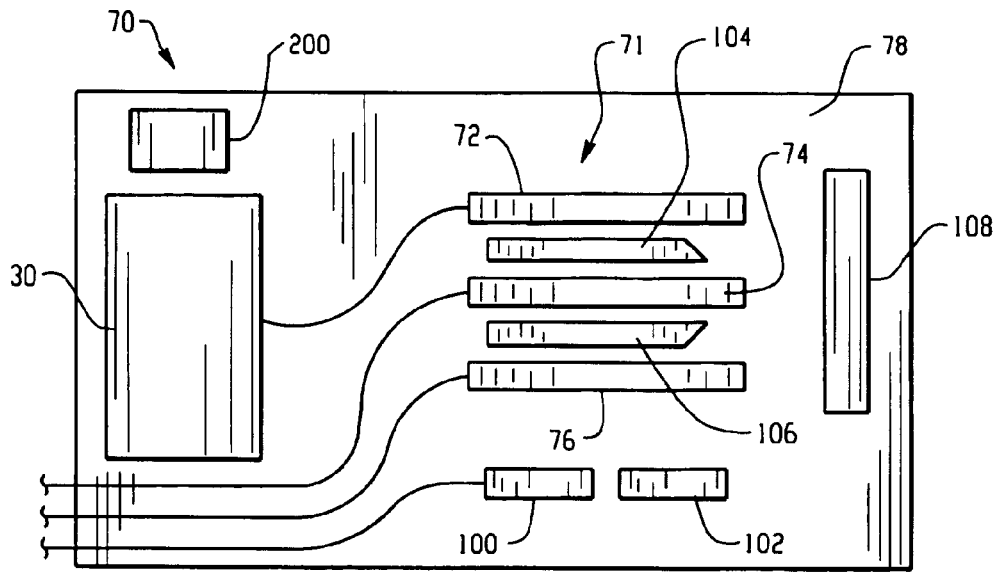
FIG. 5 is a schematic top view of a battery powered probe in accordance with the present invention.

In another embodiment, a probe 70 uses electrochemical detection of an analyte, such as glucose. Similar layers to those described for the optical probe are optionally used for such an electrochemical probe. In place of a dye, the probe 70 uses an electrode detection system. By way of example, FIG. 5 shows a probe 70 suited to the electrochemical detection of glucose in a person's body fluid. The probe 70 includes one, or several sensing elements 71. Each sensing element includes one or more microelectrodes. FIG. 5 shows an exemplary electrochemical probe, with a three electrode system, i.e., a working electrode 72, a counter electrode 74, and a reference electrode 76. The working electrode is preferably formed from a conductive, electrochemically inactive material, such as carbon or a noble metal, e.g., gold (Au) or platinum (Pt). It will be appreciated that a two electrode system may alternatively be employed in which the reference and counter electrodes are replaced by a single electrode. The elements of the probe 70, such as electrodes 72, 74, and 76, are laid down on a substrate 78, such as a layer of plastic, glass, ceramic, or the like, of about 0.001-1 mm in thickness.

Electrochemical detection may employ amperometric or potentiometric detection techniques, with amperometric detection being preferred for glucose monitoring. The probe 70 is implanted beneath the skin of the person. Microfabrication techniques are preferably used to form the implantable probe 70.

FIG. 12 shows an exemplary embodiment of a working electrode 72 for the electrochemical probe 70. Working electrode 72 includes a base electrode 80 formed from an electrically conductive material, such as platinum. A multilayer composite membrane comprising several membrane layers covers the detecting portion of the base electrode 80. Membrane layers 82, 84, 86, 88, 90, 92, 94, 96 (eight individual layers on the surface of the Pt electrode) are shown in the exemplary embodiment. The base electrode 80 may be in the form of a disk, rectangle or the like, of, for example, a diameter of about 100 μm. In the exemplary embodiment, a GOX-based membrane is employed, although it will be appreciated that other enzymes are also contemplated.

A first membrane layer 82, adjacent the electrode 80, is formed from CA (FIG. 9). The first layer 82 acts as an inner diffusion layer in which the products of the enzyme reaction as well as small molecules in the biological fluid, such as hydrogen peroxide, protons, and oxygen diffuse freely. The first layer 82 provides a diffusion zone between the bioreactor layer 84 (CAP-enzyme layer) and the amperometric base electrode 80 (Pt in this case). The membrane layer 82 preferably has a thickness of around 5 μm.

A second layer 84 is a CA/CAP layer, similar to layer 62 of FIG. 11, to which the enzyme GOX is bonded (FIG. 10). Layer 62 is preferably about 5-50μ in thickness, more preferably, about 10 μm in thickness. Layer 84 is used here to immobilize GOX with a high local enzyme density.

Optionally, a third layer 86 is a layer of polyurethane. The thickness of the third layer is preferably about preferably about 2-50μ in thickness, more preferably, about 5 μm. The polyurethane layer 86 is used to, regulate diffusion of glucose, leading to the improvement of linearity and dynamic range of probe responses. While layer 86 is shown as being adjacent layer 82, it is also contemplated that layer 86 may be elsewhere in the multilayer composite membrane, e.g., as the outermost layer.

Figure 13:
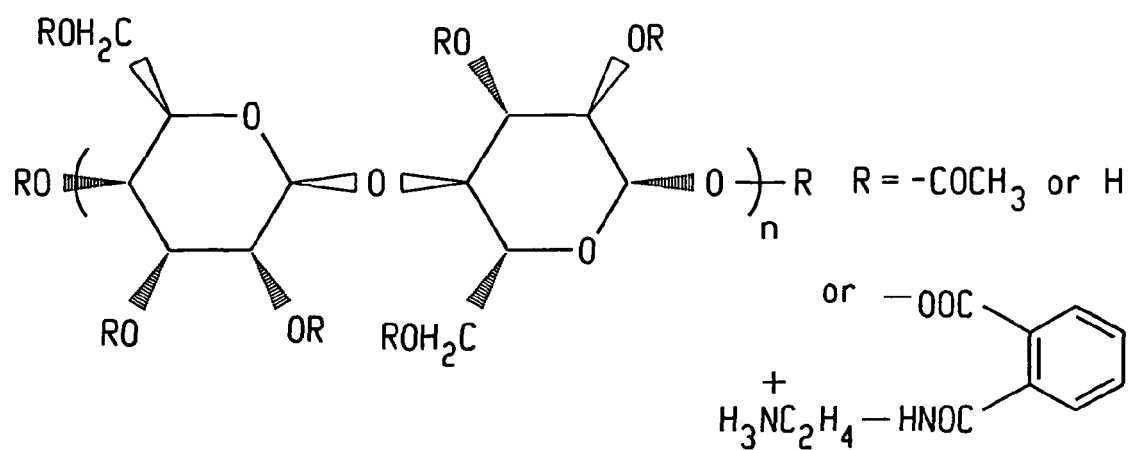
FIG. 13 a general formula for a CAP-EDA molecule.

A fourth layer 88 is a layer comprising CAP-EDA (ethylenediamine). FIG. 13 illustrates a general formula for the CAP-EDA molecule. The molecule may be derived from CAP by reacting the carboxylate groups with ethylenediamine. The reaction is generally a 100% conversion of the carboxylate groups to the ethylamine group. The thickness of the fourth layer is preferably about 2-50μ, more preferably, about 5 μm.

A fifth layer 90 is a CA layer similar to the first layer 82. The thickness of the fifth layer is preferably about 1-20μ, more preferably, about 2 μm. The layer 90 is used to separate the different CAP membranes 88, 92 that have different functionalities.

A sixth layer 92 is a layer of CAP. The thickness of the sixth layer 92 layer is preferably about 2-50μ in thickness, more preferably, about 5 μm.

A seventh layer 94 is a CA layer, similar to layer 90. The thickness of the seventh layer is preferably about 1-2μ, more preferably, about 2 μm. The layer 94 is used to separate the different CAP membranes 92, 96 that have different functionalities.

Figure 14:
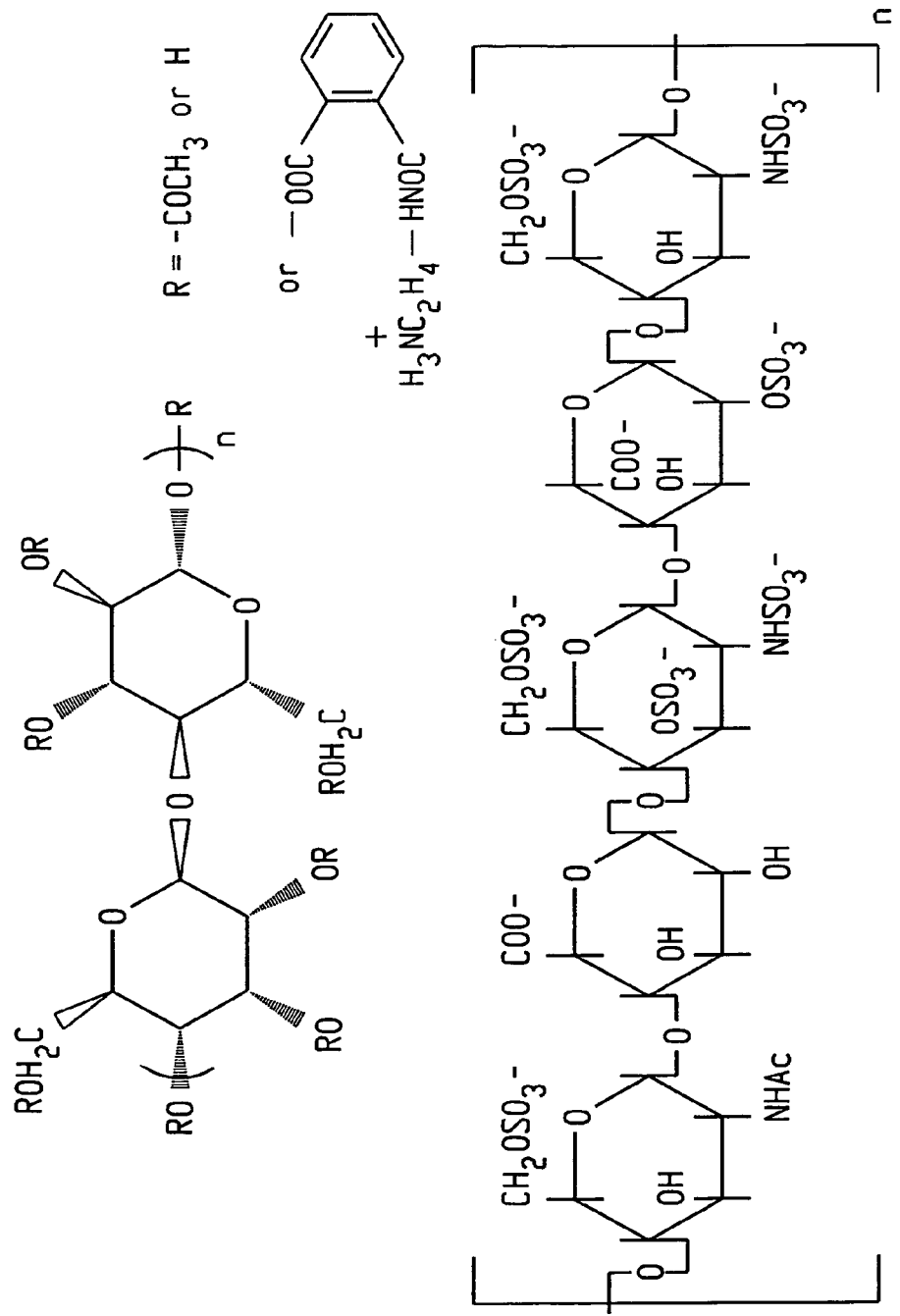
FIG. 14 a general formula for a CAP-EDA/heparin molecule.

An eighth layer 96 is in contact with the interstitial fluid and may be, for example, a CAP-EDA/heparin layer. FIG. 14 shows the molecular structure of the CAP-EDA/heparin molecule. The molecule is similar to the CAP-EDA molecule, but a portion of the carboxylic groups are bonded to heparin in place of EDA. The thickness of the eighth layer 96 is preferably about 2-50μ, more preferably, about 5 μm.

The CAP-EDA layers 88, 96 are used to exclude charged interferences (positive, and negative, by having both CAP-EDA and CAP layers, one with positive and another with negative excess charge). Thus, the CAP layers listed above as simple CAP can be chemically modified according to the different tasks they are to fulfill.

It will be appreciated that fewer or additional layers may alternatively be employed. It will be appreciated that the membrane layers employed in the embodiment of FIG. 12 may also be employed in an optical probe, similar to that of FIGS. 6, 8, and 11.

Other embodiments of the optical probe 70 are also contemplated, in which additional layer are provided in the sensing elements 72.

The CAP-enzyme membrane has several advantages over conventional structures used for enzyme immobilization, such as:

1) Enzyme loading with very high densities is feasible because the CAP contains large amounts of phthalate group (e.g., 40 wt %). Such a CAP-enzyme loaded membrane provides with very high substrate sensitivities. (Among amperometric glucose sensors reported so far, a sensor probe with a GOX-loaded CAP membrane exhibits the highest sensitivity per surface area to glucose: 7.5 nA/mM for a 100 µm diameter disc electrode.)
2) High substrate permeability, which allows for a very short response time. For a GOX-CAP membrane, the typical response time is within 20 seconds.
3) The CAP membrane itself is nontoxic, and has high biocompatibility. Thus, it is applicable for in vivo, and even for log-term implanted, sensor probes.
4) Chemical modifications of the CAP membrane are straightforward: it is possible to immobilize several kinds of enzymes and/or indicator dyes and other functionalities on one CAP membrane.

Telemetry is optionally used for powering the probe 70, control of the probe, and reading the signal. For example, inductive coupling between the probe and detector 12 is used.

The probe 70 may have several additional sensing elements. For example, a sensing element 100 is used to accommodate a denatured enzyme in place of the active enzyme used in the sensing element 72. Another sensing element 102 provides for blank measurements, i.e., is a reference sensing element or control. Other sensing elements 104 are used to provide additional redundancies, such as several voltage levels in assessing amperometric response. Additional sensing elements 106 may be provided such that several enzymes can be used for simultaneous or separate detection of the same or different analytes. Background concentrations, pH or temperature, can also be monitored by an appropriate sensing element 108, for filtering out interfering effects of changes in body chemistry.

In one embodiment, potentiometric detection principles are employed, e.g., for monitoring pH directly with a micro pH sensing electrode 108 as part of the sensor probe 70. This approach allows much simpler circuitry than amperometry, and far less power. Therefore, potentiometric detection may be advantageous for autonomous probes 70 implanted at deeper sites where inductive powering from the outside tends to be less effective. Optionally, a microminiature battery 30 provides sufficient power to the probe for extended periods of time.

By using a multilayer membrane structure, such as that shown in FIGS. 7, 10, and 12, based on a combination of CA, CAP, and optionally other membrane matrices, a number of different "tasks" are readily performed. The first layer in direct contact with an electrode 80 or optical guide 44 is preferably a diffuse layer for both reaction products of the enzyme reaction and for co-enzymes, such as oxygen. The next layer may be based on CAP, and can be used to immobilize an enzyme at high density (high enzyme loading).

For multi-analyte monitoring, more than one enzyme may be immobilized on the CAP layer or layers. Immobilization of multiple optical dyes, or both enzyme(s) and dye(s), or other functionalities on the same CAP layer is also contemplated.

The enzyme-loaded CAP membrane is optionally covered with one or more further functional or protective layers, such as layers comprising: positively charged cellulose, negatively charged cellulose, chitosan, CAP-heparin, chitosan-heparin, polyurethane, polyvinyl pyrrolidone, acrylic polyester, fluorocarbons, silicone rubber, and the like. The formation of the layers is readily achieved by a suitable serial combination of micro-spraying and/or dipping methods, as discussed in greater detail below. The positively charged cellulose layer and the negatively charged cellulose layer act as protective membranes to prevent electrochemical or other interference from positively charged and negatively charged species such as heavy metal ions, cathecol amines, and ascorbates, respectively. The CAP-heparin layer is a protective membrane to prevent thrombus formation, and thus is particularly useful for in vivo applications. Polyurethane, polyvinyl pyrrolidone, acrylic polyester, or fluorocarbon-based protective layers may further improve the biocompatibility of the multilayer membrane structure, and thus, the entire probe. Also these layers may control the diffusion of the target analyte(s), leading to the improvement of linearity and dynamic range of the probe's response.

To avoid any infection due to transcutaneous probe placement, an outer layer containing an antibacterial agent (e.g., ibuprofen) can be added to any of the probes 10, 70, 110, 210. This helps to minimize the risk of an initial infection. After wound healing the skin begins to act again as the best biological barrier against infections.

A CAP-based enzyme membrane with multiple layer structure is an effective active membrane for in vivo diagnostics, particularly for implantable probes for long-term continuous monitoring of analyte concentrations, such concentrations of glucose, urea, creatinin, and the like, with high sensitivities, good biocompatibility, and an exceptionally low background signal. The membrane structure is particularly useful for probes which are to be used for complex media where severe interferences and/or damage to the probe is expected. Another area of use is in very small probes (e.g., 1-2 mm long, 200-300µ in width) where high enzyme loading is desirable to achieve a sufficient signal-to-noise ratio. Yet another area is in microprobes (e.g., to minimize pain and discomfort to patients when in vivo monitoring is needed, by using a microminiature probe (e.g., 1-2 mm long, 200-300µ in width) where the high enzyme loading is beneficial.

The following processes may be used to construct the multilayer structures described above. Each layer may be very thin (down to several microns), and the different layers may be dissolved in the same solvent, or in different solvents. An example for such layered structures is a combination of CA-CAP (-enzyme, -dye, and -other functionalities) membranes overlaid on each other.

The first layer 82, in direct contact with an electrode 80 or optical guide 44, as noted above, is preferably a diffuse layer for products, and eventual co-enzyme(s) (e.g., oxygen) of the enzyme reaction(s). This layer can be formed by dipping the base electrode 80 or optical guide 44 into a solution containing a solvent and a matrix material. Suitable solvents include organic solvents, such as acetone, furan solvents, such as THF, lower alcohols, such as ethanol and propanol, and the like. For example, the electrode 80 or optical guide 44 is dipped in an acetone solution containing about 0.1-10 wt %, more preferably, about 1 wt % of cellulose acetate (CA), and then drying it in air. This first layer is covered with a CAP membrane 84 by dipping or spraying a solution of CAP in a suitable solvent, such as acetone, for example, a 0.1-5 wt %, more preferably, about a 1 wt % CAP in acetone solution. The optimum concentration is dependent, to some degree, on the desired thickness of the layer, and is limited by the solubility of the membrane material in the selected solvent. Acetone is a particularly effective solvent for CA and CAP due to the high solubility of these membrane materials in acetone.

Figure 15:
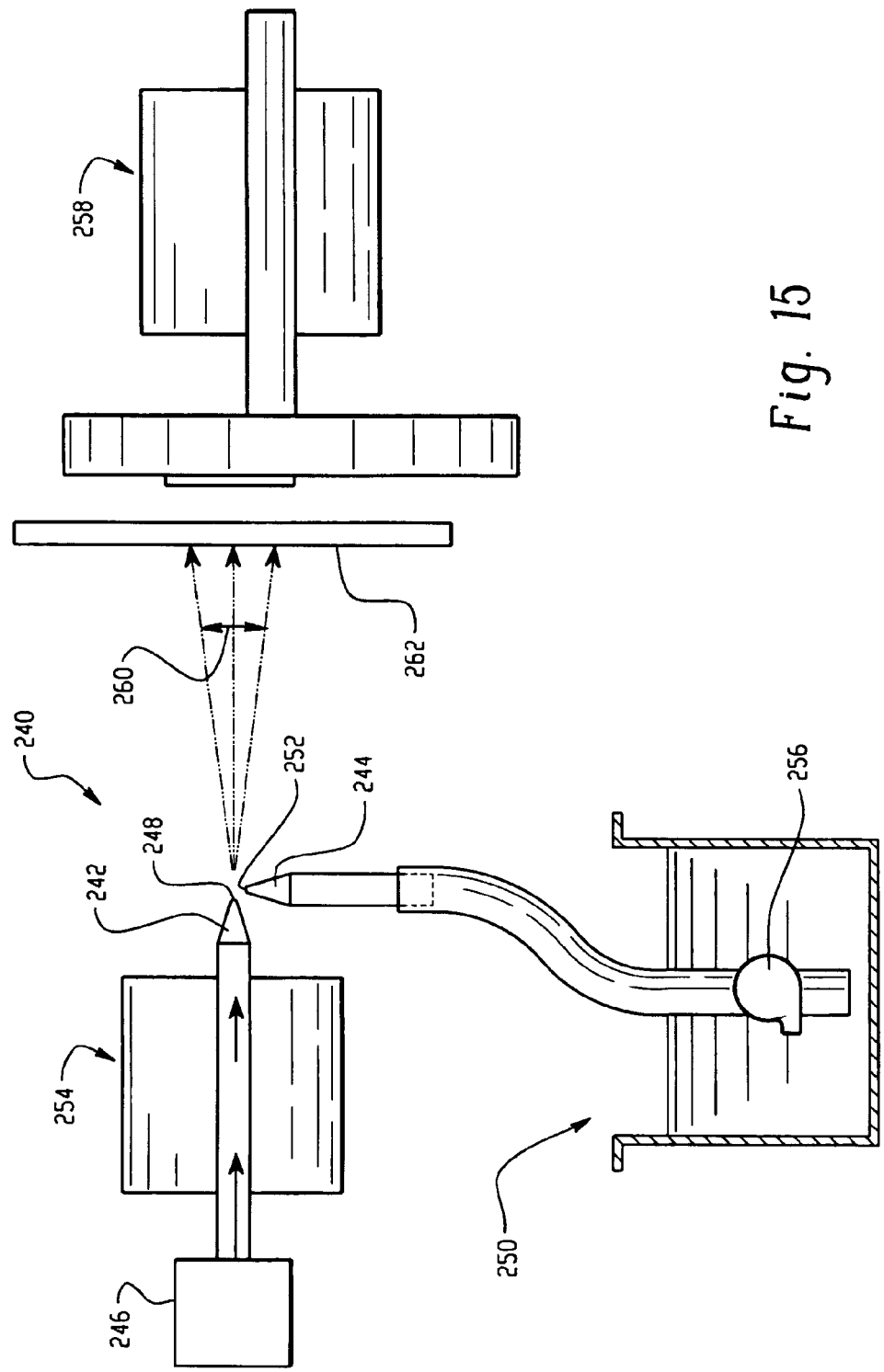
FIG. 15 is a schematic view of a micronebulizer for spraying sensing and reference membranes with multilayer structures onto different precise locations of a microprobe.

With reference to FIG. 15, a micronebulizer 240 is preferably used for spraying. The micronebulizer provides a spray or mist of the solvent and matrix material which can be designed such that the solvent evaporates as soon as the sprayed mist reaches the surface of the underlying membrane layer. Thus, even where the solvent for subsequent layers is the same, mixing of the two layers is largely avoided. In this way, the CA and CAP membranes do not substantially mix with each other.

As shown in FIG. 15, the micronebulizer 240 includes two nozzles 242, 244, formed from glass, or other suitable material. One of the nozzles 242 is connected with a source 246 of a carrier gas, such as nitrogen. The nitrogen nozzle has a reduced diameter tip with a gas outlet 248 at the distal end. The gas outlet 248 has a diameter of about 100-500µ, more preferably, about 300µ, located in a horizontal position, through which nitrogen gas is delivered under pressure towards a probe to be sprayed. The second nozzle 244 is connected with a source 250 of a polymer solution (such as is used for forming one of the layers—e.g., a mixture of CA and CAP). The second nozzle 244, has a reduced diameter tip with an outlet 252 at the end. The gas outlet 252 has a diameter of about 300µ or less, more preferably, about 100µ, located in a vertical position just beneath the tip of the nitrogen gas nozzle 242. Both of the nozzles 242, 244 are fixed to a 3 axis manipulator 254, which allows the precise adjustment of the tip positions. The flow from the gas nozzle 242 created a reduced pressure just inside the polymer solution nozzle 244, thereby drawing the polymer solution out of the nozzle and into the carrier gas stream. A pump is thus not necessary for delivering the polymer solution to the nozzle. In an alternative embodiment, a pump 256, gravity feed system, or the like delivers the polymer solution to the second nozzle 244, from where it is carried by the carrier gas toward the probe. The target sensing probe to be treated is preferably fixed to another 3 axis manipulator 258. This allows the probe to be moved to allow different areas to be coated (the angle of the spray 260 produced by the nozzles is relatively narrow). Optionally a mask 262 is used to allow some portions of the probe to be coated while others are left free of the coating layer.

The obtained CA/CAP double layer membrane 82, 84 is treated with a PBS buffer solution, e.g., by dipping in the solution. The PBS solution preferably contains a coupling reagent at a concentration of about 0.5-10 wt %, more preferably, about 2 wt % and subsequently a PBS solution containing the enzyme (and/or indicator dye, or other functionality) for immobilization on the CAP layer 84. The CA/enzyme- and/or indicator-loaded CAP membrane may be covered with several further functional, or protective layers by a serial combination of the micro-spraying and dipping methods described above.

The microspraying method described here is suitable for the microfabrication of several deferent kinds of membrane layers with different enzymes, ion-sensing materials, and blank (reference) membranes onto different precise locations of a single probe 10, 70, 110 by using masks analogous to those used in metal sputtering techniques.

The microspraying method makes it possible to construct complex structures of different multilayer membranes with precise control in all three dimensions: one along the depth of the membrane (series of different layers overlaying each other), and laterally (e.g., different sensor pads of precise shapes coated with the suitable membrane structure). This can be all done on the micrometer scale in all three dimensions, by using also suitable masks. Furthermore, analogous to routine microfabrication techniques, (that use photolithography, masks and serial metal sputtering), this spraying method can provide with cost effective ways of serial production of complex microsensors that include not only the base sensor elements but all the active and passive membrane coatings that are involved. This approach adds a new dimension to the already existing sensor microfabrication technologies: the capability of finely structuring membranes that need to be in the solution phase when deposited. It will be appreciated that other methods of deposition may alternatively be used, such as electrodeposition, electropolymerization, ink jet printing, and the like.

Figure 16:
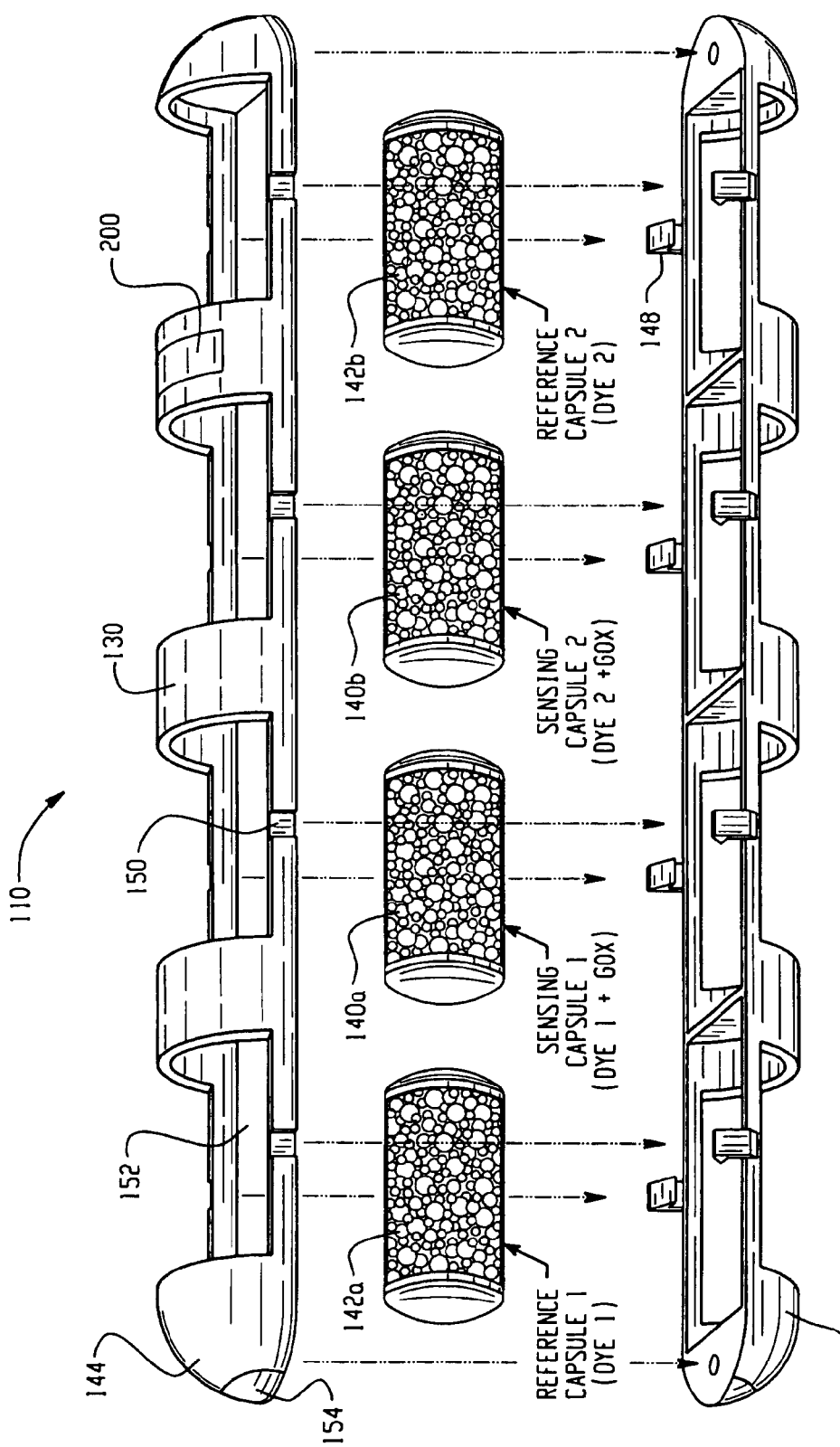
FIG. 16 is an exploded perspective view of another embodiment of an optical sensing probe including a sensing capsule array according to the present invention.

With reference now to FIGS. 16-18, another embodiment of an optical probe 110 is shown, which can be described as a "capsule array" type of probe. In this embodiment, the various detection substances and indicators are anchored to respective microscopic beads which are then separately contained in capsules or other suitable containment means. The containment means can provide layers which regulate the diffusion, exclusion, anti-blood clotting, and antimicrobial functions of the membrane layers described above and can be similarly formed.

The probe 110 of FIGS. 16-18 includes an elongated support body comprising a housing 130, formed from plastic, 2-hydroxyethyl methacrylate (HEMA) polymer; or other suitable material, which holds a plurality of sensing elements in the form of capsules 140a, 140b, together with reference sensing elements, also in the form of capsules 142a, 142b. The support body housing may be about 3000 µm in length and about 300 µm in diameter. The capsules 140, 142 may be about 500 µm in length and about 250 µm in diameter.

Each sensing capsule 140 may have a different sensitivity to the same analyte, e.g., glucose, or different capsules 140 may be sensitive to different analytes, in a similar manner to the sensing elements 40. In the embodiment of FIG. 16, the support body housing 130 takes the form of an elongate tubular element in which the capsules 140, 142 are axially aligned. The support body housing 130 is formed from upper and lower body portions 144, 146, which snap fit together to enclose a plurality of cylindrical capsules 140, 142. In particular, resiliently flexible tangs 148 on one of the body portions 146 engage corresponding slots 150 in the other body portion 144. Openings 152 in the upper and lower body portions 144, 146 provide access to the capsules from the ISF or other body fluid in which the probe 110 is situated. Optionally, the support body includes one or more magnetic portions 154, formed from stainless steel or other magnetic material. The magnetic portions allow the sensor probe 110 to be located and removed readily, when desired.

With particular reference to FIG. 18, each capsule 140 includes an outer membrane 158, which forms a part of a capsule housing 160. The housing 160 encloses a plurality of beads 162, 164, or other discrete particles, which will be generally referred to as beads. The beads may have an average diameter of about 0.5-100 µm, more preferably, about 1-20 µm, most preferably, about 1-5 µm. The beads act as supports for detection substances and indicators similar to those described for the embodiments of FIGS. 6, 8, and 12. The beads support detection substances, dyes, and the like, depending on the function of the capsule. The beads 162, 164, 166 are formed from a polymer or other support material suited to support of the particular active substance (e.g., dye and/or enzyme) carried by the support material. In a glucose sensing capsule, for example, some of the polymer beads 162, preferably formed from CAP or a CAP/CA mixture, are loaded with a first detection substance, such as an enzyme specific to glucose, GOX in the preferred embodiment. In an alternative embodiment, the beads comprise a CAP powder on which the dye/enzyme is supported.

A second set of polymer beads 164 in the capsule 140 is loaded with an optical sensing material, such as a dye. These "optical sensing" beads 164 may be formed, for example, from silica gel $C_{18}$ reversed phase (i.e., octadecylsilane-ODS) or PVC, covered with a pH sensitive optical liquid membrane or impregnated therewith. In one embodiment, the pH sensitive membrane or impregnated material includes one or more of a lipophilic hydrogen ion sensitive dye, an ionophore, and a lipophilic ion (preferably all three), examples of which are previously discussed.

A negatively charged hydrophilic gel 170 may surround the beads inside the capsule 140 to reject negative ions that otherwise tend to penetrate from the ISF into the capsule. This reduces the effect of pH buffering in ISF so as to increase the pH response per glucose molecule within the capsule. The concentration of the gel may be varied to sensitize a capsule for any given sub-range of glucose levels. Suitable hydrophilic gels include polyvinyl sulfate and polystyrenesulfonate.

Target analyte ions, such as $H^+$, $Na^+$, $K^+$, $Ca^{2+}$, and the sensitivities of the sensing capsule thereto may be precisely controlled and therefore optimized by changing the kinds of and/or concentrations of one or more of the lipophilic hydrogen ion sensitive dye, ionophore, lipophilic ion and the negatively charged hydrophilic gel 170 surrounding the beads, and the thickness of the capsule membrane.

A third set of beads 166 in the capsule 140 is optionally provided. The third set of beads 166, which may also be formed from CAP/CA, is loaded with a second detection substance, such as an enzyme specific for a product of the reaction of the first detection substance (GOX in the illustrated embodiment) with the glucose analyte, such as hydrogen peroxide. For example, the third set of beads 166 may be catalase-loaded CAP (or other polymer) beads. The catalase-loaded beads 166 entrapped in the capsule housing 160 decompose hydrogen peroxide formed by the enzymatic reaction of GOX with glucose and generate oxygen with the following reaction:

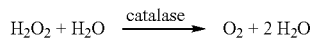

$$H_2O_2 + H_2O \xrightarrow{\text{catalase}} O_2 + 2\,H_2O$$

Because hydrogen peroxide is a strong oxidization reagent against proteins and organic molecules, the presence of catalase provides a longer lifetime for the sensing capsule 140. In addition, the generation of oxygen, which is again used as a co-enzyme of the GOX reaction, leads to an expansion of the glucose response range.

In the organic solvent at the surface of the optical pH sensing beads 164, ionophore for sodium, hydrogen ion sensitive chromoionophore and lipophilic anion are supported. GOX is similarly supported on the sensing beads 162. When the sensing capsule 140 is placed in the interstitial fluid, sodium and hydrogen ions in the interstitial fluid reach a distribution equilibrium with those in the organic solvent. When the glucose concentration in the interstitial fluid changes, the concentration of gloconic acid, which is produced by the enzymatic reaction changes; leading the change in pH inside the capsule. In this case, the shift of ion exchange equilibrium for hydrogen ion and sodium ions occurs between the organic solvent and aqueous solution inside the capsule, leading uptake or release of hydrogen ion into or out of the organic solvent. As a result, the concentration of the protonated chromoionophore changes in the organic solvent. Because the color of the protonated and unprotonated chromoionophore are different from each other, the change in the glucose concentration in the interstitial fluid leads to the color change of the optical ion sensing capsule.

The beads 162, 164, 166 can be surrounded by a negatively charged hydrophilic polymer gel 170. Suitable negatively charged hydrophilic polymer gels include potassium polyvinylsulfate and polyvinyl sulfonic acid. The negatively charged polymer gel inside the capsule 140 plays a role in the reduction of the phosphate buffer capacity on the basis of the Donnan exclusion concept, leading to improvement in sensitivity of pH change-based glucose detection. In one embodiment, the negatively charged polymer gel is present inside the capsule at a concentration of from about 5 to about 40% by weight, more preferably, about 10-30% by weight, and most preferably, about 20% by weight. For example, a negatively charged polymer gel present within the capsule at a concentration of 20 wt % allows for about 85% reduction in phosphate buffer capacity. The amount of polymer gel can be varied according to the desired sensitivity of the capsule. E.g., where high glucose concentrations are to be measured, lower levels of negatively charged polymer gel are employed, while for measuring relatively low glucose concentrations, higher levels of the gel are employed.

While the sensing capsule has been described with reference to three different types of beads, it is also contemplated that fewer or more types may be employed. For example, the detection substance (GOX) and dye may be loaded together on the same beads. Or components of the dye may be on different beads.

The reference capsules 142 may be similarly formed to the sensing capsules 140, with reference beads 172 formed without the detection substance (e.g., GOX).

The capsule membrane 158 is generally cylindrical and is closed off at either end by end caps 180, 182 to form the housing 160. The end caps 180, 182 may be formed, for example, from silicone rubber. A layer of celite 184, 186 may be used to seal the contents within the housing 160.

With particular reference to FIG. 18, the membrane 158 may have a multilayer structure. One or more of the layers may be formed from a 2-hydroxyethyl methacrylate (HEMA) polymer. In the embodiment of FIG. 18, the membrane has three layers 190, 192, 194. An outermost layer 190 (exposed to the ISF) is a protective layer, such as a layer of CAP-heparin about 2-3 micrometers (μ) in thickness. A middle layer 192 serves to regulate and limit the diffusion of glucose into the capsule 140. The middle layer 190 may be formed, for example, from polyurethane, polyvinylpyrrolidone, acrylic polyesters, vinyl resins, fluorocarbons, silicones, rubbers, HEMA, or combinations thereof, and be about 5-20μ in thickness, preferably, about 10μ. Polyurethane is particularly effective as in addition to slowing glucose diffusion relative to that of oxygen to a great extent, it also downgrades glucose levels to below the Michaelis Menten constant of the glucose-GOX system, rendering the overall response nearly linear.

An inner layer 194 is a negatively charged layer to reduce the efflux of gluconic acid from inside the capsule into the ISF. Gluconic acid is generated by the enzymatic reaction. This control leads to further improvement in glucose sensitivity due to the reduction in gluconic acid efflux from inside to outside the capsule via the negatively charge capsule membrane. The inner layer may be formed of a mixture of CA and CAP in a selected ratio, according to the desired sensitivity of the capsule, i.e., the glucose range to be detected. For example a ratio of about 1:1 by weight ratio may be suitable for in vivo measurements of glucose. Additional layers may be included in membrane 158, analogous to membrane layers 82, 84, 86, 88, 90, 92, 94, 96 used in the embodiment of FIG. 12.

The structure of the membrane permits control of the diffusion of the analyte species across the capsule membrane. This allows the sensitivity of the capsule to be controlled. For example, if low glucose concentrations are to be measured the capsule membrane and other aspects of the capsule are designed to be particularly sensitive. If high glucose concentrations are to be measured, a lower sensitivity is desired.

Sensitivity is adjustable in a number of ways. First, the functional hydrophilic gel entrapped inside the sensing capsule reduces the buffer capacity in vivo. Buffer capacity is the ability of the components of the sensor probe to buffer the pH of the medium. When the buffer capacity is high, more acid is required to lower the pH than is the case when the buffer capacity is low. As a consequence detection systems which are based on a change in pH become less sensitive. In the case of glucose detection for example, the conversion of glucose (a neutral molecule) to gluconic acid results in a pH change. Where there is a large buffering capacity, the pH change is minimized and the system is less sensitive (it takes more acid to achieve a certain pH change). Second, the composition of the membrane affects the diffusion of charged ions into the capsule. For example, phosphate ions from the ISF diffuse through the membrane, increasing the buffering capacity. If the diffusion rate is slowed by selection of membrane materials, the buffering capacity within the capsule can be maintained at a low level and sensitivity is increased. The diffusion rate, and hence sensitivity can be controlled, for example by changing the ratio of CA to CAP in the membrane. These two factors lead to a significant enhancement of the sensitivity of the probe 110.

Figure 19:
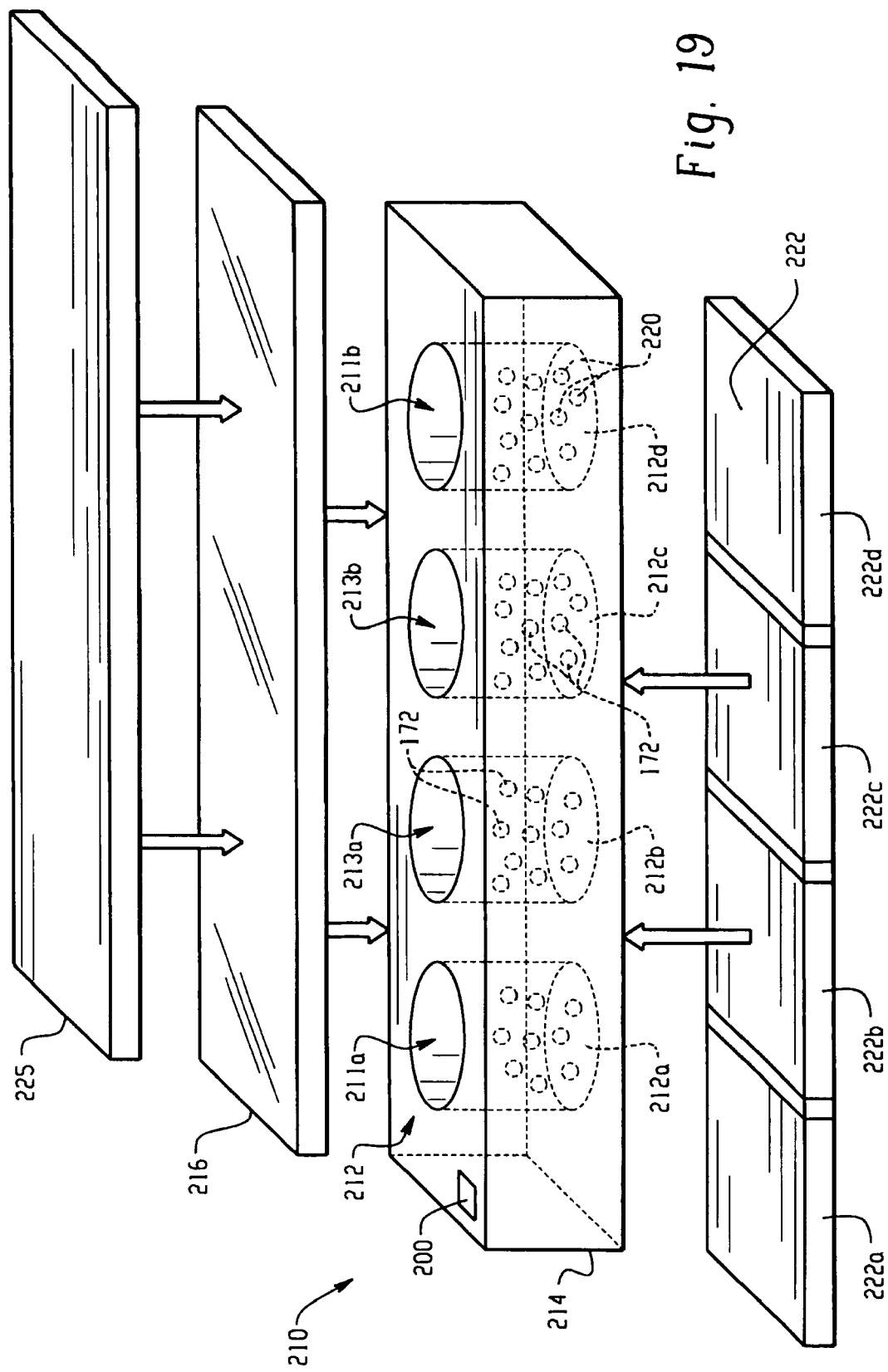
FIG. 19 is an exploded perspective view of an alternative embodiment of a sensor probe according to the present invention.

FIG. 19 shows another embodiment of a probe 210 with a plurality of sensing elements 211, a, b, c, etc. In place of the capsules of FIGS. 16-18, the sensing elements 211a,b and reference elements 213a,b include cavities or windows 212 (four in the illustrated embodiment) of a support body 214. The support body may be formed from a transparent material, such as quartz, a 2-hydroxyethyl methacrylate (HEMA) polymer, a silicone elastomer, or a CAP/CA plate, with the cavities being formed by molding or masking techniques. A transparent layer 216, such as a cellulose acetate and/or polyurethane membrane covers openings 218 to the cavities. The cavities 212 and layer 216 together serve as capsules 219, similar to capsules 140 of the prior embodiment. In the illustrated embodiment, the same membrane covers all the cavities, although it will be appreciated that different membranes can be used for the respective cavities. The cavities are filled with beads. For example, a first cavity 212a includes beads 162 and 164 (GOX-loaded polymer beads and polymer beads loaded with a pH sensitive optical liquid sensing cocktail). Cavities 212b and 212c include reference beads 172 (e.g., black and white, respectively or beads, formed without the detection substance (e.g., GOX). Cavity 212d includes sensing beads 220, for detecting another substance, such as potassium sensing beads.

The HEMA polymer comprises primarily 2-hydroxethyl methacrylate repeat units, although small amounts, generally less than about 10%, of other monomers may be present in the polymer.

Optionally a lower surface 222 of the sensor is opaque to aid viewing of the beads without interference from underlying skin color.

In an alternative embodiment, the sensor body maybe formed from a metal rod, such as stainless steel. The cavities in the rod may have white or mirrored bases.

A sensor probe 110, 210, 210 containing beads may be prepared in the following manner:

Formation of Polymer Beads

The polymer beads may be formed from a liquid mixture which is sprayed from a nebulizer, as described in greater detail below. For example a solvent, such as THF and/or bis(2-ethylhexyl) sebacate (BEHS) is mixed with polymer in liquid form, such as PVC or CAP/CA and sprayed into the air, resulting in a fine mist which rapidly dries. The dried "beads" which may have an average diameter of below 10μ, are then collected.

Figure 20:
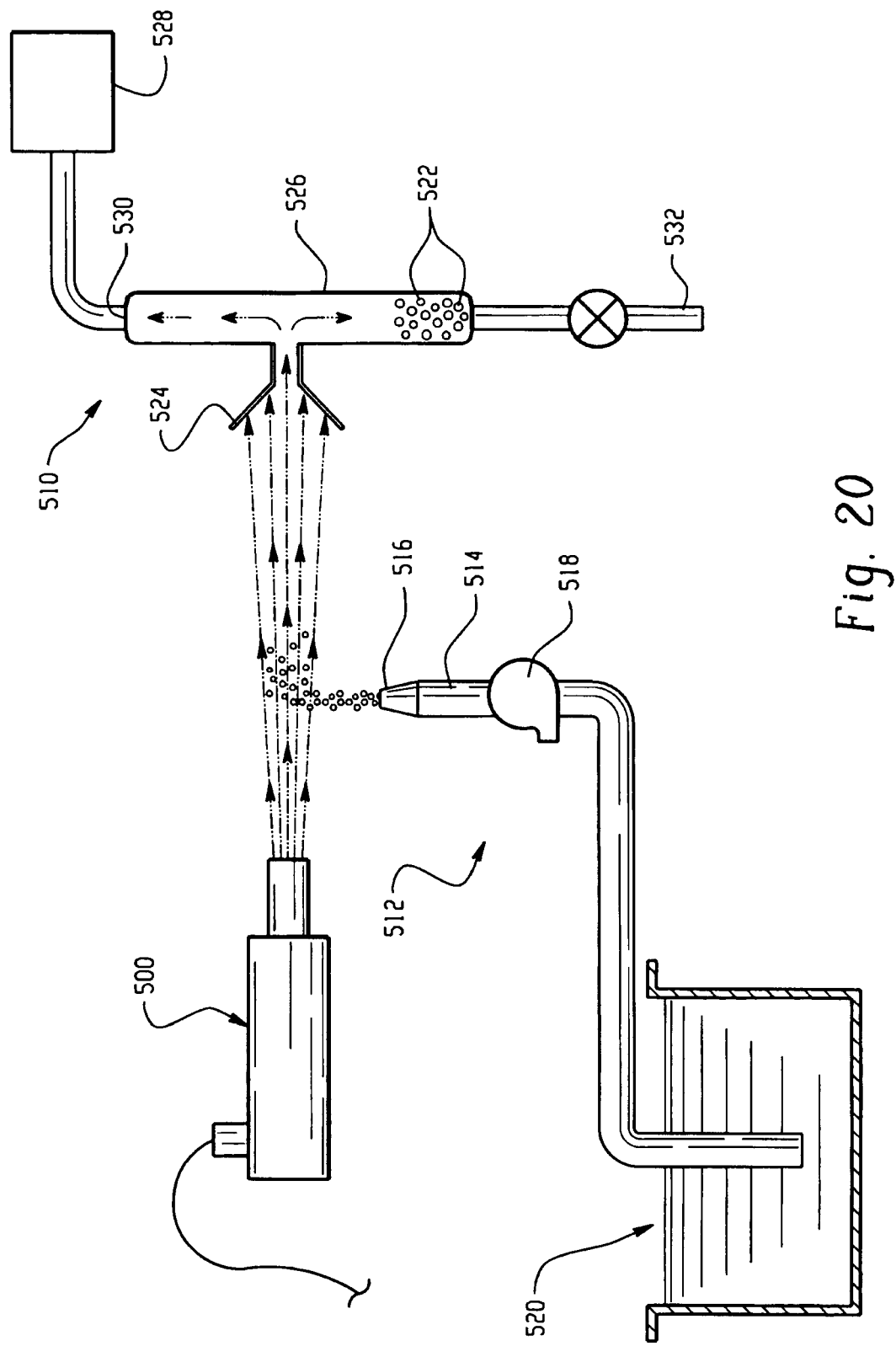
FIG. 20 is a schematic view of a micronebulizer system for forming polymer beads according to the invention.

A suitable nebulizer system is shown in FIG. 20. The system includes a source 500 of a heated gas flow, such as a heat gun. The heat gun delivers a stream of hot air towards a collection vessel 510. A nebulizer 512 includes a delivery tube 514 with a narrow outlet or nozzle 516, positioned just below the axis of the gas flow from the heat gun to deliver a spray of the liquid mixture into the stream of heated air. The delivery tube 514 may be a glass capillary with a nozzle 516 of about 50-500 μm in diameter. Optionally, a pump 518 delivers the liquid mixture from a suitable source 520, such as a container of the liquid mixture, to the outlet 516. Alternatively, gravity feed, and or wicking by the heated airstream are used. The spray enters the heated air stream approximately orthogonally and is carried in the stream to the collection vessel 510. In the course of the travel, the solvents rapidly evaporate and by the time the stream reaches the collection vessel, solid beads 522 have formed. The collection vessel 510 includes a conical inlet port or funnel 524 and a cyclone chamber 526, fluidly connected with the inlet port. The inlet port is aligned with the axis of flow of the heated air and thus the beads are carried in to the chamber. A vacuum system 528 such as a motor and fan assembly of a conventional hand held vacuum cleaner draws a vacuum on an upper outlet 530 of the cyclone chamber, to remove air from the chamber. The chamber and outlet are shaped and oriented such that the vacuum creates a cyclonic flow of air in the cyclone chamber. Specifically, the chamber 526 is funnel shaped, with its largest diameter closest to the inlet. In the cyclone chamber 526, the beads are rotated due to the cyclone air flow and pressed against the wall of the chamber by centrifugal force. This decreases the speed of the beads, which drop out of the airstream and are collected in a beaker or other suitable collection device mounted to the narrow, lower end of the chamber. One the desired quantity of beads has formed, a lower outlet 532 in the chamber 526 is opened, and the beads dropped out.

The beads formed by the nebulizer are generally in the range of 1-10 μm (at least 80% of the beads fall within this range), typically 1-μm. Other methods of forming the beads are also contemplated. For example, finely ground polymer powder can be used as the beads.

Formation of Sensing Beads

An enzyme is immobilized on polymer beads, which may be formed by the method described above. In one embodiment, the beads are formed from a THF solution (or other suitable solvent) containing CA and CAP in a ratio of about 2:1. In another embodiment, the beads are formed from CA or CAP/CA powder. The beads may be treated with a PBS solution (or other suitable solvent) containing EDC-HCl and washed with water or other suitable solvent. The beads are then contacted with a PBS solution containing the enzyme, e.g., GOX. The beads rinsed with a PBS solution and then dried in air, thereby forming the beads 162.

Formation of Optical pH Sensing Beads

Polymer beads, e.g., formed from ODS, PVC or CAP/CA may be formed by the method described above. In one embodiment, the beads are formed from a THF solution (or other suitable solvent) containing PVC and BEHS in approximately equal proportions. A pH sensitive solvent membrane cocktail is prepared containing a hydrogen ion-selective chromoionophore, a lipophilic anion-exchanger, an ionophore for sodium, potassium, and/or calcium ions, and a membrane solvent (e.g., BEHS or THF). The beads are added and then stirred, to form the optical pH sensing beads 164. Excess cocktail can be removed from the beads, thereby forming and the beads 164.

Formation of a Probe

For the probe 110, a polyurethane/CAP/CA tube 160 is prepared with about a 200μ diameter. The mixture of pH-sensitive ODS beads, GOX-loaded CAP powder or beads, and a negatively charged hydrophilic gel powder of potassium polyvinylsulfate (e.g., in a weight ratio of between about 1:1:0.1 and about 1:1:0.4) is packed into the tube 160. Both ends of the packed tube are sealed with a compatible material, such as celite 184, 186 and silicone glue 180, 182.

For the probe 210, a plate of cellulose acetate or other suitable material is formed of the desired thickness. The prepared CA plate is covered with a mask with suitable holes where the cavities are to be located in the sensor body. The cavities in the plate are then formed by drilling (e.g., with a laser), etching, or the like. A transparent layer 216 of about 5-50μ thickness (e.g., about 100□m) can be formed by solvent evaporation of a solution of CA, or the like. The layer is then adhered to one side of the sensor body, e.g., with a dichloromethane solvent.

In different cavities, sensing and reference elements are created by stuffing the cavities with sensing and reference beads, such as glucose sensing beads 162, 164; pH sensing beads 164; $K^+$ sensing beads; and optical white or black reference beads. Plates 222a, 222b, 222c, 222d (or a single, larger plate) formed from CA or the like are placed on each opening and adhered, e.g., with a small amount of THF solution containing cellulose acetate to close the cavities. A polyurethane coating 225 is then deposited on the sensing window 216 or over the entire probe.

Figure 21:
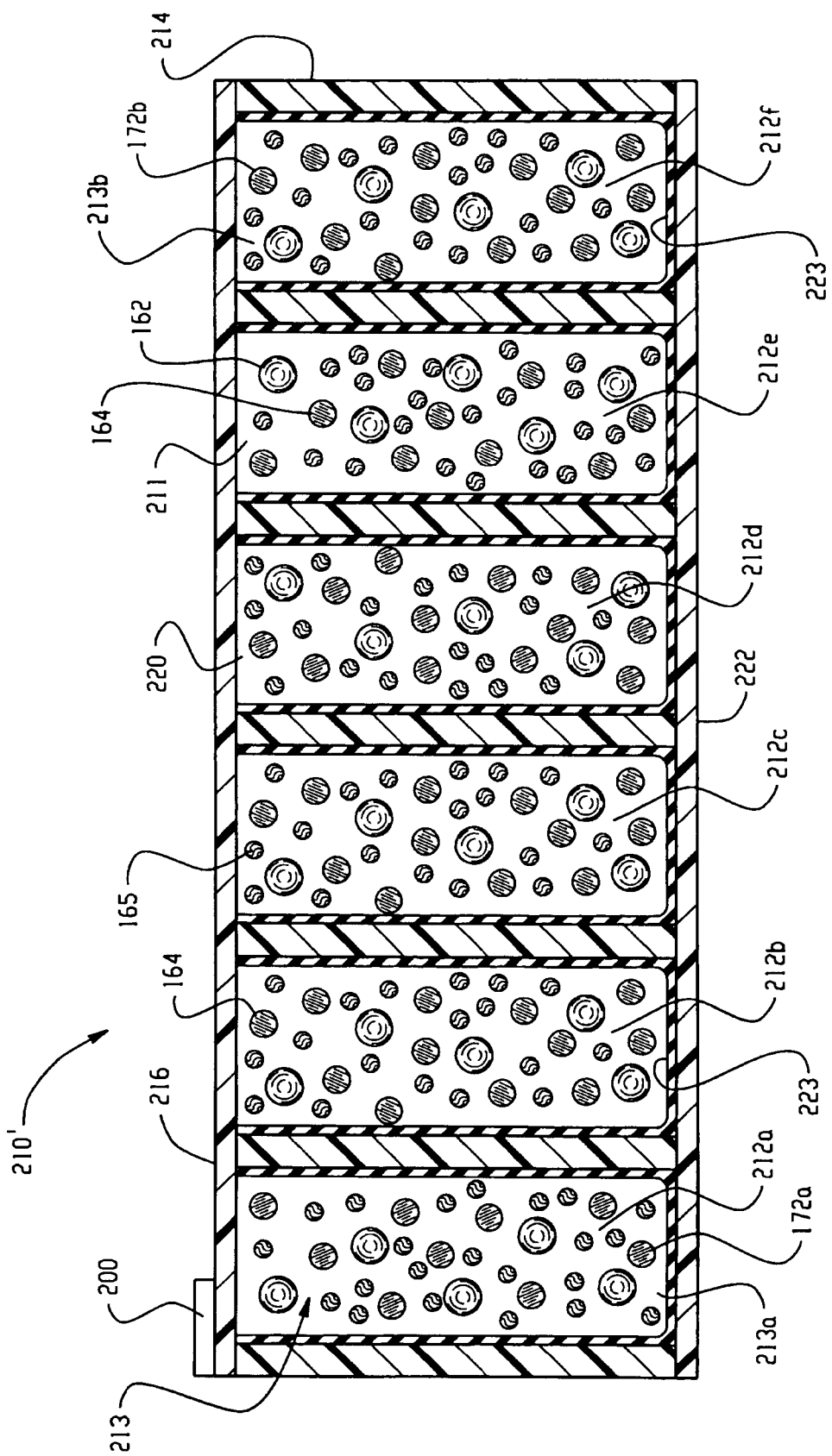
FIG. 21 is a side sectional view of another embodiment of a probe, according to the present invention.

In an alternative embodiment of a capsule array type sensor probe 210', illustrated in FIG. 21, a wax mold (not shown) is prepared using a mask. The wax mold is filled with a silicone elastomer which when set provides the sensor body 214. A cover layer, such as a polyurethane membrane 222 is applied to cover a lower opening to the windows 212a, b, c, etc. to form the cavities. The cavities are coated internally with a CA and CAP layer or layers 223.

In either embodiment, beads are then inserted into each window 212, according to the type of sensing element to be formed. The beads each have a different target analyte (e.g., glucose, potassium, and hydrogen ion) or reference (e.g., black and white colored material).

Once the cavities are filled, a transparent layer 216 is applied. This may be a layer of CAP/CA or other transparent material, such as silicone rubber and/or an agar gel, such as agarose, after filling with the beads.

The capsule/window-type optical glucose sensing element has several advantages, including the following:

1. Tuning/adjusting of glucose sensitivity is easily accomplished by changing the fixed negative charge density inside the capsule and/or in the inner layer of the capsule membrane.
2. Fabrication of reproducible probes is feasible simply by filling the bulk-prepared optical and enzyme beads 162, 164 into the respective capsules 140, 219.
3. The color intensity of the probe is significantly enhanced by diffuse reflectance and back-scattering of light because the size of the beads in the capsule is not significantly larger than the wavelength of light.
4. Extremely rapid optical responses are achieved due to the very thin layer (several microns) of the pH-sensitive optical membrane on the surface of the ODS beads.
5. This type of probe 110 can expand the number of the target analyte species by adding the corresponding optical sensing elements 140, 212 on a single probe.
6. The redundancy concept based on the color information coming from multiple sensing elements 140, 212 provides precise and reproducible monitoring both for glucose and electrolytes and may allow less frequent calibration.

On the basis of the optode technique, described above, simultaneous monitoring of vital electrolyte ions, such as $H^+$, $Na^+$, $K^+$ and $Ca^{2+}$ as well as glucose is also contemplated by using the corresponding ioniophore without enzyme.

Optionally, an optical or electrical temperature-sensing pad 200 (FIG. 16) is employed with any of the probes 10, 70, 110, 110' described above for detection of temperature. For example, a temperature sensor 200 based on a liquid crystal material, is mounted on the support body 130 or capsule housing 160 to correct the temperature effect on the monitoring. Alternatively, the temperature sensor may be microfabricated in the form of a capsule of similar shape to the capsules 140, 142 or windows 212.

An immunoassay sensing element (not shown) for the monitoring of drug molecules can be incorporated into the probe 70, 110, 210. A capsule 140, 219 is provided, but in place of the membrane 158, 216, a dialysis membrane, such as cellulose acetate, is used as the capsule membrane. Antibodies with large molecular weights are entrapped without immobilization inside the optical sensing capsule 140, 219 whereas small drug or antigen molecules can penetrate freely across the membrane. By entrapping a solution of an antibody for a target drug inside the sensing capsule together with optical beads which change color with binding of the antibody, in vivo drug (antigen) monitoring based on a compete antibody-antigen reaction is feasible.

In one application, a diabetic person can assess the glucose level in the ISF in real time and continuously by visually observing, e.g., with the naked eye, the changing color of the probe 10, 110, 210. Alternatively, as discussed for the layered sensors 10, the detector 12, e.g., in the form of a watch or pager-like device, includes a spectrophotometer (not shown) for automatically monitoring the color change. The detector also preferably includes a processing system (not shown), which includes a data storage module which communicates with the spectrometer and stores data and a look up table or algorithm for converting the spectrophotometric measurements to corresponding glucose levels. The processing system may provide feedback to an insulin pump (not shown).

Figure 22:
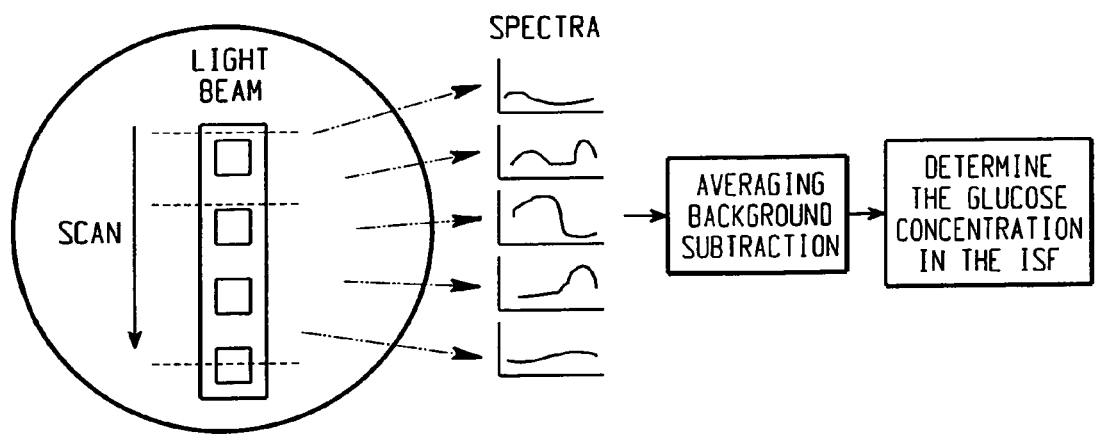
FIG. 22 illustrates a data processing scheme of a detector for a probe of FIG. 6.

In another embodiment, a color charge coupled device (CCD) camera automatically recognizes the components of the probe 10, 110, 120 such as sensing elements 40, 140, 211 and reference elements 42, 142, 213 via image processing. Background subtraction between the spectra of the GOX sensing elements 40, 140 and reference or blank sensing elements 42, 142 and ratiometric techniques, e.g., spectral shape recognition to identify "color", can be used for precise, quantitative glucose monitoring. For example, as shown in FIG. 22, a scanning device, such as a CCD camera or spectrophotometer, scans across the sensor probe 10, 110, registering the wavelength of light emitted by each of the sensing elements 40, 140, 213 and/or its intensity. Software in the computer processor 32 carries out subtraction of the background using information from the reference sensors 42, 142 and provides a measure of the glucose concentration (or other analyte). Preferably, the scanning device detects light emitted at two or more wavelengths, more preferably, at least three wavelengths, and most preferably, at least ten wavelengths within the range emitted/absorbed by the dye or other color-producing element. In this way, the software is able to recognize the shape of the wavelength distribution curve (a plot of intensity vs. wavelength) from the relationship between the intensities of the wavelengths detected, which is a constant for the particular color, and thus identify it with the color of the light being emitted/absorbed. This recognition of color, rather than intensity of the light from the sensing element, reduces the influence of variables, such as optical path length on the detection of the analyte. This system is particularly useful where there is a plurality of sensing elements, each one generating a color change at a different analyte concentration. The software then provides a simple yes/no detection for each sensing element, dependent on whether the color is generated, which is largely independent of optical path length and other factors affecting light intensity, such as the wavelength or intensity of the ambient light or other light incident on the sensing element. The number of sensing elements changing color can then be used as a measure of analyte concentration.

It will be appreciated that a micrometer-sized, highly-sensitive, and optionally multi-analyte probe 10, 70, 110, 210 of the type described, which has no need for physical connections, is not limited to in vivo diagnostics. For example, the probe is optionally used for research purposes or medical diagnostics by monitoring cells removed from a person. In one embodiment, simultaneous monitoring of efflux and/or influx of vital electrolytes and metabolites from and/or into cell(s) with a sensing plate(s) in which the optical sensing capsules are placed at given positions is one of the applications for a basic research purpose.

Figure 34:
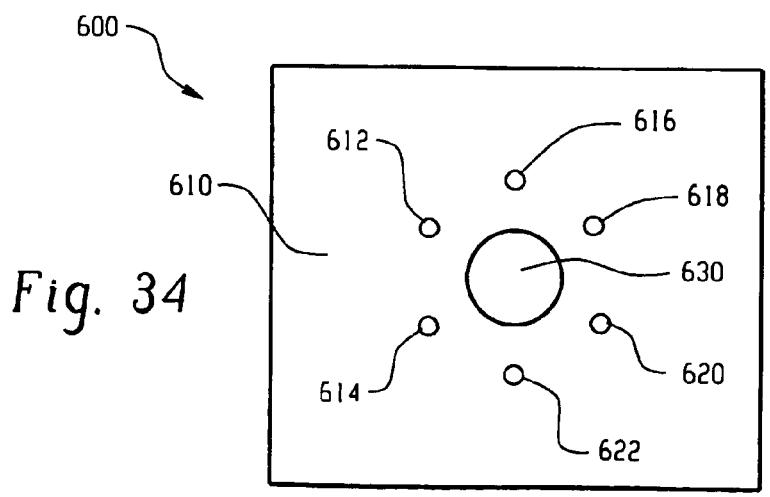
FIG. 34 shows the in vitro response of a glucose sensor.

For example, as shown in FIG. 34, an exemplary sensing system 600 is shown. The system includes a plate 610 in which capsules 612, 614, 616, 618, 620, 622 are embedded or otherwise formed. The capsules may be similarly formed to capsules 140 of FIG. 16, or may be formed in wells in the plate, similar to capsules 219 of FIG. 19. In the illustrated embodiment, a ring of sensing elements for potassium calcium, magnesium, sodium and hydrogen ions, as well as glucose, surround a site 630, to which a cell may be attached, such as a human or animal cell. Attachment is achieved at the site by making the site more hydrophilic than a surrounding area 632 of the plate surface 634. In one embodiment, the plate is formed from silicon with, an optional surface layer of silicon dioxide thereon. A layer of hydrophobic material, such as polyimide is laid down on the silicon/silicon dioxide and patterned, e.g., using conventional lithography techniques, to define the site 630 and optionally creating windows at the sensing element 612, 614, 616, 618, 620, 622 locations.

The probe 10, 70, 110, 210 may be used for environmental monitoring, such as for detection of analytes in effluent streams or in flowing bodies of water. The probe may be placed directly in the stream or flowing water. Alternatively, a portion of the liquid to be tested is withdrawn, for example using a bypass line, for detection in a separate vessel.

It will be appreciated, that in place of a detectable color change, the probe 10, 110, 210 optionally uses other detectable physical or chemical changes to track the concentration of an analyte. For example, the probe 10, 110, 210 uses other optically detectable properties, such as optical emission, e.g., fluorescence, phosphorescence, chemiluminescence, bioluminescence, or the like for detection of the analyte.

Other sensing methods are also contemplated. For example, a probe similar to probe 70 optionally uses an impedimetric/conductimetric base sensing scheme, or a piezocrystal based (electromechanical) scheme, or for sensing the analyte, a reaction-product, or a co-enzyme in the enzyme reaction.

Particularly where the probe 70 is deeply implanted, the probe or an associated device optionally includes a data storage unit 236 (FIG. 5). The data storage unit records and stores the data in digital form inside the patient's body, for later retrieval. Alternatively, wiring or the like (not shown) connects the deeply implanted probe with a transmitter unit (not shown) just under the skin. The transmitter unit allows powering and control of the deeply implanted probe 70, and communication with the probe in real time, without breaking the integrity of the skin as a protective barrier.

In the probes 10, 70, 110, 210 described above it is preferable to make diffusion of the analyte to the enzyme sites the rate-limiting step in the sensing process. This is generally the case when the concentration range to be covered overlaps with, or it is close to, the Michaelis-Menten constant ($K_M$) of the enzyme reaction. Rate limiting diffusion can render calibration linear or nearly linear in this case, or near linear (i.e., the sensitivity changes very little over the range of interest). When the value of the Michaelis-Menten constant is not clearly defined, rate limiting diffusion conditions are particularly advantageous. This is the case for GOX, where reported values of $K_M$ range from 5 mM to 25 mM, which is generally in the middle of the range of interest for glucose sensing. Analyte diffusion rate limitation can be achieved by adding a membrane, e.g., an outer or inner membrane, that has a diffusion coefficient far lower than the other membranes, gels, body fluids, or aqueous solutions employed in the sensing element. An outer polyurethane membrane is an effective membrane of this type and also serves to render the probe biocompatible.

In addition to providing a diffusion limiting membrane, one more co-enzymes may be provided in the sensing element 40, 72, 140 to facilitate the catalytic reaction. In the case of GOX, for example, the catalyzed reaction involves the co-enzyme oxygen. The co-enzyme is preferably present at the enzyme sites in excess as compared with the analyte to avoid the reaction scheme becoming co-enzyme-limited. When co-enzyme-limitation occurs, the probe effectively measures oxygen concentrations rather than glucose in the case of GOX. Such co-enzyme molecules generally reach the enzyme sites from "outside" the probe, i.e., from the surrounding interstitial fluid. Accordingly, the rate limiting membrane preferably provides for a higher diffusion of co-enzyme than the analyte.

For in vivo glucose monitoring, oxygen concentrations (co-enzyme) in the ISF are generally far lower (e.g, about 100-500 μM) than those of glucose levels (up to 50 mM). For accurate glucose measurements the oxygen co-enzyme is preferably present in excess to drive the catalytic reaction. Otherwise, some of the glucose is not being reacted to produce the hydrogen ion to trigger dye color change, and an inaccurate reading may result.

The oxygen excess is optionally achieved by generation of oxygen at the enzyme sites. For example, electrochemical oxygen generation or enzymatic recycling of oxygen is used to create an excess. Recycling of oxygen is generally not a complete solution due to diffusive losses. One electrochemical method employs mediators or "wired" enzyme electrodes which cause electrochemical oxidation of glucose, allowing the probe to be largely oxygen independent.

Another method involves preferential selection of oxygen by use of a hydrophobic membrane. Such membranes attract oxygen to the membrane surface while discouraging the approach of glucose. However, hydrophobic membranes may pose biocompatibility problems in some circumstances.

Particularly in the case of optical glucose probes 10, 110, 210, oxygen excess is preferably achieved using the ambient oxygen content of the fluid. A diffusion rate limiting-membrane, such as a layer of polyurethane 86 (see FIG. 11), is used to limit glucose diffusion far more severely than that of oxygen. Enzymatic regeneration of oxygen may also be used to increase oxygen levels, preferably in association with the diffusion rate limiting membrane 86. Enzymatic regeneration is most effective at low glucose levels, i.e., over a small fraction of the glucose concentration range of interest. For glucose monitoring, a polyurethane membrane is effective at facilitating oxygen diffusion, while reducing glucose diffusion. This preferential diffusion has been found to expand the useful, and nearly linear, range of optical glucose sensing to the entire glucose range of interest for in vitro measurements. For in vivo applications, which are generally dependent on the available oxygen supply in the ISF, additional membranes (e.g., polyurethane, polyvinylpyrrolidone, acrylic polyester, vinyl resin, fluorocarbons, silicone, rubber, or combinations thereof) may be employed to achieve increased sensitivity. In combination with oxygen recycling an effective range of glucose measurements can generally be made.

The probe 10, 70, 110, 210 has a variety of uses including in vivo monitoring for body fluid diagnostics; probes for other applications that may involve complex sample matrices to overcome the influence of complications with potentially interfering charged species, or agents that may damage the probe; detection of low sample concentrations; and the use of very small (miniature or microminiature, especially microfabricated, and MEMS based) probes, where high enzyme loading is advantageous. The multilayer structure of the probe can be perceived as a multifunctional, "intelligent" composite membrane for signal enhancement, interference mitigation, and probe protection from damaging effects of the sample(s), or the patient's body if the probe is implanted.

The probe 10, 70, 110, 210 is particularly effective for glucose measurements based on a suitable enzyme such as glucose oxidase (GOX). This enzyme is covalently attached to a CAP membrane via amide bonding by using a coupling reagent. This enzyme-loaded CAP membrane can be applied to both electrochemical and optical-based probes 10, 70, 110, 210. The CAP-enzyme membrane has a number of advantages over conventional immobilization systems including:

1. Enzyme loading with very high densities is feasible because the CAP is readily formed with large amounts of the phthalate group used for bonding with the enzyme (e.g., the CAP molecule may contain up to about 40 wt % of phthalate). Such a CAP-enzyme loaded membrane provides very high analyte sensitivities. For example, an amperometric-based glucose probe 70 with a GOX-loaded CAP membrane exhibits higher sensitivity per surface area to glucose than conventional immobilization systems: A sensitivity of at least 5 nA/mM, more preferably, about 7.5 nA/mM is readily achieved for a 100 μm diameter disc electrode.
2. High analyte permeability, which allows for a very short response time, is readily achieved. For a GOX-CAP membrane, the typical response time is within 20 seconds.
3. The CAP membrane is nontoxic, and has high biocompatibility. Thus, it is applicable for in vivo use, and is particularly useful for long-term implanted probes.
4. Chemical modifications of the CAP membrane are readily achieved. For example, it is possible to immobilize several kinds of enzymes and/or indicator dyes and other functionalities on one CAP membrane.

Figure 23:
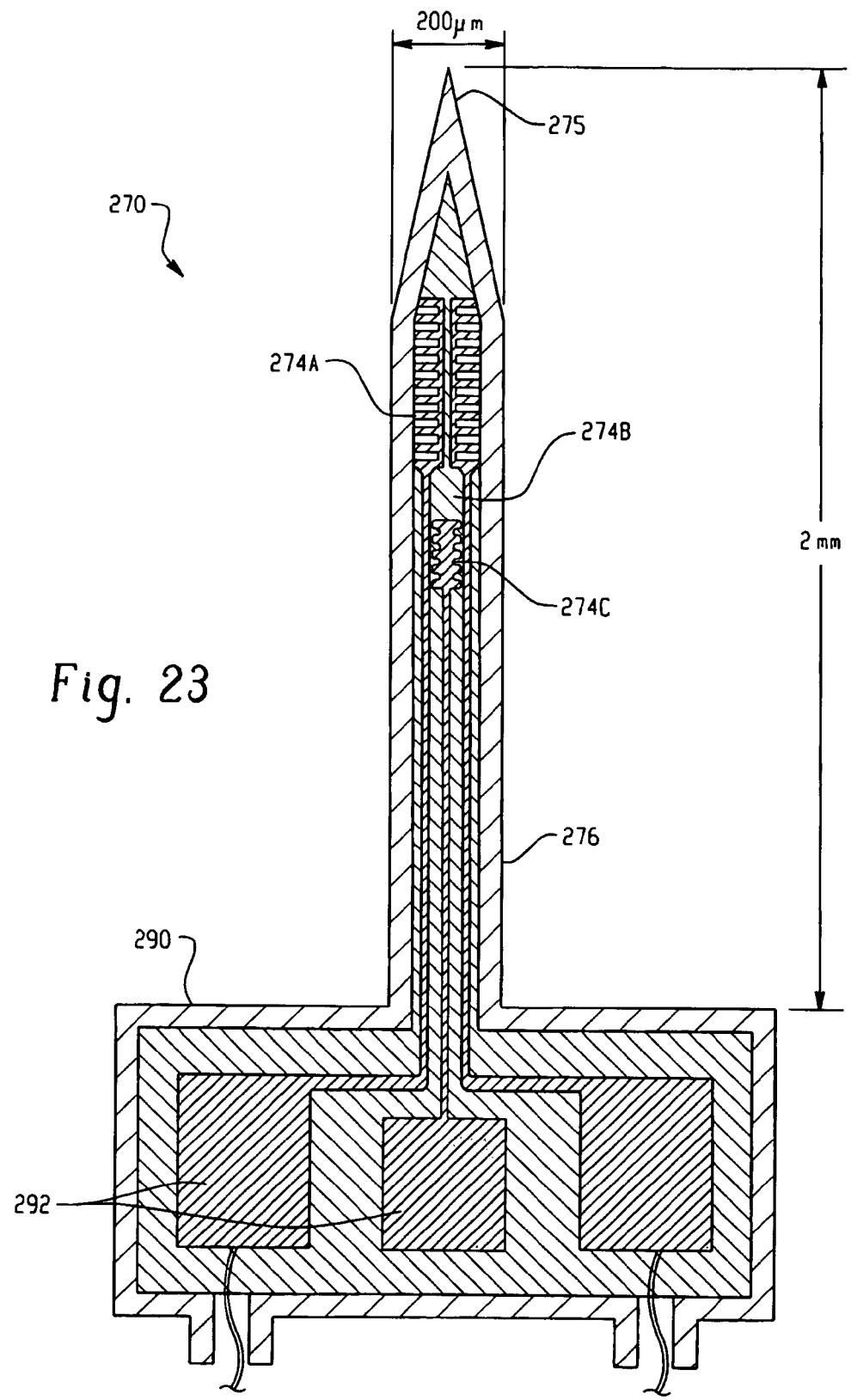
FIG. 23 is a side sectional view of an alternative embodiment of a sensing probe comprising a MEMS-made probe tip.

FIG. 23 shows an alternative embodiment of a probe 270 suitable for electrochemical monitoring. The probe includes a MEMS-fabricated tip 272 which has a plurality of sensing elements. The sensing elements of the tip may be formed by using standard microfabrication techniques. The MEMS tip 272 may be about 2 mm in length and about 200 μm in width, although smaller or larger tips are also contemplated. The MEMS device may be microfabricated for the in vivo monitoring of glucose and is shown in FIG. 23 as having three independent electrodes 274 A,B,C formed from Pt or other noble metal on one face 275 of a support body or substrate 276. A reference electrode (not shown) is formed on a rear face of the substrate 276. The MEMS made tip 272 is covered by a diffusion layer similar to layer 82 of FIG. 12, for example by dipping the entire tip in an acetone solution containing 1 wt % of CA and then drying in air to form a very thin diffusion layer.

Each Pt electrode 274 A,B,C is provided with different functions by coating the diffusion layer with different active layers. For example, masks for each electrode on the MEMS tip are prepared by using a photoresist technique. Using a mask and the micronebulizer 240 of FIG. 15, an immobilized enzyme layer is formed similar to layer 84 of FIG. 12. The enzyme layer is formed, for example, by spraying an acetone solution containing 1 wt % of CAP onto the diffusion layer. Due to the shape and position of an aperture in the mask, a thin CAP membrane (10 μm thickness) is thus formed only on Pt electrode 274A. The tiny nozzle outlets of the micronebulizer for dry nitrogen gas (e.g., diameter 300 μm) and for the polymer solution (e.g., diameter 100 μm) allow forming mists with ultra-small liquid particle size, which help the formation of a homogeneous, and very thin, membrane. The thus obtained, CA coated MEMS tip (with Pt electrode A coated also with CAP) is treated with a coupling reagent solution and following a GOX solution to immobilize the enzyme on the surface of the electrode 274A, as described for the embodiment of FIG. 12. In this case, the enzyme immobilization does not occur on the surfaces of electrodes 274B and C, and on the reference electrode, because they have no CAP membrane coating.

Using a second mask and the same micronebulizer 240, a second immobilized enzyme layer is applied, but this time to electrode 274B. In one embodiment, electrode 274B is provided with an inactive enzyme to act as a control. For example, a thin CAP membrane (10 μm thickness) is formed only on Pt electrode 274B using a second mask, which has an aperture sized and positioned to cover electrode 274B. The MEMS tip is then treated with a coupling reagent solution (which may be the same as that used for the active GOX enzyme) and inactivated GOX solution to form the reference membrane on the surface of electrode 274B.

Electrode 274C may be provided with an immobilized enzyme layer containing an enzyme different from that used on electrode 274A. The enzyme preferably acts on the same analyte as that of electrode 274A, although it is also contemplated that the enzyme used for electrode 274C is responsive to a second analyte. For example, a third mask has an aperture sized and positioned to cover electrode 274C. Using the third mask and the micronebulizer 240, a thin CAP membrane (10 μm thickness) is formed now selectively only on Pt electrode 274C. The entire MEMS tip is then treated with a coupling reagent solution (which may be the same or different from that used for electrodes 274A and 274B) and another kind of enzyme solution, such as glucose dehydrogenase, to form another kind of glucose sensing membrane on the surface of electrode 274C. The redundant data processing based on the signals coming from these three individual, different electrodes 274A, B, C allows for accurate and precise estimation of the concentration of glucose, e.g., in vivo.

After these steps, the entire probe tip is optionally covered with several kinds of protective membranes similar to those described for the probe of FIG. 12 by analogous spraying methods with the micronebulizer 240. Because nebulizing and spraying can be designed such that the solvent evaporates as soon as the sprayed mist reaches the surface of the underlayer, the different individual membrane layers do not substantially mix with each other. Thus, it is possible to use the same solvent (e.g., acetone) for each layer without risk of substantial intermixing.

As shown in FIG. 23, the probe tip 272 is integrally connected with a rectangular plate 290 which supports other components of the probe, such as contact elements 292 for connection with external wiring.

It is thus possible to construct complex structures of different multilayer membranes with precise control in all three dimensions: one along the depth of the membrane (series of different layers overlaying each other), and laterally (e.g., different probe pads of precise shapes coated with the suitable membrane structure). This can be all done on the micrometer scale in all three dimensions, by using suitable masks. Furthermore, analogous to routine microfabrication techniques (that use photolithography, masks, and serial metal sputtering), this spraying method can provide with cost effective ways of serial production of complex microprobes that include not only the base probe elements but all the active and passive membrane coatings that are necessary. This approach adds a new dimension to the already existing probe microfabrication technologies: the capability of finely structuring membranes that are in the solution phase when deposited.

In vivo sensing using electrochemical sensor probes 70, 270 described above may employ a percutaneous approach. For example, in the diabetes management area an insulin pump is often used by the diabetic for subcutaneous injections of insulin. In this case, an in vivo sensor probe may be part of the insulin delivery tubing and nozzle. The delivery tubing may be fabricated with an axo-parallel groove in its outer surface, in which optical communication cables (optical fibers or fiber bundles) and/or electrical wires can be housed. Such wires can communicate then with sensing elements close to the tip of the insulin delivery nozzle. A bore inside the tubing wall can also support communication cables. Introduction of sensor probes in such arrangements is easy since the tubing that is part of another device (like insulin pump) can be used as a mechanical support for penetration.

For percutaneous sensor probes which employ direct wiring (such as optical fibers and/or electrical wires) independent of any other percutaneous device (such as an insulin pump's delivery tubing), a similar arrangement can be designed as above, except that the wiring preferably has a tube-like outer support. If the support tubing is made from a highly rigid material (such as stainless steel or silicon) the percutaneous tubing for the probe tends to be prone to breakage and thus, spills and malfunctioning may occur. Inserting the sensing part like a needle into the body may be easier, however. Tubing, such as a relatively hard plastic tubing, or a plastic tubing with high compliance is thus preferred for the support tubing. In such cases, introducing the sensing part into the body to sufficient depth may be performed with a solid guiding tool, such as a hypodermic syringe to which its tip can be hooked. The guiding tool then can be removed.

By attaching (physically or chemically) the potentially hazardous molecules use for sensing to microbeads or entrapping them inside suitable beads reduces the likelihood that a potential spill of the contents of some of the sensing elements could pose health hazards. Spilled beads are easier to locate and remove. Also, the harmful capacity of most such immobilized molecules is reduced or eliminated by virtue of immobilization. Some, for example, need to partition into the cells' lipid membrane (like valinomycin) to pose a danger. This is clearly impossible when the molecules are not free to move (as when they are attached to the bead, even to an outer surface of the bead).

A further element of protection can be to entrap the beads behind a "window" inside a suitable cavity in the insulin delivery tubing. Such a window can be supported by a porous substrate with pore sizes smaller than the beads. The pores would make it also easier to fill the cavity with the necessary components via the communication channel by letting the air to be displaced escape through the pores.

The sensing elements may be deposited inside the cavity through the communication channel in liquid/gel form by precise consecutive injections. However, the entire sensing assembly may be made also with all the necessary structures like membrane structures ready, and then advanced into the cavity as a whole through the channel (like a piston). This would also use the pores for air escape before the advancing "piston," which can also include the entire communication "wiring" as well.

The pores may be made with nanotechnology in fact so small that no elements of the body's defense mechanism can enter them. This could provide in a simple way for reduced or entirely eliminated adverse reactions in vivo without the need for complicated outer membrane chemistries. A polyurethane or similar outer coating can be easily cast on top of the porous window in case this is still needed for better biocompatibility. Multichannel communication can make use of redundancies also in percutaneous sensor probes where the sensing part can then consist of layers of different selectivities and functions.

Theoretical Considerations

In the glucose/GOX reaction:

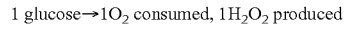

$$1 \text{ glucose} \rightarrow 1 O_2 \text{ consumed}, 1 H_2O_2 \text{ produced}$$

For an electrochemical system, at the positive electrode, $H_2O_2$ oxidizes, at negative electrode, $O_2$ reduces to $H_2O_2$, at very negative potentials, both reduce to $OH^-$.

The current is largely independent of glucose concentration, since $H_2O_2$ generation increases it while $O_2$ depletion decreases it. This is for equal stoichiometry; in reality 2× more current is generated by $O_2$ than by $H_2O_2$ at that voltage.

The same currents can be obtained from the reference electrode (coated with denatured enzyme). Subtractions of the respective currents between the two electrodes gives signals due to glucose only. Changes in the reference I+ and I− track metal surface area changes; this can be used to update sensitivity for the enzyme electrode for I+ and I−. This takes care of ambient $O_2$ and $H_2O_2$ changes also (which can occur in vivo, and can be simulated in vitro). Stationary sensor surfaces can be achieved by use of a pulsing protocol. The correlated changes in I+ and I− are thus indicative of surface area changes, the non-correlated ones indicate ambient $O_2$ and $H_2O_2$ changes. A proof is obtained from I−− (the non-correlated changes show up differently than the correlate ones due to the 1:2 ratio of electron generation by $H_2O_2$ versus $O_2$).

The difference between I−− of the reference and the real enzyme electrode should preferably be almost zero, but not exactly zero due to asymmetry in $O_2$ and $H_2O_2$ diffusion (one across the GOX membrane losing some activity, the other generated there). This can be used to track changes in the membrane structure, including GOX activity since $O_2$ has higher sensitivity (2×) than $H_2O_2$ at E−−.

These are optimized for steady state currents taken with sufficient pauses between them. If the pause is very short then Cottrellian depletion can be used for selection: a quick switch from E+ to E−− will find $H_2O_2$ already depleted but $O_2$ not, thus I−− will be for a while sensing more $O_2$ than $H_2O_2$ (more than 2× relative sensitivity for $O_2$). Switch from E− to E−− will find $O_2$ depleted but $H_2O_2$ not, so relative sensitivity for $H_2O_2$ is enhanced (larger than ½ of that of $O_2$).

In summary, therefore, the invention has a variety of applications. In one aspect, a sensor system includes a probe capable of continuous or intermittent in vivo monitoring of a biochemical species. In a more limited aspect of this aspect, the biochemical species is selected from the group consisting of glucose, lactate ions, electrolytes, and combinations thereof.

In another aspect, a sliver type autonomous includes a plurality of microminiature sensing elements for the simultaneous in vivo monitoring of one or more biochemical species.

In yet another aspect, a probe for monitoring one or more analyte species includes a plurality of micro sensing capsules. Each capsule includes a membrane. A medium and a functional hydrophilic gel are entrapped inside the membrane. The medium may be a color changing medium, enzyme loaded medium, or antibody loaded medium. The capsule membrane preferably has a multilayer structure. In a more limited aspect, the probe is powered by one or more of a battery and electrical inductance. In another more limited aspect, the probe employs an optical sensing scheme, such as a color change of an absorption dye, an emission by a fluorescent dye, or a combination thereof, which may operate without an electrical power source. In yet another more limited aspect, the probe is controlled by short electromagnetic waves. In yet another more limited aspect, the detector employs one or more of amperometric detection; optical detection; potentiometric detection; optical emission, such as fluorescence, phosphorescence, chemiluminescence, or bioluminescence; impedimetric/conductimetric detection; and piezocrystal (electromechanical) detection.

In another aspect, a probe system includes a multilayer membrane comprising a layer of cellulose acetate and a layer of cellulose acetate phthalate. The multilayer membrane may further comprise one or more of an enzyme and an indicator dye. In a more limited aspect, the multilayer membrane contains one or more of the enzyme glucose oxidase for glucose, lactase for lactose, galactose oxidase for galactose, urate oxidase for uric acid, and creatinine amidhydrogenase for creatinine.

In another aspect, a method of producing a multilayer membrane includes contacting an electrode substrate with a first solution containing a matrix material, such as cellulose acetate to form a first layer. The electrode substrate is contacted with a second solution, such as a solution containing cellulose acetate phthalate, to form a second layer. A compound to be immobilized, such as an enzyme or an indicator dye, is deposited on the second layer. The probe thus formed may be provided with additional protective layers, comprising one or more of a positively charged cellulose, negatively charged cellulose, chitosan, CAP-heparin, chitosan-heparin, a polyurethane, polyvinyl pyrrolidone, an acrylic polyester, a fluorocarbon, and a silicone rubber.

In this way, "intelligent" membrane structures can be created, consisting of a number of overlaid membranes, each performing different tasks. Such tasks include diffusion, enzyme reaction, dye based optical detection, exclusion of charged interferences, exclusion of other damaging agents, and provision of biocompatibility.

In another aspect, a fabrication method of such multilayer structures is provided. A micronebulizer is employed to spray coat one or more of the layers of the membrane. Microfabrication and MEMS technologies may be employed to form a probe. Full three dimensional control of membrane fabrication at high precision is possible with this method.

In another aspect, a glucose biosensor based on a suitable enzyme such as glucose oxidase (GOX) is provided. This enzyme is covalently attached to a CAP membrane via amide bonding by using a coupling reagent. This enzyme-loaded CAP membrane can be applied to both electrochemical and optical-based biosensors.

In another aspect, a multilayer structure, based on a combination of CA, CAP, or other matrices, to perform a number of different "tasks" is provided. The first layer in direct contact with an electrode or optical guide is a diffuse layer for products, and eventual co-enzyme(s) (e.g., oxygen) of the enzyme reaction(s). The next layer may be based on CAP, and can be used to immobilize an enzyme at high density (high enzyme loading). For multi-analyte monitoring, more than one enzyme may be immobilized on this CAP layer. In more limited aspects, optical dyes, or enzyme(s) and dye(s), or other functionalities are immobilized on the same layer. The CA/enzyme- and/or indicator-loaded CAP membrane may be covered with several further functional, or protective layers, such as positively charged cellulose, negatively charged cellulose, chitosan, CAP-heparin, chitosan-heparin, polyurethane, polyvinyl pyrrolidone, acrylic polyester, fluorocarbons, silicone rubber, and the like by the suitable serial combination of micro-spraying and dipping methods. The positively charged cellulose layer and the negatively charged cellulose layer act as protective membranes to prevent electrochemical or other interference from positively charged and negatively charged species such as heavy metal ions, cathecol amines and ascorbates, respectively. The CAP-heparin layer is a protective membrane to prevent thrombus formation, meant for in vivo applications. Polyurethane, polyvinyl pyrrolidone, acrylic polyester, or fluorocarbons-based protective layers may further improve the biocompatibility of the multilayer membrane structure, and thus, the entire sensor. Also these layers may control the diffusion of substrate(s) (target analyte(s)), leading to the improvement of linearity and dynamic range of the sensor responses. A thus prepared CAP-based enzyme membrane with multiple layer structure can be used as an active membrane for in vivo diagnostics, and even for implantable sensors for long-term continuous monitoring of substrate-concentration levels such as glucose, urea, creatinin and the like, with high sensitivities, good biocompatibility, and exceptionally low background signals.

Without intending to limit the scope of the invention, the following examples demonstrate methods of preparation and use of probes.

EXAMPLES

Example 1

Preparation of a Sliver-Type Glucose Probe

An optical glucose probe of the type shown in FIG. 8 is prepared as follows: A strip-shaped plastic plate 44 is covered with a CAP/CA membrane by a dipping method or spraying method. For example, 10 μl of acetone solution containing 0.5 wt % of CA and 0.5 wt % of CAP is applied to a plastic plate and then allowed to stand until the acetone is evaporated. The resulting membrane is about 10μ in thickness. The membrane is treated with 1 ml of PBS solution containing 5 wt % of 1-ethyl-3-[3-(dimethylamino)propyl]carbodiimide hydrochloride (ECD-HCl) and 5 wt % of N-hydroxysuccinimide (NHS). It is then treated with a PBS solution containing 2 wt % of GOX and 0.5 wt % of a pH indicator dye (neutral red or congo red). The membrane is covered with a poly(acrylate) gel layer prepared by radical co-polymerization of sodium acrylate (10 wt %) and N,N'-methylenebis(acrylamide) (0.2 wt %). The acrylate layer is covered with a chitosan/heparin membrane.

Example 2

Preparation of a Sliver-Type Glucose Probe

Figure 24:
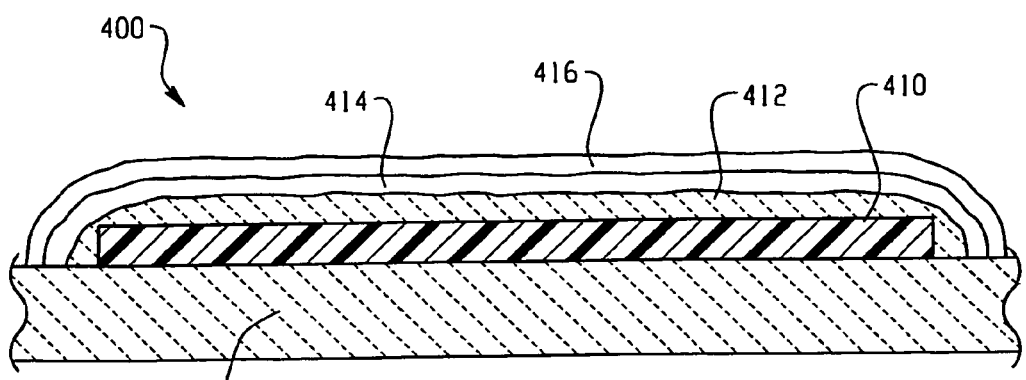
FIG. 24 is a side sectional view of an alternative embodiment of a sensing element.

An optical glucose probe 400 as shown schematically in FIG. 24 is prepared as follows: A pH sensitive solvent polymeric membrane cocktail is prepared with a tetrahydrofuran (THF) solution containing 50 mg of poly-vinyl chloride (PVC), 100 mg of a membrane solvent (e.g., 2-nitrophenyl octyl ether), 0.5 mg of a hydrogen ion-selective chromoionophore (e.g., chromoionophore II (ETH 5350, 9-(diethylamino)-5-[(2-octyldecyl)imino]benzo[a]phenoxazine), 0.5 mg of a lipophilic anion-exchanger (e.g., KTpClPB (potassium tetrakis(4-chlorophenyl)borate)), and 5.6 mg of a potassium ionophore, (e.g., bis(benzo-15-crown-5) ($K^+$ ionophore, bis[(benzo-15-crown-5)-4'-methyl]pimelate)). This cocktail is cast on a strip-shaped glass plate 44 and dried to form a first layer 410. The PVC membrane 410 thus obtained is covered with a CAP/CA membrane by the spraying method. The CAP/CA membrane is treated with a PBS solution containing ECD-HCl (5 wt %) and NHS (5 wt %). The membrane is then treated with a PBS solution containing 1 wt % of GOX. The membrane is covered with a polyacrylate gel layer 414 prepared by radical co-polymerization of sodium acrylate and N,N'-methylenebis(acrylamide. To form the polyacrylate gel layer, 100 μl of aqueous solution containing 100 mg of sodium acrylate, 20 mg of N,N'-methylenebis(acrylamide) and 2 mg of VA-044 (thermal radical, 2,2'-azobis[2-(2-imidazolin-2-yl)propane]dihydrochloride) is applied on the surface of the PVC membrane. Then it is heated at 40° C. for 30 min). The polyacrylate layer is covered with a chitosan/heparin membrane 416.

Example 3

Preparation of a Capsule-Type Glucose Probe

A glucose probe of the type shown in FIG. 16 is prepared as follows: A pH sensitive solvent membrane cocktail containing a hydrogen ion-selective chromoionophore (chromoionophore III, 1.6 mg of a lipophilic anion-exchanger (NaHFPB), 22 mg of a sodium ionophore (bis(12-crown-4) ($Na^+$ ionophore, bis[(12-crown-4)methyl]2-dodecyl-2-methylmalonate), and 100 mg of a membrane solvent (dioctyl sebacate) is prepared. Into 50 mg of the pH-sensitive membrane cocktail, 100 mg of ODS beads (average diameter: 25 μm) are added and then stirred. CAP powder is treated with EDC-HCl and then NHS. After washing the ECD-treated CAP powder with water, the powder is treated with a PBS solution containing GOX. The powder is rinsed with a PBS solution and then dried in air. A polyurethane/CAP/CA tube 160 is prepared with 200 μm diameter. The outermost layer 190 of the tube is made of polyurethane with about 10 μm thickness and the inner layer 194 (about 10 μm thickness) is made of a mixture of CA and CAP (1:1 weight ratio). The mixture of pH-sensitive ODS beads, GOX-loaded CAP powder and a powder of potassium polyvinylsulfate (1:1:0.1 weight ratio) is stuffed into the tube. Both ends of the stuffed tube are sealed with celite 184 and silicone glue 180.

Example 4

Preparation of a Window-Type Glucose Probe

A probe 210 of the type shown in FIG. 21 is prepared as follows: A positive mold is made of silicone rubber for a microminiature sensing probe body by hand cutting or with a lithography technique. Melted paraffin wax is cast into this positive mold to prepare a negative mold. Transparent silicone elastomer or polyurethane is cast into the negative mold and cured to form the sensor body 214.

The prepared sensor body 214 made of silicon rubber, (dimension 2 mm long and 250μ width, 100μ thickness) has, 6 penetrated holes (windows) 212, 150μ square. The thus fabricated sensing probe body is placed on a polyurethane membrane 222 and attached thereto by using chloroform to define a lower surface of the sensor. Preferably, the polyurethane membrane is melted slightly and used to cover the surface of the sensor body. As a result, one side of the windows 212 in the sensing probe body 214 is covered with a thin polyurethane film. A THF solution containing 1 wt % of CA and CAP is applied into the windows of the sensing probe body and then allowed to evaporate to form a thin layer 223. A low melting point agar gel containing sensing or reference beads 162, 164, 166 is packed into each of the windows 212. For window 212a, ODS beads 172a are used as a white reference. For window 212b, pH-sensitive ODS beads 164 are used for pH sensing. The beads for window 212b are formed by preparing a cocktail of 0.5 mg of chromionophore III, 1.6 mg of NaHFPB, 5 mg of bis(12-crown-4) and 100 mg of dioctyl sebacate. Into 50 mg of the pH-sensitive membrane cocktail, 100 mg of ODS beads are added and then stirred.

For window 212c, $Na^+$-sensitive ODS beads 165 are used for $Na^+$ sensing. The beads for window 3 are prepared by forming a cocktail of 0.5 mg of chromionophore III, 1.6 mg of NaHFPB, 22 mg of bis(12-crown-4) and 100 mg of dioctyl sebacate. Into 50 mg of the pH-sensitive membrane cocktail, 100 mg of ODS beads are added and then stirred.

For window 212d, $K^+$-sensitive ODS beads 220 are used for $K^+$ sensing. The beads for window 212d are prepared by forming a cocktail of 0.5 mg of chromionophore III, 0.5 mg of KTpClPB, 5.6 mg of bis(benzo-15-crown-5) and 100 mg of dioctyl sebacate. Into 50 mg of the pH-sensitive membrane cocktail, 100 mg of ODS beads are added and then stirred.

For window 212e, pH-sensitive ODS beads 164 (i.e., the same beads as for window 212b) plus GOX-loaded CAP powder or beads 162 are used for glucose sensing. Catalase-loaded CAP powder is also present in window 212e for reduce hydrogen peroxide generated by GOX-glucose enzymatic reaction and to recover the oxygen concentration which is used as a co-enzyme of GOX-glucose enzymatic reaction.

For window 212f, graphite powder is used as a black reference 172b. The other side of the windows in the sensing probe body 214 is sealed with agar gel and then thin silicone rubber to form layer 218, and is cured.

Example 4

Preparation of a Layer-Type Glucose Probe

A probe 10 is prepared similar to that shown in FIG. 11. A first layer (adjacent the substrate 44) is a sensing membrane 60 which is based on a PVC supported pH-sensitive liquid membrane disk (5 mm diameter, about 0.1 mm thickness).

The membrane layer 60 is covered with a GOX/BSA (bovine albumin)/glutaraldehyde membrane 62 (about 0.1 mm thickness) and a polyurethane membrane 66 (about 20 μm thickness). Layer 64 is omitted.

The composition of the pH-sensitive liquid membrane 60 is 0.5 wt % of chromoionophore III (9-(diethylamino)-5-[(2-octyldecyl)imino]benzo[a]phenoxazine), 7.0 wt % of a potassium ionophore (2-dodecyl-2-methyl-1,3-propanediyl bis[N-(5'-nitro(benzo-15-crown-5)-4'-yl]carbamate), 0.5 wt % of KTpClPB (potassium tetrakis(4-chlorophenyl)borate), 64.9 wt % of BEHS and 27.1 wt % of PVC. The membrane composition is optimized to obtain the maximum change in its color ranging from pH 5.5 to 7.5 in the presence of 4.0 mM potassium ion.

Example 5

Preparation of a Capsule-Type Glucose Probe

Sensing capsules are prepared similar to those described in Example 3. The capsules have a tube-shaped with the dimension of 200 μm diameter and 500 μm length, in which GOX-immobilized CAP beads and pH-sensitive liquid membrane-coated ODS beads are entrapped. The pH-sensitive liquid membrane contains 0.8 wt % of chromoionophore III, 16.2 wt % of sodium ionophore (bis[(12-crown-4)methyl]-2-dodecyl-2-methylmalonate), 2.6 wt % of NaHFPB, and 80.4 wt % of BEHS. The capsule membrane has a double layer structure. The outer layer 190 is made of polyurethane of about 10 μm thickness and the inner layer 194 is formed from CA and is about 10 μm in thickness. Layer 192 is omitted.

Example 6

In Vitro Responses of a Layer-Type Glucose Probe

Figure 25:
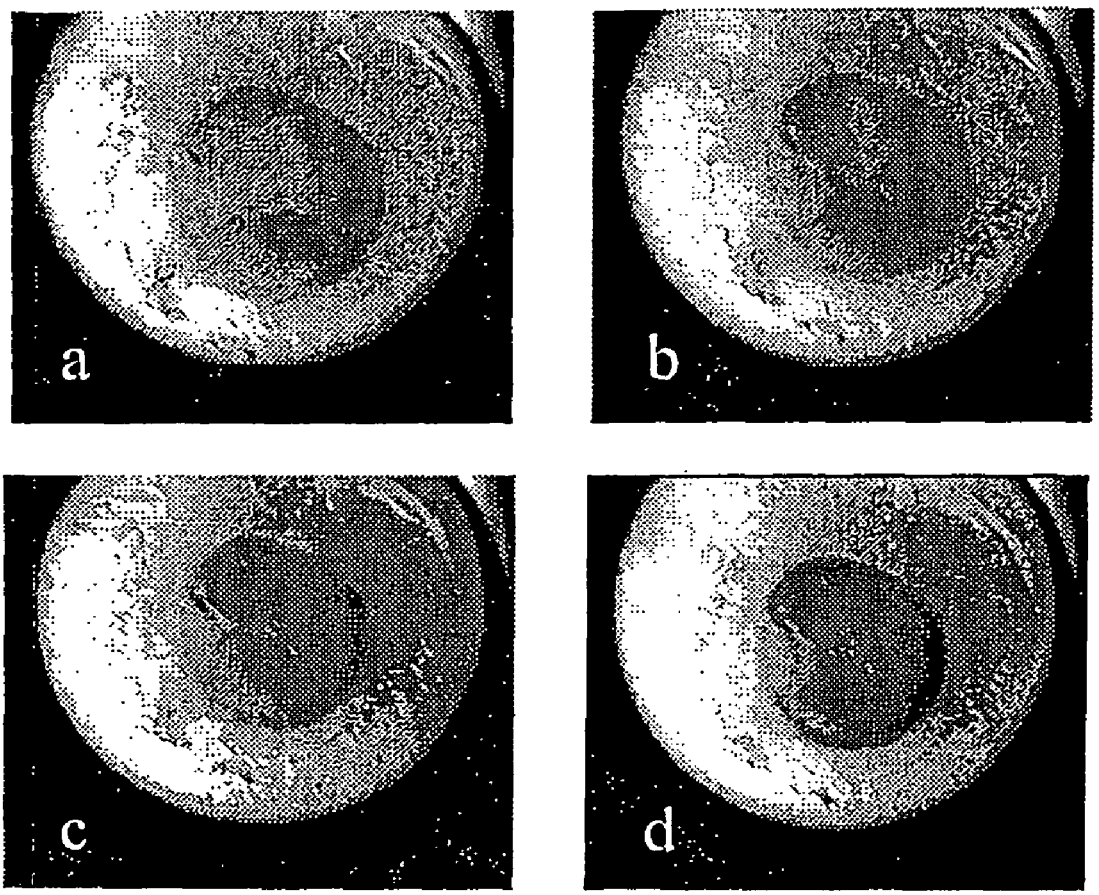
FIGS. 25a, 25b, 25c, and 25d are images of the sensing element of FIG. 24 in phosphate buffered saline (PBS) buffer solution containing no glucose (FIG. 25a), 39.0 mg/dL glucose (FIG. 25b), 95.0 mg/dL glucose (FIG. 25c) and 666.6 mg/dL glucose (FIG. 24d)
Figure 26:
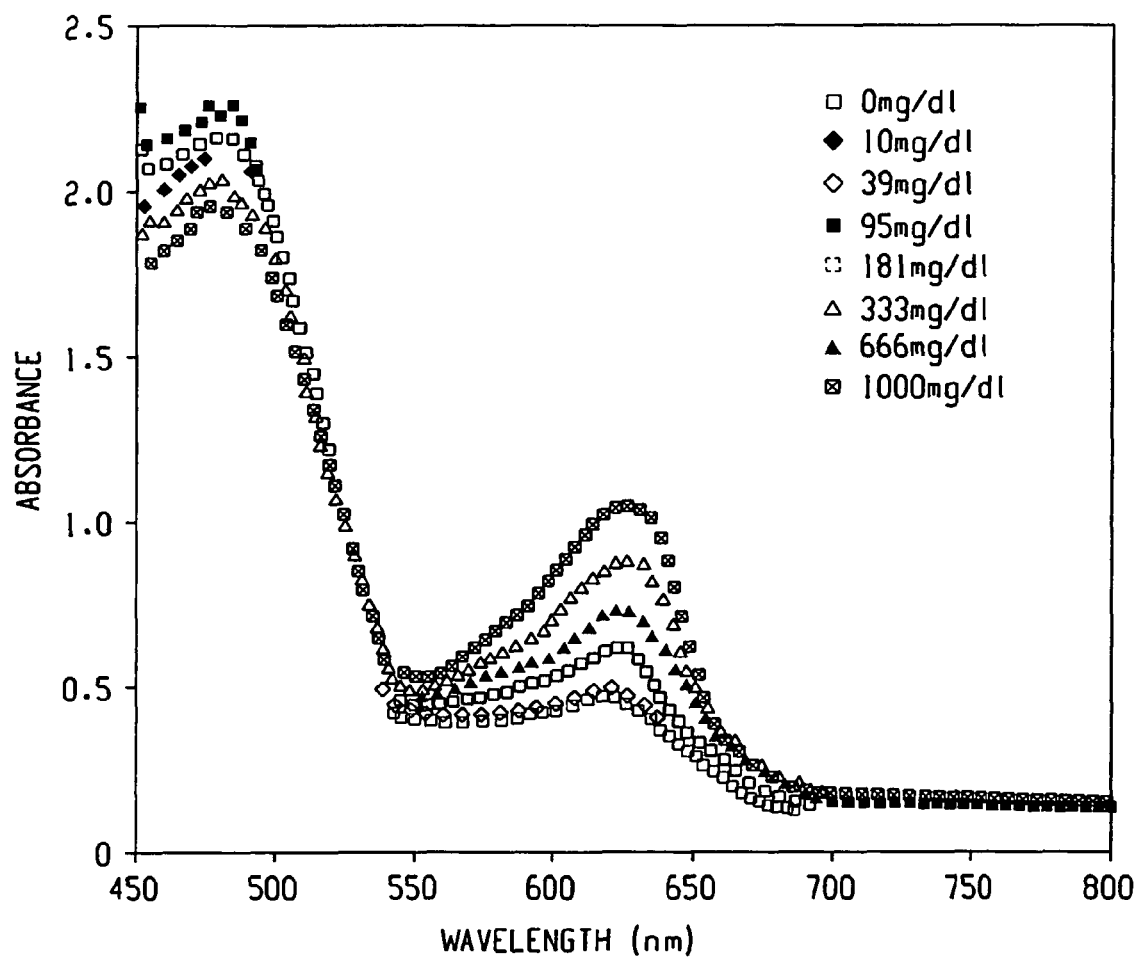
FIG. 26 is a plot showing absorption spectra of the optical sensing membrane of FIG. 24 in a PBS buffer solution at various concentrations of glucose from 0-1000 mg/dl.

Millimeter-sized type glucose optical sensing membranes were fabricated as described in Example 4. FIG. 25 shows images of the thus prepared optical sensing probe 10 in a PBS solution containing various concentrations of glucose. Significant change in the membrane color was observed from orange to bright green with increasing concentrations of glucose (FIGS. 25a-25d). Corresponding absorption spectra of the optical sensing probe measured by a diode array-based spectral probe (Zeiss, MMS-1) equipped with a microscope are shown in FIG. 26. It can be seen that the absorbance at the peak of 625 nm wavelength, which can be attributed to the protonated form of chromoionophore III, increases with increasing concentration of glucose in the PBS buffer solution. In addition, the absorbance at 480 nm wavelength assigned to the unprotonated form of chromoionophore III decreases successively with increasing concentration of glucose. This result clearly indicates that the local pH at the surface of the pH-sensitive optical membrane 60 decreased with increasing glucose concentration, reflecting the increasing concentration of gluconic acid generated by the enzymatic reaction in the GOX-loaded membrane.

Figure 27:
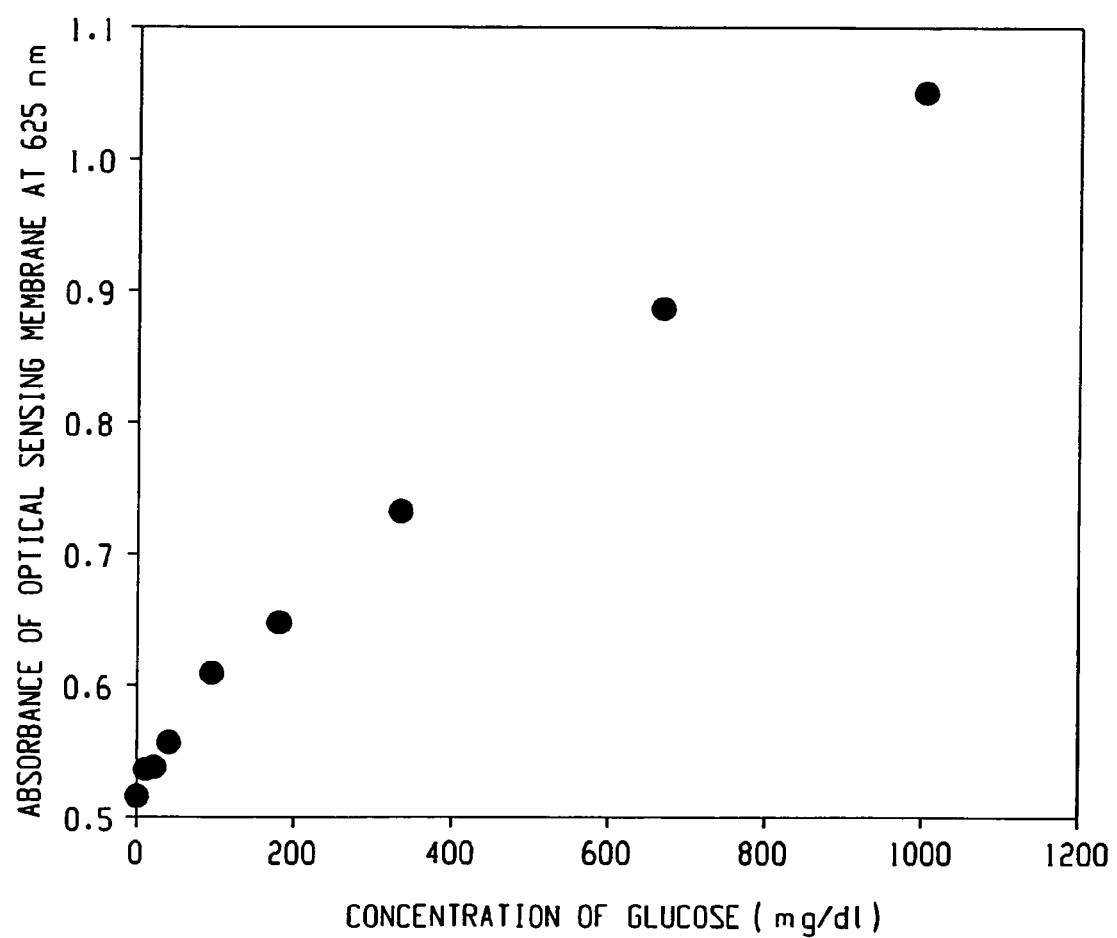
FIG. 27 is a plot of absorbance vs. concentration, illustrating the response of the optical sensing membrane of FIG. 24 to glucose in a PBS buffer solution.

FIG. 27 shows the relationship between the absorbance of the optical sensing membrane at 625 nm and the glucose concentration in the PBS buffer solution. The optical response was observed from 10 mg/dL to 1000 mg/dL of glucose concentration, where all clinical concentrations in ISF are covered. It can be concluded that the prepared glucose optical sensing membrane 60 is feasible as a sensing element of the sliver-type glucose optical probe 10.

Example 7

In Vitro Responses of a Capsule Array-Type Glucose Probe

Optical glucose sensing capsules of the type shown in FIGS. 16-18, were microfabricated as described in Example 5. The optical response properties of the capsules to glucose in PBS buffer solution was observed by using a color CCD camera.

Figure 28:
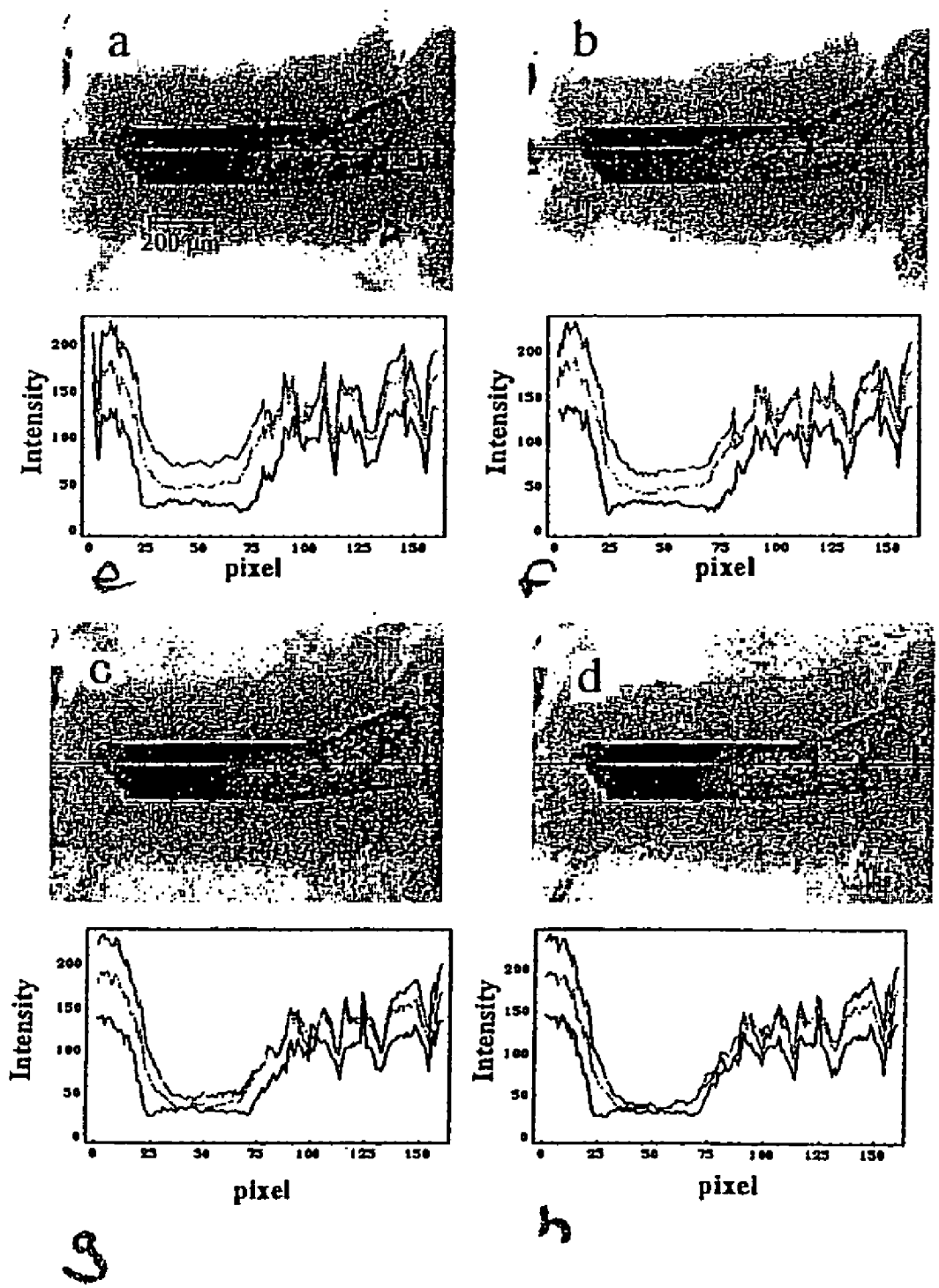
FIG. 28 is a plot showing RGB color responses of the optical sensing capsule of FIG. 16 to glucose in the PBS buffer solution.

FIG. 28 shows the images of the thus prepared sensing capsule in the PBS buffer solution containing various concentrations of glucose together with the red, green and blue color intensities at each pixel on the red line in the corresponding image. FIGS. 28a, 28b, 28c, and 28d are images the optical sensing capsule containing no glucose (FIG. 28a), 77.0 mg/dL glucose (FIG. 28b), 182.0 mg/dL glucose (FIG. 28c), 305.0 mg/dL of glucose (FIG. 28d), and FIGS. 28e, 28f, 28g, and 28h are plots of red, green, and blue color intensities at each pixel on the red line in the corresponding images. It can be seen that the color of the sensing capsule changes from dark orange to dark blue with increasing concentration of glucose, reflected by the decrease in the red color intensity in the corresponding images.

Figure 29:
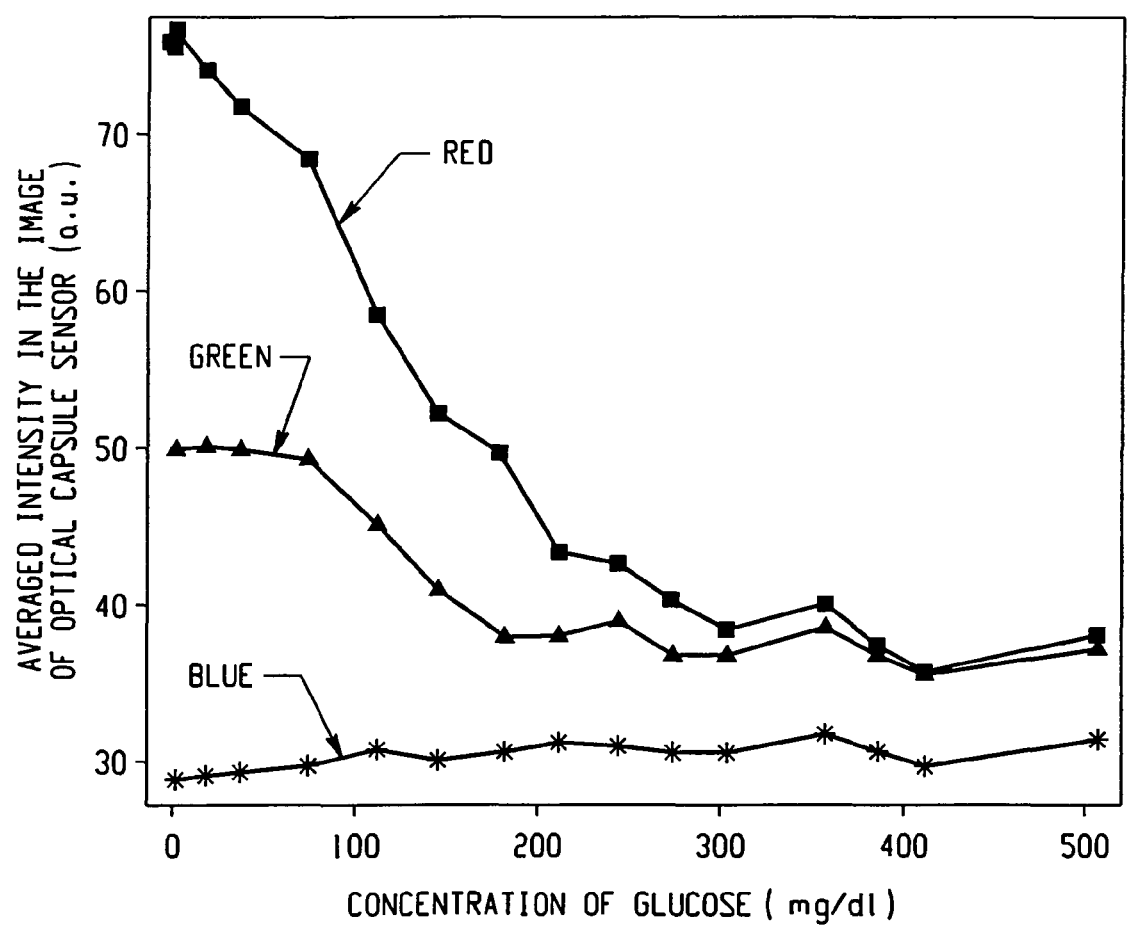
FIG. 29 is a plot of average intensity of the image taken by a CCD camera of a capsule of FIG. 16 with varying glucose concentration for green, red, and blue portions of the spectrum.

The relationship between the concentration of glucose in the PBS buffer solution and the averaged RGB color intensities of the pixels corresponding to the sensing capsule is shown in FIG. 29. It can be seen that the intensities of the red and also green color decrease with increasing concentration of glucose whereas the blue color intensity increases slightly. These changes in the RBG color intensities are consistent with the corresponding spectra changes observed for the layer-type membranes with the same chromoionophore (see FIG. 28). This successful change in color of the sensing capsule for glucose in the clinical concentration range in the PBS buffer solution demonstrates not only the feasibility of this tiny sensing capsule as an element for an optical glucose probe but also the usefulness of a color CCD camera as a detector 12 of the probe 10, 110, 210.

Example 8

Preparation of Layer-Type Enzyme-Loaded CAP Based Probes with a Multiple Layer Structure for Electrochemical Sensing A GOX-based membrane with eight individual layers on the surface of a Pt electrode was prepared as shown in FIG. 12. The Pt disk electrode has a diameter of 100 μm. The Pt disk electrode is dipped into an acetone solution containing 1 wt % of CA for 10 seconds, picked up and then air-dried in room temperature. A first layer 82 is an inner diffusion layer in which the products of the enzyme reaction as well as small molecules in the biological fluid such as hydrogen peroxide, proton, and oxygen diffuse freely. The membrane 82 thickness is around 5 μM.

An acetone/methanol solution (10/1 wt/wt) containing 0.8 wt % of CA and 0.2 wt % of CAP is sprayed onto the surface of the first CA layer by using the micronebulizer of FIG. 15 for 30 seconds to form layer 84. The diameters of the nozzle tips of the micronebulizer for the dry nitrogen gas and the solution are 300 μm and 100 μm, respectively. The flow rate of the nitrogen gas is around 1.5 L/min. The thickness of the thus obtained CA/CAP layer is around 10 μm. After air-drying for 30 min, the electrode is immersed in a PBS buffer solution (pH 7.4) containing 1 wt % of a coupling reagent, N-(3-dimethylaminopropyl)-N'-ethylcarbodiimide hydrochloride (ECD.HCl) and allowed to stand for 2 hours in a refrigerator (about 4° C.). After that, the electrode is rinsed with a small portion of the PBS buffer solution several times to remove the excess coupling reagent. Immediately after this step the electrode is dipped in a PBS buffer solution containing 2 wt % of GOX and allowed to stand for 12 hours in a refrigerator (about 4° C.). The microelectrode is rinsed again with the PBS buffer solution to remove the unbonded enzyme, and then air-dried in the room temperature, resulting in the second layer 84 of the formula shown in FIG. 9.

A chloroform solution containing 1 wt % of polyurethane is sprayed on the surface of the second layer for 10 seconds and then air-dried. The thickness of this third layer 86 is around 5 μm. An acetone solution containing 1 wt % of CAP-EDA (ethylenediamine) is sprayed on the surface of the third layer for 15 seconds and then air-dried. The thickness of this fourth layer 88 (see FIGS. 12, 13) is around 5 μm. An acetone solution containing 0.5 wt % of CA is sprayed on the surface of the fourth layer for 10 seconds and then air-dried. The thickness of this fifth layer 90 is around 2 μm. An acetone solution containing 1 wt % of CAP is sprayed on the surface of the fifth layer for 15 seconds and then air-dried. The thickness of this sixth layer 92 is around 5 μm. An acetone solution containing 0.5 wt % of CA is sprayed on the surface of the sixth layer for 10 seconds and then air-dried. The thickness of this seventh layer 94 is around 2 μm. An acetone solution containing 1 wt % of CAP-EDA/heparin is sprayed on the surface of the seventh layer for 15 seconds and then air-dried. The thickness of this eighth layer (FIGS. 12, 14) is around 5 μm.

Example 9

Preparation of a Probe for Electrochemical Measurements Using a Micro-Spraying Method in Combination with Dip Coating A MEMS tip 272 as illustrated in FIG. 23 is prepared with several independent working electrodes 274A,B,C by using standard microfabrication techniques. The MEMS device is microfabricated for the use of in vivo monitoring of glucose and has three independent Pt electrodes 274 A,B,C on one side. A reference electrode of silver/silver chloride (not shown) is formed on a rear side of the substrate 276. This MEMS made tip is dipped in an acetone solution containing 1 wt % of CA and dried in air to form a very thin diffusion layer. Masks for each electrode on the MEMS tip were prepared by using a photoresist technique. Using a first mask, and the micronebulizer of FIG. 15, with an acetone solution containing 1 wt % of CAP, a thin CAP membrane (10 μm thickness) is formed only on Pt electrode 274A. The tiny nozzle outlets of the micronebulizer for dry nitrogen gas (diameter 300 μm) and for the polymer solution (diameter 100 μm) allow forming mists with ultra-small liquid particle size, which help the formation of a homogeneous, and very thin, membrane. The thus obtained, CA coated MEMS tip (with Pt electrode A coated also with CAP) is treated with a coupling reagent, solution (ECD-HCl) and following a GOX solution to immobilize the enzyme on the surface of the electrode 274A. In this case, the enzyme immobilization does not occur on the surfaces of electrodes B, C, and on the reference electrode, because they have no CAP membrane coating.

Using a second mask and the micronebulizer 240, a thin CAP membrane (10 μm thickness) is now formed only on Pt electrode 274B. The MEMS tip is then treated with a coupling reagent solution and inactivated GOX solution to form the reference membrane on the surface of electrode 274B. Using a third mask and the micronebulizer 240, a thin CAP membrane (10 μm thickness) can be formed now selectively only on Pt electrode 274C. The entire MEMS tip 272 is then treated with a coupling reagent solution and another kind of enzyme solution, such as glucose dehydrogenase, to form another kind of glucose sensing membrane on the surface of electrode 274C. The redundant data processing based on the signals coming from these three individual, different electrodes 72A, B, C allows for accurate and precise estimation of the concentration of glucose, e.g., in vivo.

After these steps, the entire probe tip 272 is optionally covered with several kinds of protective membranes with multilayer structures (see, e.g., Example 8 above), by analogous spraying methods with the micronebulizer 240. Because nebulizing and spraying can be designed such that the solvent evaporates as soon as the sprayed mist reaches the surface of the underlayer, the different individual membrane layers do not appreciably mix with each other.

Example 10

Preparation of a Capsule Array-Type Sensor Probe a) Preparation of Glucose Sensing Beads Glucose oxidase (GOX)-immobilized cellulose beads are prepared as follows: Cellulose acetate (CA)/cellulose acetate phthalate (CAP) beads (microparticles) are prepared with a spray dry technique using a nebulizer apparatus (FIG. 20). A THF solution containing 0.6 wt % of CA and 0.3% of CAP is sprayed with a micronebulizer 512. A heated airstream is provided with a heat gun 500. The air stream carries the nebulized liquid droplets away from the nebulizer, drying them rapidly. The dried, fine beads are collected with a cyclone chamber 526, as described above positioned to intercept the stream of air and beads. The diameter of the beads is generally in the range of 1-3μ, with at least about 90% of the beads falling in this range. The enzyme GOX is then immobilized covalently on the CA/CAP beads using a coupling reagent: 1-ethyl-3-[3-(dimethylamino)propyl]carbodiimide hydrochloride (EDC-HCl). Specifically, 100 mg of the CA/CAP beads are treated with 1 ml PBS solution containing 10 mg of EDC-HCl for 1 hour. After washing the EDC-HCl treated CA/CAP beads with water, the beads are treated with 1 ml of PBS solution containing 5 mg of GOX. After 6 hours, the GOX-loaded beads are rinsed with a PBS solution and then dried in air.

b) Preparation of Optical pH Sensing Beads

Poly(vinyl chloride) (PVC) beads are prepared with a spray dry method similar to that described for the glucose sensing beads. Specifically, a THF solution containing 1 wt % of PVC and 1 wt % of BEHS is sprayed from the nebulizer under a heated airstream from the heat gun and the PVC/BEHS beads collected in the cyclone chamber 526. The diameter of the beads is generally in the range of 1-3μ, with at least about 90% of the beads falling in this range. An optical sensing mixture is then immobilized on the particles. Specifically, 50 mg of BEHS was mixed with 0.5 mg of pH sensitive chromoionophore III: 9-(diethylamino)-5-(octadecanoylimino)-5H-benzo[a]phenoxazine; 1.6 mg of a lipophilic anion: NaHFPB; 22.4 mg of a sodium ionophore: bis [(12-crown-4)methyl]2-dodecyl-2-methylmalonate.

c) Preparation of Optical Glucose Sensing Beads

A bead mixture for glucose sensing is prepared by mixing 10 mg of GOX-loaded beads as prepared for a) above, with 90 mg of optical pH sensing beads, as described for b) above.

d) Preparation of Optical Potassium Ion Sensing Beads

To 200 mg of PVC/BEHS beads, prepared as for b) above, an optical sensing mixture for K⁺ sensing is added. The mixture includes 50 mg BEHS, 0.5 mg of pH sensitive chromoionophore III; 1.6 mg of NaHFPB; 7.5 mg of a potassium ionophore: 2-dodecyl-2-methyl-1,3-propanedil bis[N-{5'-nitro(benzo-15-crown-5)-4'-yl]carbamate.

e) Preparation of Optical White Reference Beads

PVC/BEHS beads, prepared as described above, are used as an optical white reference to obtain spectral information on the skin and tissue between the sliver and an external optical detector positioned above the skin.

f) Preparation of Sensor Body

A body as shown in FIG. 19 is prepared. A cellulose acetate plate of 250μ thickness is formed by casting a THF solution containing 10 wt % of CA onto a slide glass. Gradual evaporation of the solvent under THF saturated atmosphere allows obtaining transparent and flat plates of CA. The thus prepared CA plate is covered with a brass mask with 200 μm thickness, in which four holes with 350 μm diameter are aligned in line where the distances in between holes are 500 μm to create four sensing compartments in a single sensor body. The precise laser drilling of the cellulose acetate plate with the mask is carried out by the 193 nm output of an ArF excimer laser system (Compex 200, Lambda Physik GmbH, Coettingen, Germany) with 7 Hz repetition rate. The average energy of the leaser beam per pulse is 288 mJ. The thus drilled CA plate was cut out as shown in FIG. 19.

Adhesion of the Sensor Window Membrane:

To form the sensor transparent layer 216, a THF solution containing 2 wt % of CA is applied onto a cover glass and allowed to gradual evaporate under THF saturated atmosphere. The thickness of the obtained CA membrane is 10□m. This membrane is cut off from the cover glass and placed on a Teflon plate. A sensor body is put on the membrane and adhered with a very small portion of a dichloromethane solvent by using a pulled Pasteur pipette. The tip diameter of the pipette is around 10 μm.

Stuffing of the Sensing Beads into the Sensor Body:

A sensor body is placed on a 1 wt % agar gel slab containing PBS buffer with the sensor window membrane 216 down. In separate sensor compartments 212a, 212b, 212c, 212d, glucose sensing beads 162, 164; pH sensing beads 164; K⁺ sensing beads; and optical white reference beads are stuffed, respectively. After small portions of PBS solution are applied into each sensing compartment, CA plates 222a, 222b, 222c, 222d 500 μm square and 30 μm in thickness are placed on each opening and adhered with a very small amount of THF solution containing 10 wt % of cellulose acetate by using a pulled Pasteur pipette. The THF solvent does not enter the sensing compartment due to the very low solubility of THF in PBS buffer solution.

Polyurethane Membrane Coating:

A chloroform solution containing 0.5 wt % of polyurethane is applied on a surface of a 1 wt % agar gel slab prepared from pure water. After the solvent evaporates under chloroform-saturated atmosphere, a sensor body stuffed with sensing beads is placed on the polyurethane membrane 225 with the sensing window membrane 216 down. The thickness of the polyurethane membrane was 2 μm. To coat whole sensor body, a small amount of chloroform solution containing 1 wt % of polyurethane was carefully applied from the backside of the window membrane by using a pulled pipette.

Example 11

In Vivo Potassium Responses of a Capsule Array-Type of Sensor Probe

A probe is prepared as described for Example 10. The probe is inserted into PBS buffer solutions containing different concentrations of K⁺.

Figure 30:
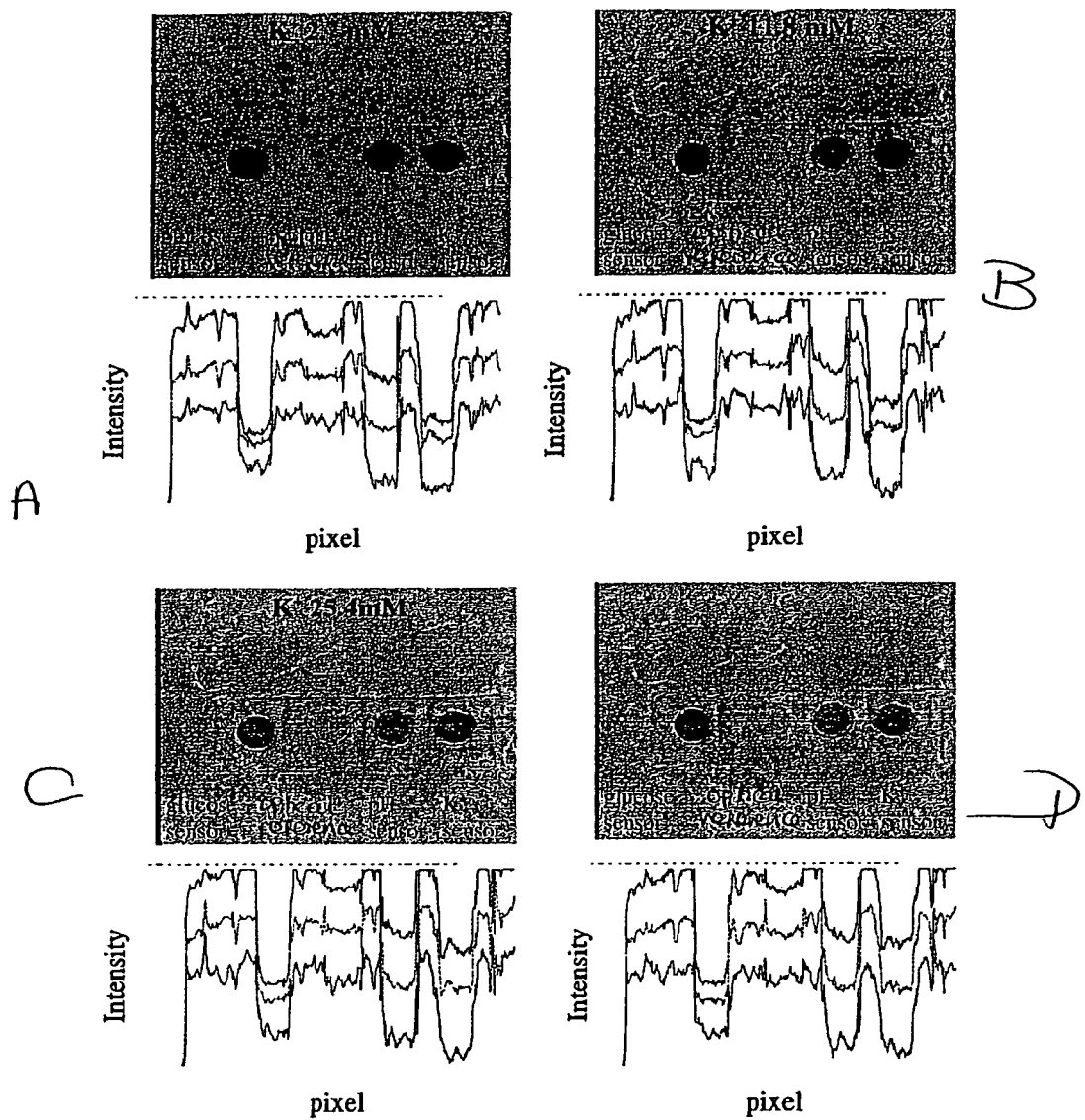
FIG. 30 shows images of the sensor of FIG. 19 in a PBS buffer solution containing various concentrations of $K^+$ taken by a color CCD camera, below each image, is a plot of the red, green and blue (RGB) color intensities at each pixel on the red line in the corresponding image.

FIG. 30 shows images of the thus prepared sliver sensor in a PBS buffer solution containing various concentrations of K⁺ taken by a color CCD camera together with the red, green and blue color intensities at each pixel on the red line in the corresponding image. It can be seen that the color of the K⁺ sensing capsule in the sensor probe changes from dark blue to orange with increasing concentration of K⁺, reflecting the increase in the red color intensity in the corresponding image. Potassium ion concentrations were 2.7 mM, 11.8 mM, 25.4 mM, and 52.7 mM for FIGS. 30A, B, C, and D, respectively.

Figure 31:
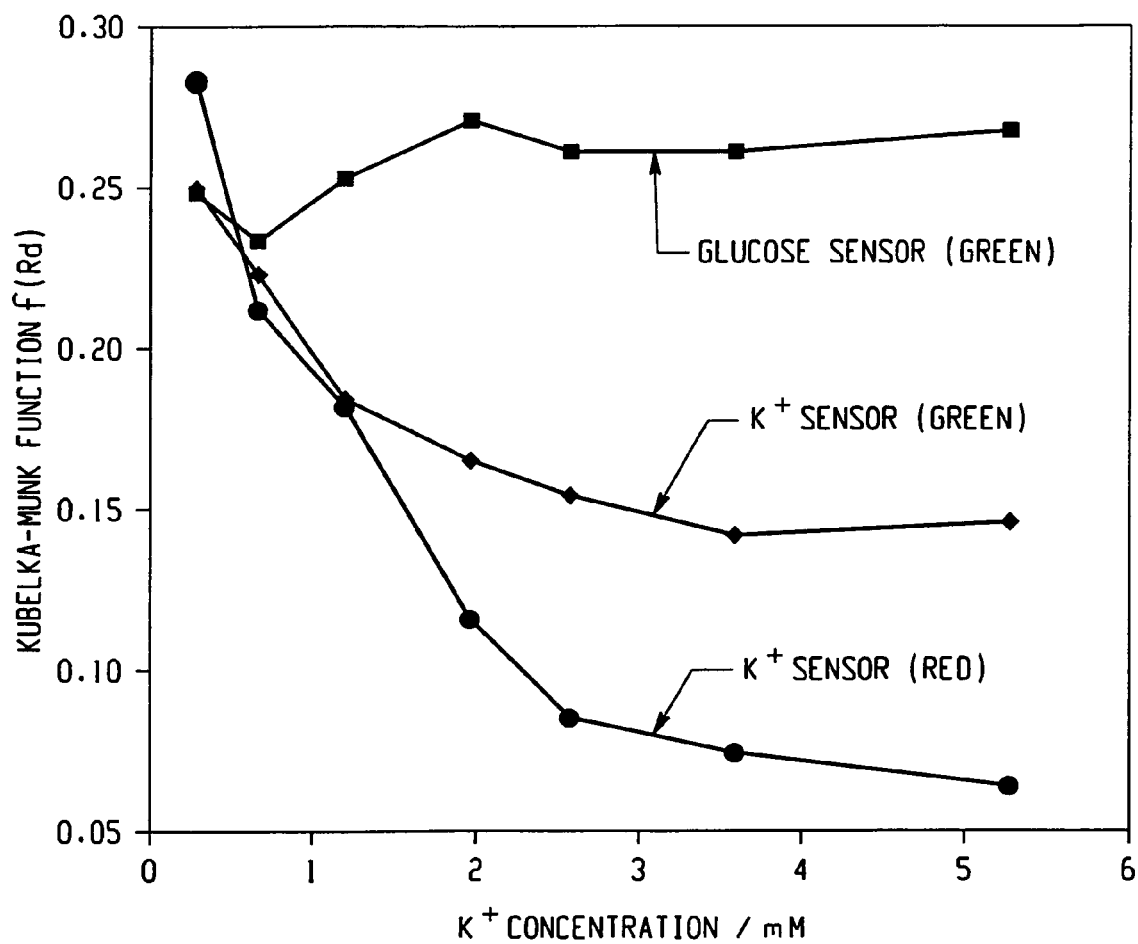
FIG. 31 shows a plot of the relationship between the concentration of $K^+$ in the PBS buffer solution and the Kubelka-Munk (KM) function, $f(R_d)$, of averaged RGB color intensities of the pixels corresponding to the sensing capsule array of FIG. 19.

The relationship between the concentration of K⁺ in the PBS buffer solution and the Kubelka-Munk (KM) function, $f(R_d)$, of averaged RGB color intensities of the pixels corresponding to the sensing capsule is shown in FIG. 31.

In the KM theory describing the optical property of a translucent medium which absorbs and scatters light, the observed light intensity, $R_{obs}$, is converted to $f(R_d)$ which is proportional to the concentration of the absorbent.

$$f(R_d) = (1-R_d)^2/2R_d$$

and $$R_d = R_{obs}/R_{ref}$$

where $R_{ref}$ is the light intensity from the optical white reference capsule.

It can be seen that $f(R_d)$ value of the red and also green color in the K⁺ sensing capsule decreases with increasing concentration of K⁺ whereas the color intensity in the glucose sensing capsule does not change.

Example 12

In Vitro Glucose Responses of the Capsule Array-Type Sensor Probe

Figure 32:
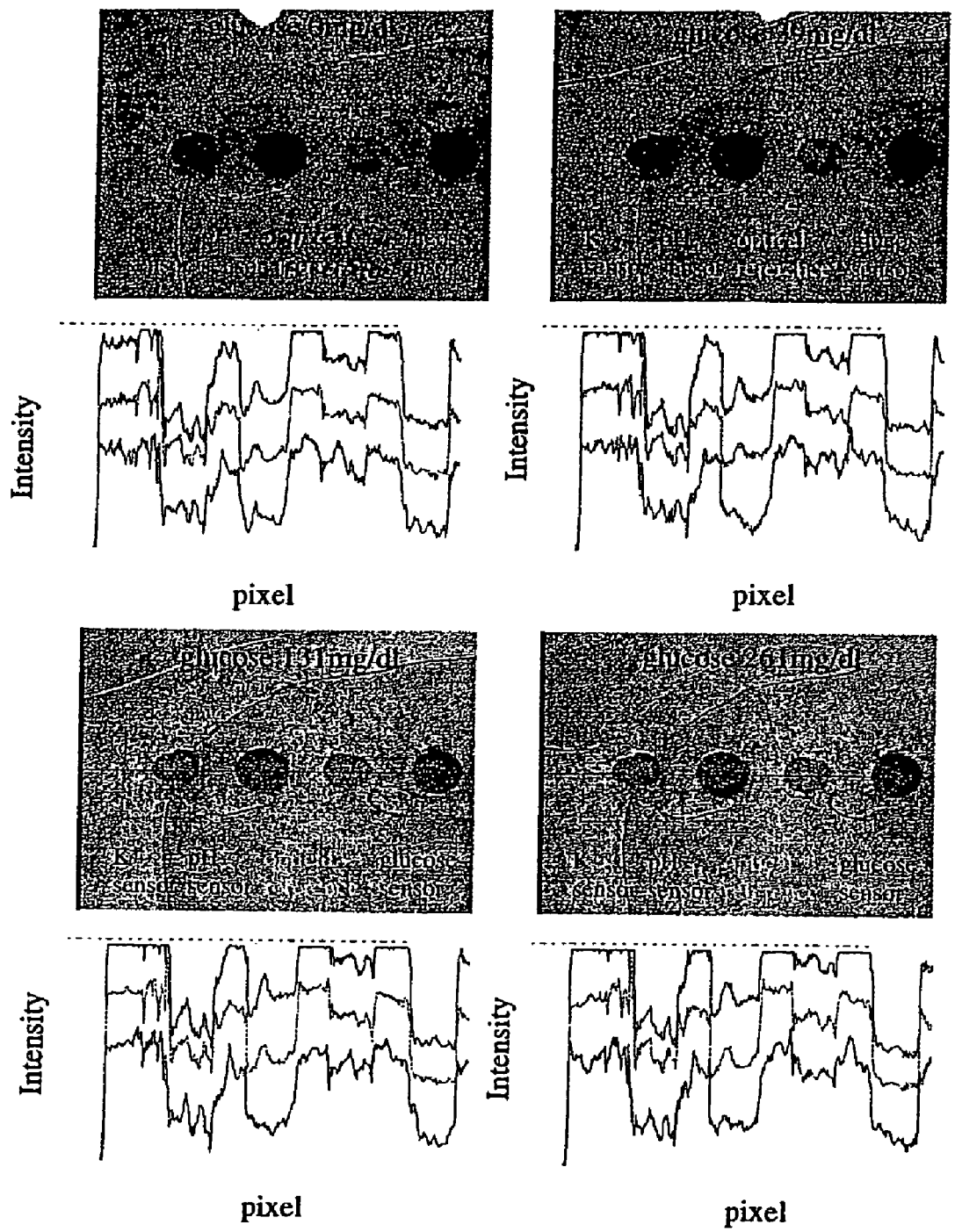
FIG. 32 shows images of the "capsule/array type" sensor probe of FIG. 19 in a PBS buffer solution containing various concentrations of glucose taken by a color CCD camera, below each image, is a plot of the RGB color intensities at each pixel on the red line in the corresponding image.

A probe is prepared as described for Example 10. The probe is inserted into PBS buffer solutions containing different concentrations of glucose. FIG. 32 shows the images of the sensor probe in a PBS buffer solution containing various concentrations of glucose together with the red, green and blue color intensities at each pixel on the red line in the corresponding image. It can be seen that the color of the glucose sensing capsule in the sliver sensor changes from dark orange to dark blue with increasing concentration of glucose, reflecting the decrease in the red color intensity in the corresponding images. No color changes of the pH or K⁺ sensing capsules with changing glucose concentration were observed.

Figure 33:
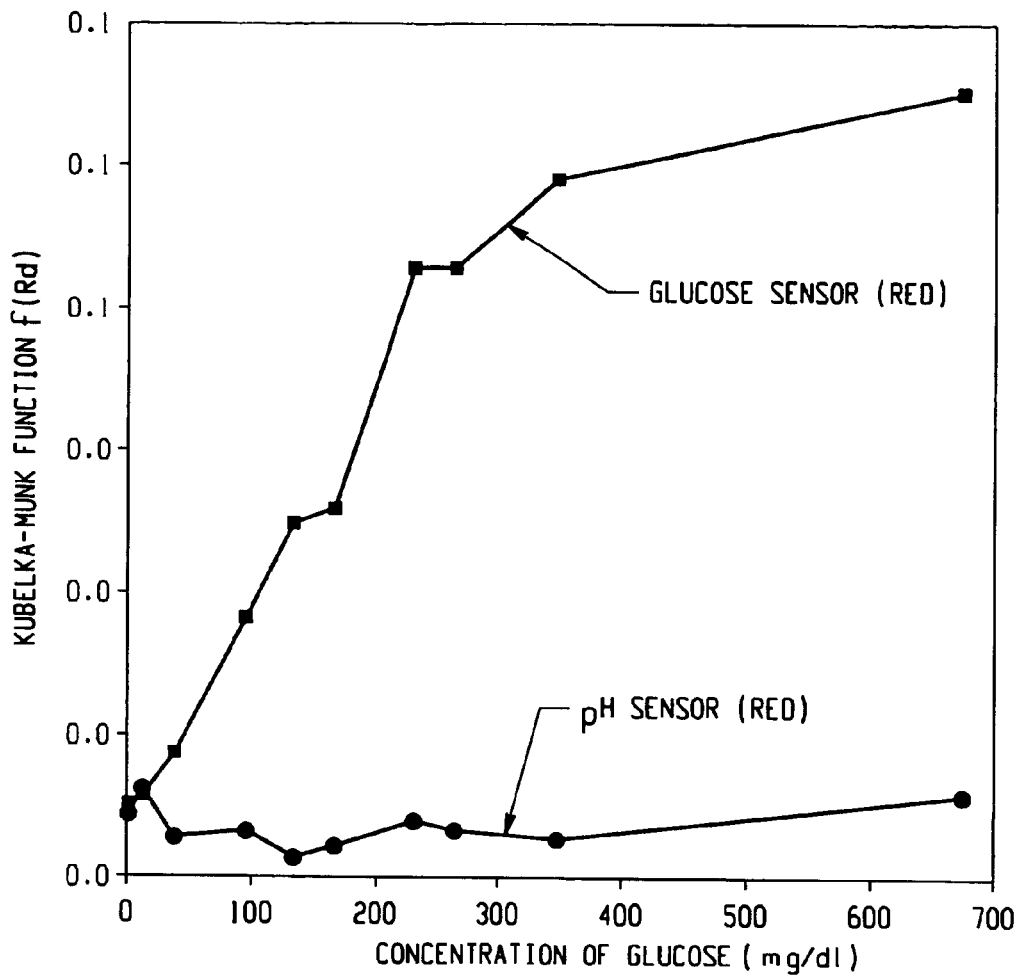
FIG. 33 shows a plot of the relationship between the concentration of glucose in the PBS buffer solution and the Kubelka-Munk (KM) function, $f(R_d)$, of averaged RGB color intensities of the pixels corresponding to the sensing capsule array of FIG. 19.

The relationship between the concentration of glucose in the PBS buffer solution and the Kubelka-Munk (KM) function, $f(R_d)$, of averaged red color intensities of the pixels corresponding to the sensing capsule is shown in FIG. 33. It is clear that $f(R_d)$ value of the red color in the glucose sensing capsule decreases with increasing concentration of glucose whereas no significant change in the KM values of pH sensitive and K⁺ sensitive capsules was observed.

This successful change in color of the sensing capsule for glucose in the clinical concentration range even in the PBS buffer solution demonstrates not only the feasibility of this tiny sensing capsule as an element for the optical glucose sensor probe but also the potentiality of a color CCD camera as a detector for the sensor probe.

Example 13

In Vivo Responses of the Capsule Array-Type Sensor Probe

A sensor probe prepared as described for Example 10 is implanted into the skin of a diabetic rat.

An image taken with a CCD digital camera located above the skin clearly shows three colored areas corresponding to the glucose sensing capsule, white reference, and pH sensors, respectively.

Other Embodiments of a Sensor Probe

A glucose sensor probe can be prepared with the following properties:
1. The sliver sensor spontaneously and reversibly changes color that reflects glucose concentration, thus making a power source unnecessary.
2. Color change can be monitored from outside the body if the color spot is located close to the skin surface (within the dermis, but under the epidermis).
3. So neither wires nor optical fibers cross the skin, eliminating track infection, and the three day FDA limit.
4. The sliver sensor contains only plastic type materials which should make it far more biocompatible than conventional sensors. Biocompatibility studies proved full biocompatibility up to at least 28 days.
5. No toxic osmium or other complexes are used. Toxicity of the components used in the sliver is either none, or very little for some dyes, even if the dyes are in a freely diffusing, dissolved form. However, the molecules are entrapped not only by the biocompatible outer membrane but they are also attached to beads or covalently bound to larger particles inside the sliver. This makes them biologically harmless even in the unlikely case of a spill.
6. The signal obtained is not a single value, but rather, a color. Color is measured as a spectrum, and thus, it consists of many independent values. This makes it possible to determine glucose concentration very reliably, even from very weak signals and despite of eventual noise. Moreover, false and "true" readings can be told apart, since false show up as a spectrum that is not a possible one for glucose. Self test is thus possible using a mathematical "shape" approach.

Further sensing spots can be added to the same sliver such as pH, potassium, lactate, and other sites, all of which can be read the same way-using color changes. Unlike sensors which have wiring, a sensor of about 200-300 microns in diameter and 1 mm long, placed only about 100-200 microns deep, without wiring to the surface results in no pain to the wearer whatsoever.

Successful long term (1 month) in vivo biocompatibility studies and in vivo functionality studies were performed with a CA-based, polyurethane-coated sliver sensor formed as for FIG. 19.

The sensor body 214 of FIG. 19 or capsule housing 160 of FIG. 16 can also be formed from a polymer of 2-hydroxyethyl methacrylate (HEMA). The HEMA polymer material has the following advantageous characteristics with respect to polyurethane-coated CA:
1. It is more amenable to microfabrication, manual or automated;
2. HEMA-based sliver bodies are clear and exhibit smooth surfaces and high-definition boundaries, including those of the sensing wells;
3. HEMA is one of the best implant materials with excellent biocompatibility and robustness;
4. HEMA is a hydrophilic polymer which is tunable by adding a variable quantity of another biocompatible but hydrophobic materials to achieve any desired degree of hydrophobicity, thus making a polyurethane outer coating unnecessary;
5. The entire sliver body, including the seal of both openings of the sensing wells, can be made from a single piece of optimized HEMA;
6. Such single piece design lends superior mechanical integrity to the sliver, even under eventual sustained mechanical wear in vivo.

The sensor body can be formed from monomers which are placed in a mold or and cured, for example with UV light. Alternatively, a suitably shaped block is formed for the body and etched to form cavities, e.g., with an excimer laser. In addition to HEMA, other monomers can be incorporated, such as poly(ethylene glycol)methacrylate and di(ethylene glycol)dimethacrylate. A HEMA-based sensor capsule membrane can be used regulate glucose permeability by changing the monomer ratio of HEMA (hydrophilic) to poly(ethylene glycol)methacrylate (less hydrophilic) and di(ethylene glycol)dimethacrylate (a cross linking reagent to regulate the "mesh" size of the polymer). This can be used in place of a polyurethane membrane. The mixture used to form the body and membrane may also include one or more cross linking agents, photoinitiators, and the like. Other acrylate monomers may be used in addition to or in place of HEMA which are visible and/or IR transparent and, for in vivo use, which are biocompatible.

In one embodiment, the sensor body is formed from a mixture of 85 wt % HEMA, 5 wt % poly(ethylene glycol) methacrylate, 1 wt % di(ethylene glycol)dimethacrylate (as a cross linking reagent), 8.9 wt % $H_2O$, and 0.1 wt % dimethoxy-phenylacetophenone (Irgacure 651, Ciba) (as a photoinitiator) Curing can be carried out with a 0.1 W 365 nm UV lamp for 15 min. The sensor window membrane can be formed from a mixture of 45 wt % HEMA, 45 wt % $H_2O$, 9.9 wt % poly(ethylene glycol)methacrylate, and 0.1 wt % dimethoxy-phenylacetophenone (Irgacure 651, Ciba) (as a photoinitiator). Curing can be carried out with a 0.1 W 365 nm UV lamp for 15 min.

For in vivo applications, it is beneficial to regulate the glucose permeation by the sensor capsule (window) membrane due to low oxygen concentration. This can be achieved with a multilayer membrane (polyurethane and cellulose acetate), as described previously. In a HEMA-based sensor body, the glucose permeability is easily controlled by changing the ratio of hydrophilic HEMA monomer to hydrophobic (less hydrophilic) poly(ethylene glycol)methacrylate, and (also, the proportion of a cross linking monomer/photoinitator (such as dimethoxy-phenylacetophenone). Control of the mesh size of this hydrogel (HEMA-based polymer) can be achieved by changing the added amount of cross linking monomer.

A HEMA-based sensor body is capable of uptake of drugs from an in vitro drug solution and then release them gradually after implantation under the skin. Therefore, it is easy to introduce anti-infection drugs or immuno reaction-regulated drugs into the implanted site, such as antibiotics or steroids. For example, the sensor body is dipped into the drug solution, then the sensor probe is implanted. The drugs loaded into the HEMA polymer are gradually released into the implanted site to prevent any infection and unfavorable body reactions. Suitable antibiotics to prevent infection include penicillin, tetracycline, erythromycin etc, Steroids, including cyclosporine FK506, are suitable drugs to regulate immunoreaction.

The sensor body and capsule membrane (window membrane) may consist of polyHEMA and/or other similar polymers, such as polyHEMA-poly(ethylene glycol)methacrylate copolymer.

In one embodiment, in place of color dyes which operate in the visible range of light, dyes can be employed which operate in the infrared (IR) spectrum. A hugely enhanced color response from dyes in the IR range can be obtained. In addition, IR light penetrates far deeper in the body than visible light. Thus, a sensor probe can be placed deeper under the skin, yet it will remain easily addressable and readable from outside the body. Suitable dyes include those which absorb in the near Infrared (NIR) range of the spectrum. Exemplary dyes of this type include "ketocyanine" dyes. The following dyes are suitable although a wide variety of IR absorbing dyes may also be used:
1. 2,5-bis{[3,3-dimethyl-1-propylindolenine]ethylidene}cyclopentanone
2. 2,5-bis{[1-ethylbenzooxazolenine]ethylidene}cyclopentanone
3. 2,5-bis{[1,3,3-trimethylbenz[e]indolenine]ethylidene}cyclopentanone
4. 2,5-bis{[1-ethylbenzothiazolenine]ethylidene}cyclopentanone
5. 2-{[3-ethylbenzothiazolidene]ethylidene}-5-{[1,3,3-trimethylbenz[e]indolenine]ethylidene}cyclopentanone Because color CCD has some sensitivity in the NIR range, a conventional CCD camera can be used to record the color change. Thus, for IR absorbing dyes, a light source which emits in the IR, particularly NIR, such as an NIR LED can be used in place of a light source which emits primarily in the visible range. It is also contemplated that a light source which emits in both the IR and visible ranges be used. Optionally a detector which detects only in the IR range or a portion thereof may be used. Suitable filters may be used in combination with such a detector to filter out unwanted regions of the electromagnetic spectrum.

HEMA and other acrylate polymers are suitable for forming the sensor body to be used with an IR absorbing dye as they are substantially transparent to IR light, particularly NIR. Other IR transparent materials may alternatively be used for the sensor body.

The use of IR dyes is not limited to glucose detection. For example, an IR dye can be used in a pH sensing capsule.

Anions may be used in the sensing capsules, such as sodium tetrakis[3,5-bis(1,1,1,3,3,3-hexafluoro-2-methoxy-2-propyl)phenyl]borate. This lipophilic anion is added into the pH sensing beads (oil phase) together with a near infrared (NIR) pH sensing dye. Under the condition that the sodium concentration in the body fluid (aqueous phase, also inside the glucose sensor capsule) is constant, the pH decrease inside the glucose sensing capsule due to the enzymatic reaction leads to increases in the protonated dye. Also a decrease in the sodium as a counter cation of the above lipophilic anion in the oil phase (pH sensing beads) occurs. This is an ion exchange reaction of sodium and proton between aqueous and oil phases. The role of the lipophilic anion sodium salt is to maintain electroneutrality in the oil phase (beads) when the dye is protonated or deprotonated (to keep the same net charge of cations and anions in this phase).

Figure 35:
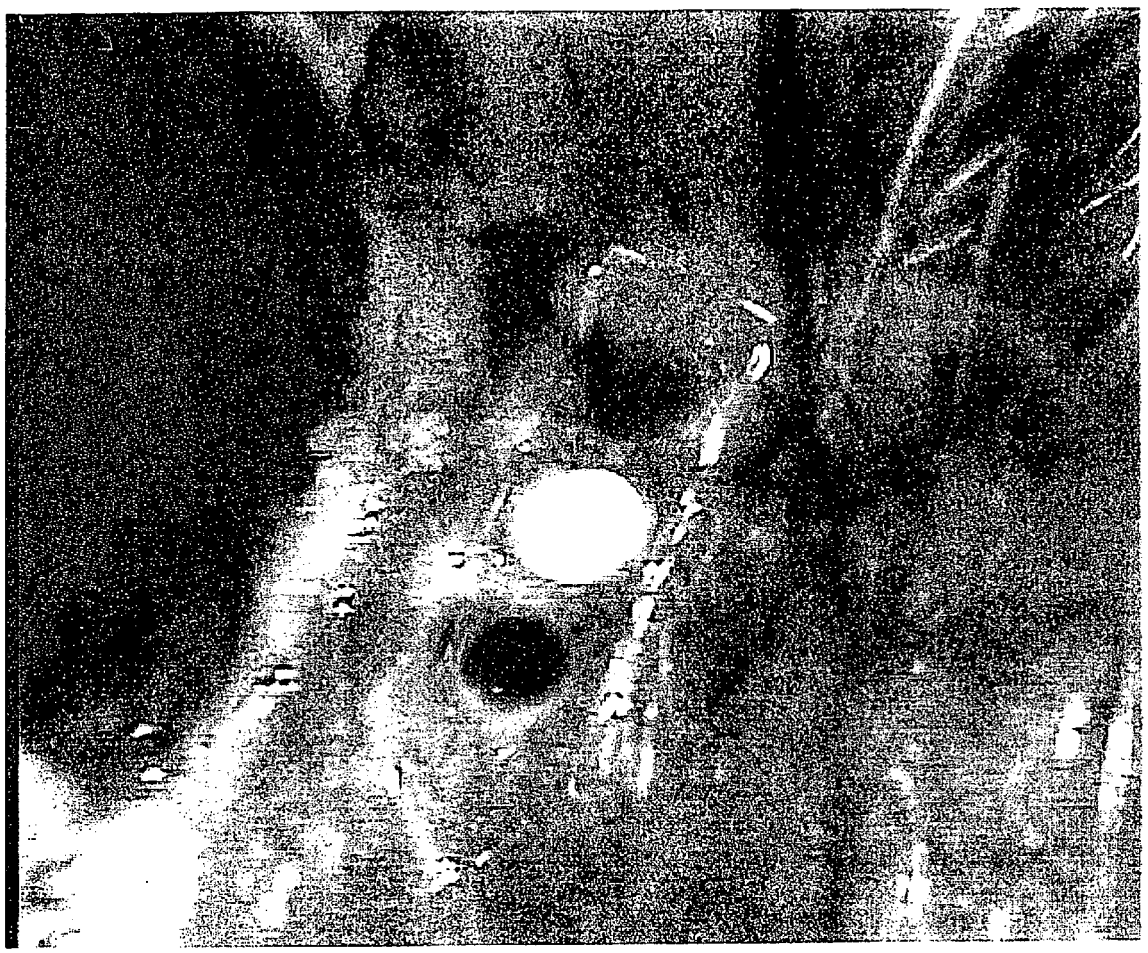
FIG. 35 shows the in vivo response of a glucose and pH sensor probe exposed to IR light.

In vivo results have been obtained with a sliver sensor using a dye which shows a detectable change in response to glucose when illuminated with IR light. In one experiment, a sensor probe was deliberately placed much deeper (several millimeters) under the skin of a rat than in previous studies. Although the sensor probe could not be seen in visible white light, it clearly emerged when IR light was used. A sensor placed on top of connective tissue under an incision in the skin of the animal immediately changed color, reflecting the high glucose level expected for this diabetic rat. In FIG. 35, the clear HEMA sensor body and its smooth surfaces and almost perfect shape are visible. The white spot in the center is for optical reference and does not change color. The upper well contains a pH sensor and its color corresponds to pH expected in the interstitial fluid (ISF). The lower well is the glucose sensing spot and its color is clearly much darker and closer to blue, reflecting high glucose level in the ISF. When the probe was removed from the animal, this sensing spot reverted back to the original orange color that corresponds to no (or very low) glucose.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A multivariable sensor system for simultaneously detecting one or more analytes in a fluid of a person, said sensor system comprising:
   an elongated sensor body including an array of spaced apart cavities;
   a plurality of optode sensing microbeads disposed in at least one cavity, said plurality of optode sensing microbeads comprising a first set of microbeads that include an indicator material and a detection substance;
   a reference element disposed in at least one other cavity for providing a standard color by which a color change of said plurality of optode sensing microbeads is compared; and
   a multilayered analyte-permeable membrane covering each of said cavities;
   wherein said detection substance comprises an enzyme that reacts with the analyte or catalyzes the reaction of the analyte to produce a detectable reaction product;
   wherein said at least one indicator material comprises a light-absorbing, pH-sensitive dye that undergoes a color change in response to the analyte or to the detectable reaction product thereof;
   wherein the color change is reversible depending upon the concentration of the one or more analytes.

2. The sensor system of claim 1, wherein each of said cavities has an opaque or mirrored base to aid in viewing of said sensing microbeads without interference from underlying skin color.

3. The sensor system of claim 1, wherein said plurality of sensing microbeads include a second set of microbeads having at least one detection substance immobilized thereon.

4. The sensor system of claim 1 further including a third set of microbeads disposed in at least one of said spaced apart cavities, said third set of microbeads being colored to facilitate diffuse reflectance in said sensor system.

5. The sensor system of claim 1, wherein a negatively-charged hydrophilic gel is disposed in each of said spaced apart cavities, said negatively-charged hydrophilic gel including at least one polyanion to reduce the buffer capacity of said sensor system in vivo.

6. The sensor system of claim 1, wherein said multilayered analyte-permeable membrane is transparent.

7. The sensor system of claim 1, wherein said multilayered analyte-permeable membrane is permeable to select molecules.

8. The sensor system of claim 7, wherein said multilayered analyte-permeable membrane excludes at least one of anions, lipids and proteins.

9. The sensor system of claim 1, wherein said multilayered analyte permeable membrane further comprises:
 an outermost layer that is in contact with the fluid;
 a middle layer for regulating and limiting the diffusion of molecules into each of said spaced apart cavities; and
 a negatively-charged inner layer that is in contact with said microbeads, said negatively-charged inner layer being formed from a combination of cellulose acetate and cellulose acetate phthalate in a ratio that allows the diffusion rate of charged ions into said at least one cavity including said plurality of sensing optode microbeads to be controlled.

10. The sensor system of claim 1, wherein each of said plurality of optode sensing microbeads is comprised of a lipophilic hydrogen ion-sensitive dye, an ionophore, and a lipophilic ion.

11. A multivariable sensor system for simultaneously detecting one or more analytes in a fluid of a person, said sensor system comprising:
 an elongated sensor body including an array of spaced apart cavities;
 a plurality of sensing optode microbeads disposed in at least one cavity, said plurality of sensing optode microbeads comprising a first set of microbeads that include an indicator material and a second set of microbeads that include a detection substance;
 a plurality of reference microbeads disposed in at least one other cavity for providing a standard color by which a color change of said plurality of optode sensing microbeads is compared; and
 a multilayered analyte-permeable membrane covering each of said cavities;
 wherein said detection substance comprises an enzyme that reacts with the analyte or catalyzes the reaction of the analyte to produce a detectable reaction product;
 wherein said at least one indicator material comprises a light-absorbing, pH-sensitive dye that undergoes a color change in response to the analyte or to the detectable reaction product thereof;
 wherein the color change is reversible depending upon the concentration of the one or more analytes.

\* \* \* \* \*